(12) United States Patent
Schultheiss et al.

(10) Patent No.: US 10,462,994 B2
(45) Date of Patent: Nov. 5, 2019

(54) FUNGAL RESISTANT PLANTS EXPRESSING HCP7

(71) Applicant: BASF PLANT SCIENCE COMPANY GMBH, Ludwigshafen (DE)

(72) Inventors: Holger Schultheiss, Boehl-Iggelheim (DE); Ralf Flachmann, Limburgerhof (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 14/763,652

(22) PCT Filed: Jan. 10, 2014

(86) PCT No.: PCT/EP2014/050387
§ 371 (c)(1),
(2) Date: Jul. 27, 2015

(87) PCT Pub. No.: WO2014/117988
PCT Pub. Date: Aug. 7, 2014

(65) Prior Publication Data
US 2015/0353957 A1    Dec. 10, 2015

(30) Foreign Application Priority Data

Jan. 29, 2013 (EP) .................................... 13152970

(51) Int. Cl.
| C12N 15/82 | (2006.01) |
| A01H 5/10 | (2018.01) |
| A01H 1/02 | (2006.01) |
| C07K 14/415 | (2006.01) |

(52) U.S. Cl.
CPC .................. *A01H 5/10* (2013.01); *A01H 1/02* (2013.01); *C07K 14/415* (2013.01); *C12N 15/8279* (2013.01); *C12N 15/8282* (2013.01)

(58) Field of Classification Search
None
See application file for complete search history.

(56) References Cited

FOREIGN PATENT DOCUMENTS

| WO | WO-02/20791 A1 | 3/2002 |
| WO | WO-2012/172498 A1 | 12/2012 |
| WO | WO-2013/001435 A1 | 1/2013 |
| WO | WO-2013/092275 A2 | 6/2013 |
| WO | WO-2013/093738 A1 | 6/2013 |
| WO | WO-2013/149801 A1 | 10/2013 |
| WO | WO-2013/149804 A1 | 10/2013 |
| WO | WO-2013/152917 A1 | 10/2013 |
| WO | WO-2014/024079 A2 | 2/2014 |
| WO | WO-2014/024090 A2 | 2/2014 |
| WO | WO-2014/024102 A1 | 2/2014 |
| WO | WO-2014/041444 A1 | 3/2014 |
| WO | WO-2014/076614 A1 | 5/2014 |
| WO | WO-2014/076659 A1 | 5/2014 |
| WO | WO-2014/117988 A1 | 8/2014 |
| WO | WO-2014/117990 A1 | 8/2014 |
| WO | WO-2014/118018 A1 | 8/2014 |
| WO | WO-2014/135682 A1 | 9/2014 |

OTHER PUBLICATIONS

Yamada et al. Accession No. AY113951; deposited 2002.*
Friedberg.Brief. Bioinformatics. 7: 225-242, 2006.*
Fourgoux-Nicol et al. Plant Molecular Biology 40: 857-872; 1999.*
Guo et al. Proc. Natl. Acad. Sci. USA 101:9205-9210, 2004.*
Hill et al. Biochem. Biophys. Res. Comm. 244:573-577, 1998.*
Borhan et al. Molecular Plant Pathology (2010), vol. 11(2); pp. 283-291.*
Goellner et al (Molecular Plant Pathology (2010).*
Chini et al., "Motifs specific for the ADR1 NBS-LRR protein family in *Arabidopsis* are conserved among NBS-LRR sequences from both dicotyledonous and monocotyledonous plants", *Planta*, 221: 597-601 (2005).
EMBL Accession No. AY050794, "*Arabdopsis thaliana* putative disease resistance (At5g04720) mRNA, complete cds" dated Aug. 27, 2001.
European Search Report for Application No. EP 13 15 2970 dated Jun. 7, 2013.
Godoy et al., "Diagrammatic scale for assessment of soybean rust severity", *Fitopatol. Bras.* 31(1): 63-68 (2006).
Grant et al., "Targeted activation tagging of the *Arabidopsis* NBS-LRR gene, ADR1, conveys resistance to virulent pathogens", *MPMI*, 16(8): 669-80 (2003).
Heath, "Cellular interactions between biotrophic fungal pathogens and host or nonhost plants", *Can. J. Plant Pathol.* 24: 259-64 (2002).
International Search Report and Written Opinion for Application No. PCT/EP2014/050387 dated Mar. 21, 2014.
Neu et al., "Cytological and molecular analysis of the *Hordeum vulgare-Puccinia triticina* nonhost interaction", *Mol. Plant Microbe Interact.* 16(7): 626-33 (2003).
Rytter et al., "Additional alternative hosts of *Phakopsora pachyrhizi*, causal agent of soybean rust", *Plant Dis.* 68(9): 818-9 (1984).

(Continued)

*Primary Examiner* — Medina A Ib

(56) References Cited

OTHER PUBLICATIONS

Sinclair et al., (eds.) Proceedings of the Soybean Rust Workshop, Aug. 9-11, 1995. Urbana, IL: National Soybean Research Laboratory, (1995).

Smith et al., "Known host crops of *Phakopsora pachyrhizi* causal agent of soybean rust (SBR)", Internet Citation: 1-6 (2006).

* cited by examiner

Figure 3:

```
                        1                                                           60
    HCP7-cDNA      (1)  ------------------------------------ATGGCAGATTAATCGGCGGAA
genomic sequence   (1)  ACTTATCTCTCTCTCTTTTTCTCATCGGCCTTTGCATGGCAGATTAATCGGCGGAA
HCP7-cDNA-optimized (1) ------------------------------------ATGGCCGATTAATCGGAGGTGAG
                        61                                                          120
    HCP7-cDNA     (25)  GTTGTGACGCAGCTCGAGGCGGCAGCTTCTAGCGGTTCTGGTTTCTCAAAACCCTCATCGAG
genomic sequence  (61)  GTTGTGACGCAGCTCGAGGCGGCAGCTTCTAGCGGTTCTGGTTTCTCAAAACCCTCATGGAG
HCP7-cDNA-optimized (25) GTTGTGACTCAGCTCGTTGTTAGCCAGTCTCTACCCCTTAGTGAGTTCAAGACCCTTAGTGTACG
                        121                                                         180
    HCP7-cDNA     (85)  GCGATGGCCAAATTCCCGGATCAATCTCACATCCACCCACTGATCAGCGCTTCTACCAGATCATCGGATC
genomic sequence  (121) GCGATGGCCAAATTCCCGGATCAATCTCACATCCACCCACTGATCAGCGCTTCTACCAGATCATCGGATC
HCP7-cDNA-optimized (85) CCGATACTCAAGAACCTTCAGCGCCGGTGAACTCAGCAAGACCAGCTAACTAACCGCCTACTATCAAGAATT
                        181                                                         240
    HCP7-cDNA     (145) CAATTACAACGGCGGCGGCGTCAGCTCACAGTCGAAGCTTCTTAATCAAGCCTTCTAATTGTTTCCGAA
genomic sequence  (181) CAATTACAACGGCGGCGGCGTCAGCTCACAGTCGAAGCTTCTTAATCAAGCCTTCTAATTGTTTCCGAA
HCP7-cDNA-optimized (145) CAGTACTCAGGCGGCTAAGAACCTACACCACCAGACAGAAGAAGTTCTTAATCAAGCCTTGAACATG
                        241                                                         300
    HCP7-cDNA     (205) ACGTACTCAGGCGGTCAGGCGGTAAGGAAGTTAGCCGCGTAAGCGCAGCTTCTTGCTGCTTAGAGAATATG
genomic sequence  (241) ACGTACTCAGGCGGTCAGGCGGTAAGGAAGTTAGCCGCGTAAGCGCAGCTTCTTGCTGCTTAGAGAATATG
HCP7-cDNA-optimized (205) ACTCTCCGCCTTAACGGATGGTGCCGCAGCTCGTTGTCCTCCTGTGCTCAAGTGTTAAGTGCTTAAGAGTTCTCAGGTGGATAAG
                        301                                                         360
    HCP7-cDNA     (265) GTTAGCAGCAGCTGCAATTAGTTAGTCAAGTTCATGATTTCATCATTCAGTTCAGCAGTTCGACCGATTCT
genomic sequence  (301) GTTAGCAGCAGCTGCAATTAGTTAGTCAAGTTCATGATTTCATCATTCAGTTCAGCAGTTCGACCGATTCT
HCP7-cDNA-optimized (265) GTTAGGCAGCTGCAGCTCCGTGCGTGGTCCTTACGGTGCTTAAGGTGCTAAAGCCTTATGAGCTTAGCAGTTC
                        361                                                         420
    HCP7-cDNA     (325) CTTAACGGTCAGCTCCAATTGTTACGTCCATTGTCGTTCAGTCTCATGAAGTTCATGATCATGAAGCCGATTCT
genomic sequence  (361) CTTAACGGTCAGCTCCAATTGTTACGTCCATTGTCGTTCAGTCTCATGAAGTTCATGATCATGAAGCCGATTCT
HCP7-cDNA-optimized (325) CTTAACGGCTCAGCTCCGTCGTGCTGGTCCCTGAGTTGATGTGTCACCACCTTCACCACCGTCTAGGCTGACTCA
                        421                                                         480
    HCP7-cDNA     (385) GAATTCGGTTCGATCGGATGCATAGAAGTGATTCGTTCGTTGATAGTTCAAGTGAAGAGAAGGCTCGGTTCT
genomic sequence  (421) GAATTCGGTTCGATCGGATGCATAGAAGTGATTCGTTCGTTGATAGTTCAAGTGAAGAGAAGGCTCGGTTCT
HCP7-cDNA-optimized (385) GAGTTAGGTTCGATAGGATCGACCCTAAGGTGGACTCACTTAAGCGAGAAGAAGCGCGAGGCTCGGCTCT
                        481                                                         540
    HCP7-cDNA     (445) ATGAAAGCTGAGGGAAGTGAATCGTTCGTTGATGAGGGTTGAAGACGGCGAGGCTACCGTT
genomic sequence  (481) ATGAAAGCTGAGGGAAGTGAATCGTTCGTTGATGAGGGTTGAAGACGGCGAGGCTACCGTT
HCP7-cDNA-optimized (445) ATGAAGCTTAGGGGCTCAGAGTCACTTAAGACTTAAGACTTAAGACTTCTTAAGACTTCTAAGACTCAGGCTACCGTT
```

Figure 3 continued:

```
                      541                                                        600
HCP7-cDNA       (505) CAGATGGTGACAACCGATGGTGCTGATTGGGGGTGGATTGGATTTGGAAAGAGAAG
genomic sequence(541) CAGATGGTGACAACCGGTGCTGCTGATTGGGGGTGGATTGGATTTGGAAAGAGAAG
HCP7-cDNA-optimized(505) CAGATGGTACTACCGACGGTGTGCTGACTTGAGTGGGACTTGAGTCTCCTAAGCGTAAG
                      601                                                        660
HCP7-cDNA       (565) CTGAAGGACAATCGTGTTAAATCGTTGAATGGGAAAAACTTATTGCATTCTGCATTG
genomic sequence(601) CTGAAGGACAATTGTGTTAAATCGTTGAATGGGAAAAAGACTTATTGCATTCTGGATC
HCP7-cDNA-optimized(565) CTGAAGAGATCCTTAAGTCTAACCAGCAGAGCTGATCCGGATTAGTGCAATG
                      661                                                        720
HCP7-cDNA       (625) AGTTCTTCAGGGAAAAACCGACTTGCCAAACAGCTTGCGGCGAGCAGGAGCTTGAGG-
genomic sequence(661) AGTTCTTCAGGGAAAAGCGACTTGCCGAAGAGCTTGCGGGACGAGCAGCTTGAGCT
HCP7-cDNA-optimized(625) TCAGGCCTCAGGTAAGACTACCCTCGGTAAGGACTTGGTAGGGACCAAGAGGGTTAGGG-
                      721                                                        780
HCP7-cDNA       (684) ---------------------------------------------------------
genomic sequence(721) AATGAACTTTTCTTTGCTGGCCTCTGATTCCATATCGTTTGTTAATTTGCTTGGTACATCT
HCP7-cDNA-optimized(684) ---------------------------------------------------------
                      781                                                        840
HCP7-cDNA       (684) ---------------------------------------------------------
genomic sequence(781) TTGTGATCTCTATTGCAGTGGCTTTGTGGTGTTTCTTAATGGTATATTTTGTTGGTTTAT
HCP7-cDNA-optimized(684) ---------------------------------------------------------
                      841                                                        900
HCP7-cDNA       (684) ---------------------------------------------------------
genomic sequence(841) CTTGATGATCATGCTTCTATTGTTTTGTTGTTGTATAGTTGAGTTGCTAAAATTGCTTTCATT
HCP7-cDNA-optimized(684) ---------------------------------------------------------
                      901                                                        960
HCP7-cDNA       (684) ------------------------CCACTTGGGACAAGGTTTCTTTCTGCTCCTCTATCT
genomic sequence(901) TACTGCTTTTATACAGGCCACTTTGGGACAAGGTTTGTTTCTGCTCCTCTATCT
HCP7-cDNA-optimized(684) ------------------------CCACTTCCGTAACAAGGGTGTTCCTTACCGTAGTCAGCA
                      961                                                       1020
HCP7-cDNA       (727) CCGAATCTTGAGGAGCTTAGGAGCACCCATAATGGGGATTTCTTACTAGTTACAGGCTGGG
genomic sequence(961) CCGAATCTTGAGGAGCTTAGGAGCACCCATAATGGGGATTTCTTACTAGTTACAGGCTGGG
HCP7-cDNA-optimized(727) CCTAACCTCGAGGAAGCTAGGAGCCTCATAACTCGGGAGTCCTACTAGTTACGAGGCTGGT
                     1021                                                       1080
HCP7-cDNA       (787) GTTGGTGCTACTCCTCTTCCAGAGTCGAGCAGAAGCTAGCTGATGATCTTGATGAGTTTGGACAGG
genomic sequence(1021) GTTGGTGCTACTCCTCTTCCAGAGTCGAGCAGAAGCTAGCTGATGATCTTGATGAGTTTGGACAGG
HCP7-cDNA-optimized(787) GTTGGAGCTACTCCTCTTCCAGAGTCTAGAAAAGCCTGATTCTCGACGTCGACGTGGACTAGA
```

```
HCP7-cDNA         (1299)
genomic sequence  (1621) CAACGTGTTGCTTGACGTGCATGACGATCCGAGGAGACAACTCCTTTGCTGTTATTGTTGA
HCP7-cDNA-optimized (1299) TACGTGCTCGTTGAGCTTCACCGATTCGAGGACGGCTACGTGCTTGCTTTCGGTTGGTTGGA HCP7-cDNA         (1359)
genomic sequence  (1681) GTTAGGAACGGAAGTGCTTCCTCTTGTTGAAGATTCAGGT------------
HCP7-cDNA-optimized (1359) GTTAGCAACGGAAGTGCTTCCTCTTGCTTTCGAACATTCAGGTACGGTTGGTTATAAAA HCP7-cDNA         (1403)
genomic sequence  (1741) CCCGCTTATATGGAACCTTCTCCACTTAGTTAAGGACCCTAGGT------------
HCP7-cDNA-optimized (1403) CTCTTTTATGATCTGATCTCTCTTGTAGCCACTTTCAACGGTTTTATTCGTTCTTAGCTAATG HCP7-cDNA         (1403)
genomic sequence  (1801)
HCP7-cDNA-optimized (1403) TAATTACCATCGATAAATTTTCAGGTTGGACAATGTACACTAGCTACTACTAGAATATATT HCP7-cDNA         (1437)
genomic sequence  (1861)          TCGTCACATCGCATCGCTAGCACTAGCTACTACTAGCTACATCTT
HCP7-cDNA-optimized (1437) TGTCACGCAGCAGATGCTAGCAGAGTGTCTTAGCAATCATCGGAAGT HCP7-cDNA         (1497)
genomic sequence  (1921) AAATAACAGAGAGCAGAAGCGGGTTATTGATGCCAAAAGCAGAGTACTTTCATTCACACGG
HCP7-cDNA-optimized (1497) TAACAATAGGGAAAGGCTCCTGATGAGCGTGAGTCTATGCTTATGCTTCCTAGGAGTGGGA HCP7-cDNA         (1557)
genomic sequence  (1981) CAGGAACAATCATCATGAGCATACAAGCAGAGTACTTTCATTCACACAGG------TAAGGATTT
HCP7-cDNA-optimized (1557) GCCTAACAACGACGACCCTATAAGGCTAAGTGAGTGGTCTCGATTCACACCGG------

HCP7-cDNA         (1608)
genomic sequence  (2041) GTTACACGACCATCTTCTAATGAATAATTGGTTTGTTACTAGAATAAAGTTTTGAT
HCP7-cDNA-optimized (1608) ------

HCP7-cDNA         (1608)
genomic sequence  (2101) ATGGATTTCTGTTTTATTTACAGGTGAATCACTCAGATGGACTGGTTCGATGCAAC
HCP7-cDNA-optimized (1608) ------GAGATCACCTCACGATGGACTGGTTCGATATCGAAC
```

```
HCP7-cDNA        (2183)                                                                              2760
genomic sequence (2701) TTGACATTTCTCAATCTGTCTGCCTTGCTTCTTTCCGAAAACATTGAAACGTAACA
HCP7-cDNA-optimized (2183) TTGACATTTCTCAATCTGTCTGCCTTGCTTCTTTCCGAAAACATTGAAACGTAAGA
                        TAGACATTAGTCAGTGCGTTAGCCGTTAGCCCTTAGCTCACTCCCGAAGAAGATTGCTAAGGTTAAGA
                        2761                                                                         2820
HCP7-cDNA        (2243) CACTTGAGAAAATCGACACCGAGGAATGCAGCTTATCGAGCCTATACCAAACTCTGTGTT
genomic sequence (2761) CACTTGAGAAAATCGACACCGAGGAATGCAGCTTATCGAGCCTATACCAAACTCTGTGTT
HCP7-cDNA-optimized (2243) CCCTCGAGAAGATCGATACCCGTGCAGTGCCTCACTAGCTCTATCCCTAACTCAGTGGTGC
                        2821                                                                         2880
HCP7-cDNA        (2303) TATTGACTTCTCTACGCCATGTAATATGCGATAGATGCGATAGATAGAGGCTTTATGCATGTGGGAAAAGG
genomic sequence (2821) TATTGACTTCTCTACGCCATGTAATATGCGATAGATGCGATAGATAGAGGCTTTATGCATGTGGGAAAAGG
HCP7-cDNA-optimized (2303) TCCTCACTAGTCTTAGGCACGTTATCGGCATAGGAAGCTTGTGGATGTGGGAGAAGG
                        2881                                                                         2940
HCP7-cDNA        (2363) TCGAGAAGGCGGTTCGAGGACTTCCTGTTGAAGCTCGGCAAAATCTTTCGGCAGGAT
genomic sequence (2881) TCGAGAAGGCGGTTCGAGGACTTCCTGTTGAAGCTCGGCAAAATCTTTCGGCAGGAT
HCP7-cDNA-optimized (2363) TTCAGAAGGCTGTTGCTGGACTTAGAGTTGAGGCTGCCGAAGAGTTTCTCTAGGGAT
                        2941                                                                         3000
HCP7-cDNA        (2423) GGCTTCGACGATTAG
genomic sequence (2941) GGCTTCGACGATTAGGTTCGTGATTCTCTCCCTCCGAGCCCTTAGAAGCATGTTGTATAAA
HCP7-cDNA-optimized (2423) GGCTTCGACGCTAA
                        3001                                                                         3060
HCP7-cDNA        (2437) 
genomic sequence (3001) ATACTTAATTGCTAATCTGTAGCAAAGTCTTGTATAATATTATATTTTATGAGCACACTC
HCP7-cDNA-optimized (2437) 
                        3061                                                                         3120
HCP7-cDNA        (2437) 
genomic sequence (3061) AAGAGTCAAGAGTCAGTGCAAACTTCGTTCTTGCTCTTTCTCCAGAAATTTATCTAACTA
HCP7-cDNA-optimized (2437) 
                        3121                                              3173
HCP7-cDNA        (2437) 
genomic sequence (3121) TAAAATTTCCATTCAAGAATCAGATTTATGTTAGTATCATTCCAGATTCCTTT
HCP7-cDNA-optimized (2437) 
```

Figure 4:

```
   1 ATGGCAGATA TAATCGGCGG CGAAGTTGTG ACGGAGCTCG TGAGGCAGCT
  51 CTATGCGGTT TCTCAAAAAA CCCTCAGATG CAGAGGCATC GCCAAAAATC
 101 TCGCCACCAT GATCGATGGT CTTCAACCAA CGATCAAGGA GATCCAATAC
 151 AGCGGCGTCG AGCTCACACC TCATCGCCAG GCTCAGTTGC GTATGTTCTC
 201 GGAAACCTTA GACAAGTGTA GGAAGCTCAC CGAGAAAGTT CTTAAATCCA
 251 GCCGTTGGAA CATGGTTAGA CAGCTACTCC ATGTTAGGAA AATGGAGAAT
 301 CTTCAGAGTA AAGTGTCTAG CTTTCTCAAC GGTCAATTGT TAGTCCATGT
 351 TCTCGCTGAT GTTCATCATG TTCGAGCCGA TTCTGAATTC CGGTTCGATC
 401 GGATTGATAG GAAGGTTGAT AGTTTGAATG AGAAGCTTGG TTCTATGAAA
 451 CTCAGGGGAA GTGAATCGTT GCGTGAGGCG TTGAAGACGG CCGAGGCTAC
 501 CGTTGAGATG GTGACAACCG ATGGTGCTGA TTTGGGGGTG GGATTGGATT
 551 TGGGAAAGAG GAAGGTGAAG GAGATGTTGT TTAAATCCAT TGATGGGAA
 601 AGACTTATTG GTATCTCTGG GATGAGTGGT TCAGGGAAAA CCACTCTTGC
 651 CAAAGAGCTT GCCCGGGACG AGGAGGTTCG AGGCCACTTT GGGAACAAGG
 701 TTTTGTTTCT GACTGTGTCA CAATCTCCCA ATCTTGAGGA GCTTAGAGCC
 751 CATATATGGG GATTTCTTAC TAGTTATGAG GCTGGGGTTG GTGCTACTCT
 801 TCCAGAATCG AGGAAGCTAG TGATCCTTGA TGATGTTTGG ACAAGGGAAT
 851 CTCTGGACCA GCTGATGTTC GAAAATATTC CTGGAACCAC AACTCTTGTG
 901 GTCTCACGGT CTAAACTCGC AGATTCTAGA GTCACTTATG ATGTAGAGTT
 951 ACTCAATGAA CATGAAGCAA CGGCCCTGTT CTGTCTCTCT GTTTTCAATC
1001 AGAAATTAGT GCCTTCAGGG TTCAGCCAAA GTTTGGTCAA GCAGGTTGTT
1051 GGGGAGTGTA AAGGTCTACC TTTGTCTCTG AAAGTCATTG GTGCTTCATT
1101 GAAAGAACGA CCTGAAAAAT ATTGGGAAGG TGCAGTGGAG AGGCTATCAA
1151 GAGGTGAACC TGCTGATGAA ACTCATGAGA GTAGAGTGTT TGCTCAAATC
1201 GAAGCAACTC TAGAAAATCT TGACCCTAAA ACCAGAGATT GTTTCTTGGT
1251 TCTCGGTGCT TTCCCTGAAG ATAAGAAGAT CCCTCTTGAT GTTCTCATCA
1301 ACGTGTTGGT TGAGTTGCAT GATCTCGAGG ATGCAACTGC TTTTGCTGTT
1351 ATTGTTGATT TAGCAAACAG GAATCTCCTT ACTCTTGTGA AAGATCCAAG
1401 GTTTGGACAT ATGTACACTA GCTACTATGA TATATTTGTC ACGCAGCATG
1451 ATGTTCTAAG AGATGTAGCA CTTCGTCTTA GCAATCATGG GAAAGTAAAT
1501 AACAGAGAGC GGTTATTGAT GCCAAAAAGA GAGTCAATGC TTCCGAGAGA
1551 ATGGGAGAGG AACAATGATG AGCCATACAA AGCCAGAGTA GTTTCCATTC
1601 ACACAGGAGA AATGACTCAG ATGGATTGGT TTGACATGGA ACTCCCTAAG
1651 GCTGAAGTTT TGATACTACA CTTCTCTTCT GACAAGTATG TATTGCCTCC
1701 TTTCATTGCT AAGATGGGCA AGCTTACAGC GCTCGTGATC ATCAACAATG
1751 GTATGTCTCC TGCGCGTCTA CATGACTTCT CCATCTTTAC CAATTTGGCC
1801 AAACTCAAGA GTCTCTGGCT TCAGAGGGTT CATGTCCCTG AACTCTCTAG
1851 CAGTACAGTG CCCTTGCAAA ACCTCCACAA GCTGTCTCTC ATATTCTGCA
1901 AGATCAACAC TAGTCTTGAT CAGACAGAGC TAGACATTGC CCAAATCTTC
1951 CCAAAATTGT CTGATCTTAC AATAGATCAT TGTGATGATC TTCTGGAACT
2001 ACCTTCGACC ATCTGTGGAA TCACCTCTCT CAATTCCATC AGCATAACAA
2051 ATTGTCCCCG CATCAAGGAA TTGCCTAAGA ATCTGAGTAA GCTAAAAGCC
2101 CTTCAGCTTC TGAGGCTATA CGCTTGCCAT GAGCTGAATT CTCTGCCTGT
2151 GGAAATCTGT GAACTGCCAA GACTAAAGTA TGTTGACATT TCTCAATGTG
2201 TCAGCCTGAG TTCTCTTCCG GAAAAGATAG GAAAGGTAAA GACACTTGAG
2251 AAAATCGACA CGAGGGAATG CAGCTTATCG AGCATACCAA ACTCTGTGGT
2301 TTTATTGACT TCTCTACGCC ATGTAATATG CGATAGAGAG GCTTTATGGA
2351 TGTGGGAAAA GGTCCAGAAG GCGGTTGCAG GACTTCGTGT TGAAGCTGCG
2401 GAAAAATCTT TCAGCAGGGA TTGGCTCGAC GATTAG
```

Figure 5:

```
MADIIGGEVVTELVRQLYAVSQKTLRCRGIAKNLATMIDGLQPTIKEIQY  50
SGVELTPHRQAQLRMFSETLDKCRKLTEKVLKSSRWNMVRQLLHVRKMEN 100
LQSKVSSFLNGQLLVHVLADVHHVRADSEFRFDRIDRKVDSLNEKLGSMK 150
LRGSESLREALKTAEATVEMVTTDGADLGVGLDLGKRKVKEMLFKSIDGE 200
RLIGISGMSGSGKTTLAKELARDEEVRGHFGNKVLFLTVSQSPNLEELRA 250
HIWGFLTSYEAGVGATLPESRKLVILDDVWTRESLDQLMFENIPGTTTLV 300
VSRSKLADSRVTYDVELLNEHEATALFCLSVFNQKLVPSGFSQSLVKQVV 350
GECKGLPLSLKVIGASLKERPEKYWEGAVERLSRGEPADETHESRVFAQI 400
EATLENLDPKTRDCFLVLGAFPEDKKIPLDVLINVLVELHDLEDATAFAV 450
IVDLANRNLLTLVKDPRFGHMYTSYYDIFVTQHDVLRDVALRLSNHGKVN 500
NRERLLMPKRESMLPREWERNNDEPYKARVVSIHTGEMTQMDWFDMELPK 550
AEVLILHFSSDKYVLPPFIAKMGKLTALVIINNGMSPARLHDFSIFTNLA 600
KLKSLWLQRVHVPELSSSTVPLQNLHKLSLIFCKINTSLDQTELDIAQIF 650
PKLSDLTIDHCDDLLELPSTICGITSLNSISITNCPRIKELPKNLSKLKA 700
LQLLRLYACHELNSLPVEICELPRLKYVDISQCVSLSSLPEKIGKVKTLE 750
KIDTRECSLSSIPNSVVLLTSLRHVICDREALWMWEKVQKAVAGLRVEAA 800
EKSFSRDWLDD*
```

Figure 6:

```
   1 ATGGCCGATA TAATCGGAGG TGAGGTTGTG ACTGAGCTTG TTAGGCAGCT
  51 CTACGCCGTT AGTCAAAAGA CCCTTAGGTG TAGGGGGATC GCTAAGAACC
 101 TCGCTACTAT GATTGACGGC CTTCAGCCTA CTATCAAAGA AATTCAGTAC
 151 TCAGGCGTGG AACTCACCCC TCACAGACAA GCTCAACTTA GGATGTTTAG
 201 CGAGACTCTC GATAAGTGCC GTAAGCTCAC CGAGAAAGTG CTTAAGAGTT
 251 CTAGGTGGAA TATGGTTAGG CAGCTGCTTC ACGTTAGGAA GATGGAAAAC
 301 CTTCAGTCTA AAGTTAGCAG TTTCCTTAAC GGTCAGCTCC TCGTTCACGT
 351 GCTCGCTGAC GTTCACCACG TTAGGGCTGA CTCAGAGTTT AGGTTCGATA
 401 GGATCGACCG TAAGGTGGAC TCACTTAACG AGAAGCTCGG CTCTATGAAG
 451 CTTAGGGGCT CAGAGTCACT TAGAGAGGCT CTTAAGACTG CTGAGGCTAC
 501 CGTTGAGATG GTTACTACCG ACGGTGCTGA TCTTGGAGTG GGACTTGATC
 551 TCGGTAAGCG TAAGGTGAAA GAGATGCTCT TTAAGTCTAT CGACGGCGAG
 601 AGGCTGATCG GGATTAGTGG AATGTCAGGC TCAGGTAAGA CTACCCTCGC
 651 TAAAGAACTT GCTAGGGACG AAGAGGTTAG GGGCCACTTC GGTAACAAGG
 701 TGTTGTTCCT TACCGTTAGT CAGTCACCTA ACCTCGAGGA ACTTAGGGCT
 751 CATATCTGGG GATTCCTCAC TAGTTACGAG GCTGGTGTTG GAGCTACTCT
 801 TCCAGAGTCT AGAAAGCTCG TGATTCTCGA CGACGTGTGG ACTAGAGAGT
 851 CACTCGATCA GCTGATGTTC GAGAATATCC CAGGTACTAC TACCCTCGTG
 901 GTTAGTAGGT CTAAGTTGGC CGATTCTAGG GTGACCTACG ACGTGGAACT
 951 TCTTAACGAA CACGAGGCTA CCGCTCTGTT CTGCCTTAGT GTGTTTAATC
1001 AGAAACTCGT GCCTAGCGGC TTTAGTCAGA GTTTGGTTAA GCAGGTTGTG
1051 GGCGAGTGTA AGGGACTCCC ACTTAGCCTT AAGGTGATCG GCGCTAGTCT
1101 TAAAGAGAGG CCAGAGAAGT ATTGGGAGGG TGCTGTTGAG AGACTTAGTA
1151 GAGGTGAACC AGCTGACGAG ACTCACGAGT CTAGAGTGTT CGCTCAAATT
1201 GAGGCTACCC TCGAGAACCT CGATCCTAAG ACTAGGGATT GCTTCCTTGT
1251 GCTCGGAGCT TTCCCAGAGG ATAAGAAAAT CCCACTCGAC GTGCTGATTA
1301 ACGTGCTCGT TGAGCTTCAC GATCTCGAGG ACGCTACTGC TTTCGCTGTG
1351 ATTGTGGACC TCGCTAATAG GAACCTTCTC ACTTTAGTTA AGGACCCTAG
1401 GTTCGGTCAC ATGTACACTA GCTACTACGA TATCTTCGTG ACTCAGCACG
1451 ACGTATTGAG GGACGTAGCA CTTAGGCTTA GTAATCACGG TAAGGTTAAC
1501 AATAGGGAAA GGCTCCTGAT GCCTAAGCGT GAGTCTATGC TTCCTAGAGA
1551 GTGGGAGCGT AACAACGACG AACCCTATAA GGCTAGAGTG GTCTCGATTC
1601 ACACCGGCGA GATGACTCAG ATGGACTGGT TCGATATGGA ACTCCCTAAG
1651 GCTGAGGTGC TGATCCTTCA CTTTAGCTCA GATAAGTACG TGCTCCCACC
1701 CTTTATTGCT AAGATGGGAA AGCTTACCGC CCTCGTGATA ATTAACAACG
1751 GGATGTCACC AGCTAGGCTT CACGACTTTC CGATCTTCAC TAACCTCGCT
1801 AAGCTTAAGT CACTCTGGCT TCAGAGGGTT CACGTGCCAG AGCTTAGCAG
1851 TTCTACTGTG CCACTTCAGA ACCTTCACAA GCTTAGCCTG ATCTTCTGTA
1901 AGATTAACAC TAGCCTCGAT CAGACCGAGC TGGATATCGC TCAGATTTTC
1951 CCTAAGCTTA GTGACCTCAC TATCGATCAC TGCGACGACC TTTTGGAGCT
2001 GCCTAGTACT ATTTGCGGGA TCACTAGCCT TAACTCTATT TCGATCACTA
2051 ACTGCCCTAG GATCAAAGAG CTTCCTAAGA ACCTTAGTAA GCTTAAGGCC
2101 CTTCAGCTCC TTAGGCTCTA CGCTTGTCAC GAGCTTAACT CACTCCCAGT
2151 TGAGATCTGC GAGCTGCCTA GGCTTAAGTA CGTAGACATT AGTCAGTGCG
2201 TTAGCCTTAG CTCACTCCCC GAGAAGATTG GTAAGGTTAA GACCCTCGAG
2251 AAGATCGATA CCCGTGAGTG CTCACTTAGC TCTATCCCTA ACTCAGTGGT
2301 GCTCCTCACT AGTCTTAGGC ACGTTATCTG CGATAGGGAA GCTTTGTGGA
2351 TGTGGGAGAA GGTTCAGAAG GCTGTTGCTG GACTTAGAGT TGAGGCTGCC
2401 GAGAAGAGTT TCTCTAGGGA TTGGCTCGAC GACTAA
```

Figure 8:

| SEQ ID NO: | Description of the sequence listing |
|---|---|
| 1 | Nucleotide sequence of HCP7; corresponds to accession no. NM_124099; Arabidopsis thaliana |
| 2 | Amino acid sequence of HCP7; Arabidopsis thaliana |
| 3 | Nucleotide sequence of the HCP7 genomic sequence around the region which codes for HCP7 (At5g04720; accession no. NM_120554), Arabidopsis thaliana |
| 4 | Nucleotide sequence of HCP7; corresponds to accession no. NM_124099; codon optimized; Arabidopsis thaliana |
| 5 | HCP7 forward primer |
| 6 | HCP7 reverse primer |
| 7 | Nucleotide sequence HCP7, variant 1 |
| 8 | Amino acid sequence HCP7, variant 1 |
| 9 | Nucleotide sequence HCP7, variant 2 |
| 10 | Amino acid sequence HCP7, variant 2 |
| 11 | Nucleotide sequence HCP7, variant 3 |
| 12 | Amino acid sequence HCP7, variant 3 |
| 13 | Nucleotide sequence HCP7, variant 4 |
| 14 | Amino acid sequence HCP7, variant 4 |
| 15 | Nucleotide sequence HCP7, variant 5 |
| 16 | Amino acid sequence HCP7, variant 5 |
| 17 | Nucleotide sequence HCP7, variant 6 |
| 18 | Amino acid sequence HCP7, variant 6 |
| 19 | Nucleotide sequence HCP7, variant 7 |
| 20 | Amino acid sequence HCP7, variant 7 |
| 21 | Nucleotide sequence HCP7, variant 8 |
| 22 | Amino acid sequence HCP7, variant 8 |
| 23 | Nucleotide sequence HCP7, variant 9 |
| 24 | Nucleotide sequence HCP7, variant 10 |
| 25 | Nucleotide sequence HCP7, variant 11 |
| 26 | Nucleotide sequence HCP7, variant 12 |
| 27 | Nucleotide sequence HCP7, variant 13 |
| 28 | Nucleotide sequence HCP7, variant 14 |
| 29 | Nucleotide sequence HCP7, variant 15 |
| 30 | Nucleotide sequence HCP7, variant 16 |

FUNGAL RESISTANT PLANTS EXPRESSING HCP7

This application is a National Stage application of International Application No. PCT/EP2014/050387, filed Jan. 10, 2014, which claims priority under 35 U.S.C. § 119 to European Patent Application No. 13152970.3, filed Jan. 29, 2013, the entire contents of which are incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "74751_371_SeqListing.txt" created on Jul. 8, 2015, and is 127,355 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the family Phacopsoraceae, for example soybean rust, in plants, plant parts, and/or plant cells. This is achieved by increasing the expression and/or activity of an HCP7 protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the family Phacopsoraceae, for example soybean rust, and to recombinant expression vectors comprising a sequence that is identical or homologous to a sequence encoding an HCP7 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects).

Another more specific resistance mechanism is based on the presence of so called resistance genes (R-genes). Most R genes belong to the nucleotide-binding site-leucine-rich repeat (NBS-LRR) gene family and function in monitoring the presence of pathogen effector proteins (virulence factors; avirulence factors). After recognizing the pathogen derived proteins a strong defense reaction (mostly accompanied by a programmed cell death) is elicited.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasma membrane of the penetrated mesophyll cell stays intact. Therefore the soybean rust fungus establishes a biotrophic interaction with soybean The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora* The necrotrophic phytopathogenic fungi depend for their nutrition on dead cells of the plants, e.g. species from the genus *Fusarium, Rhizoctonia* or *Mycospaerella* Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races. Therefore there is a strong need to discover R-genes that are derived from non-hosts plants (e.g. *Arabidopsis*) as they are thought to be more durable.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust.

Surprisingly, we found that fungal pathogens, in particular of the family Phacopsoraceae, for example soybean rust, can be controlled by increasing the expression of an HCP7 protein.

The present invention therefore provides a method of increasing resistance against fungal pathogens, preferably against rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust, in transgenic plants, transgenic plant parts, or transgenic plant cells by overexpressing one or more HCP7 nucleic acids.

A further object is to provide transgenic plants resistant against fungal pathogens, preferably rust pathogens (i.e., fungal pathogens of the order Pucciniales), preferably of the family Phacopsoraceae, more preferably against fungal pathogens of the genus *Phacopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous HCP7 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust.

Surprisingly, we found that resistance against fungal pathogens, in particular of the family Phacopsoraceae, for example soybean rust, can be enhanced by increasing the expression of a HCP7 protein.

The present invention therefore provides a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust, in transgenic plants, transgenic plant parts, or transgenic plant cells by overexpressing one or more HCP7 nucleic acids.

A further object is to provide transgenic plants resistant against fungal pathogens, preferably rust pathogens (i.e., fungal pathogens of the order Pucciniales), preferably of the family Phacopsoraceae, more preferably against fungal pathogens of the genus *Phacopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous HCP7 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

FIG. 2 shows the schematic illustration of the plant transformation vector harboring the HCP7 cDNA under control of the parsley ubiquitine promoter.

Figure 3:
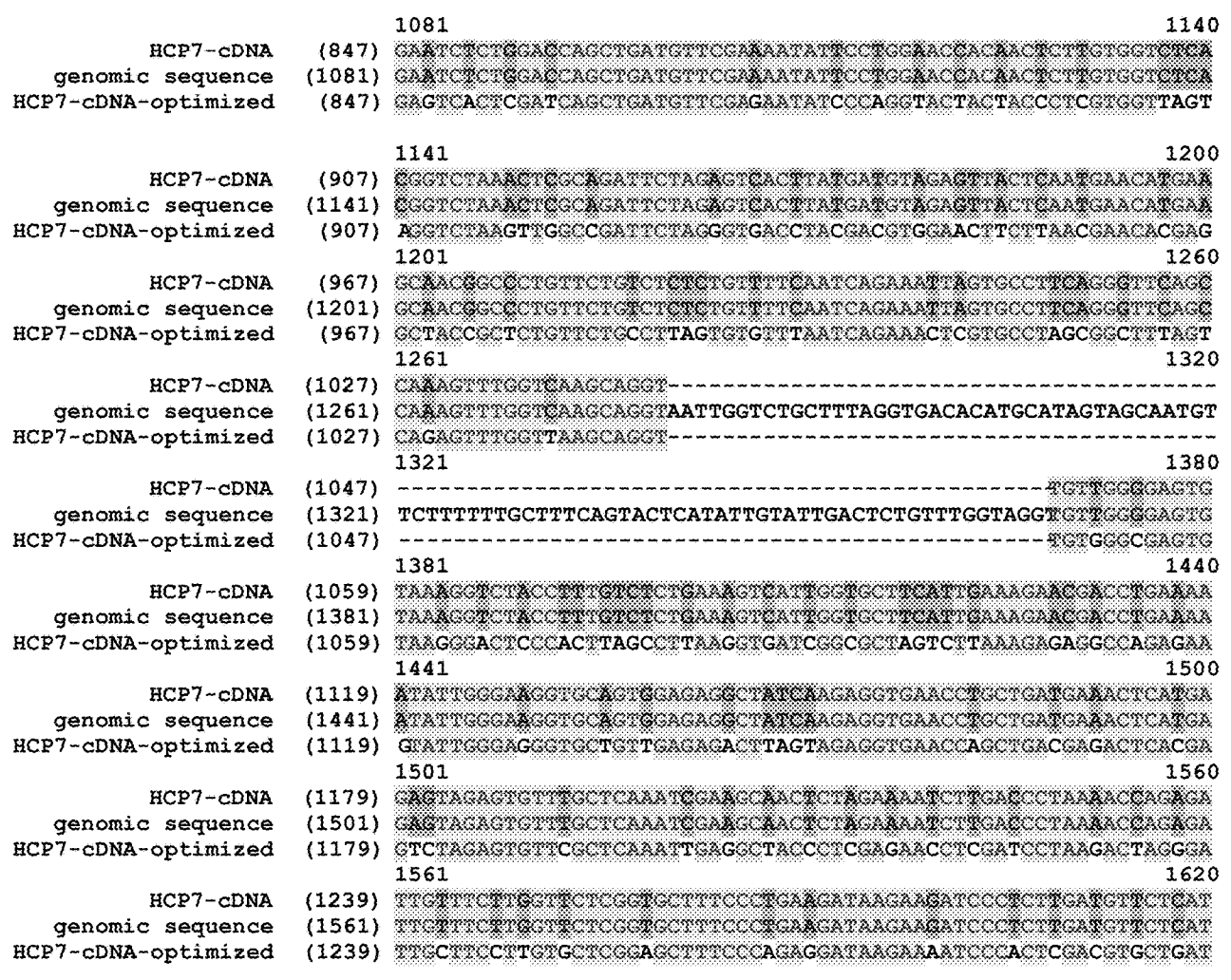
Figure 3:
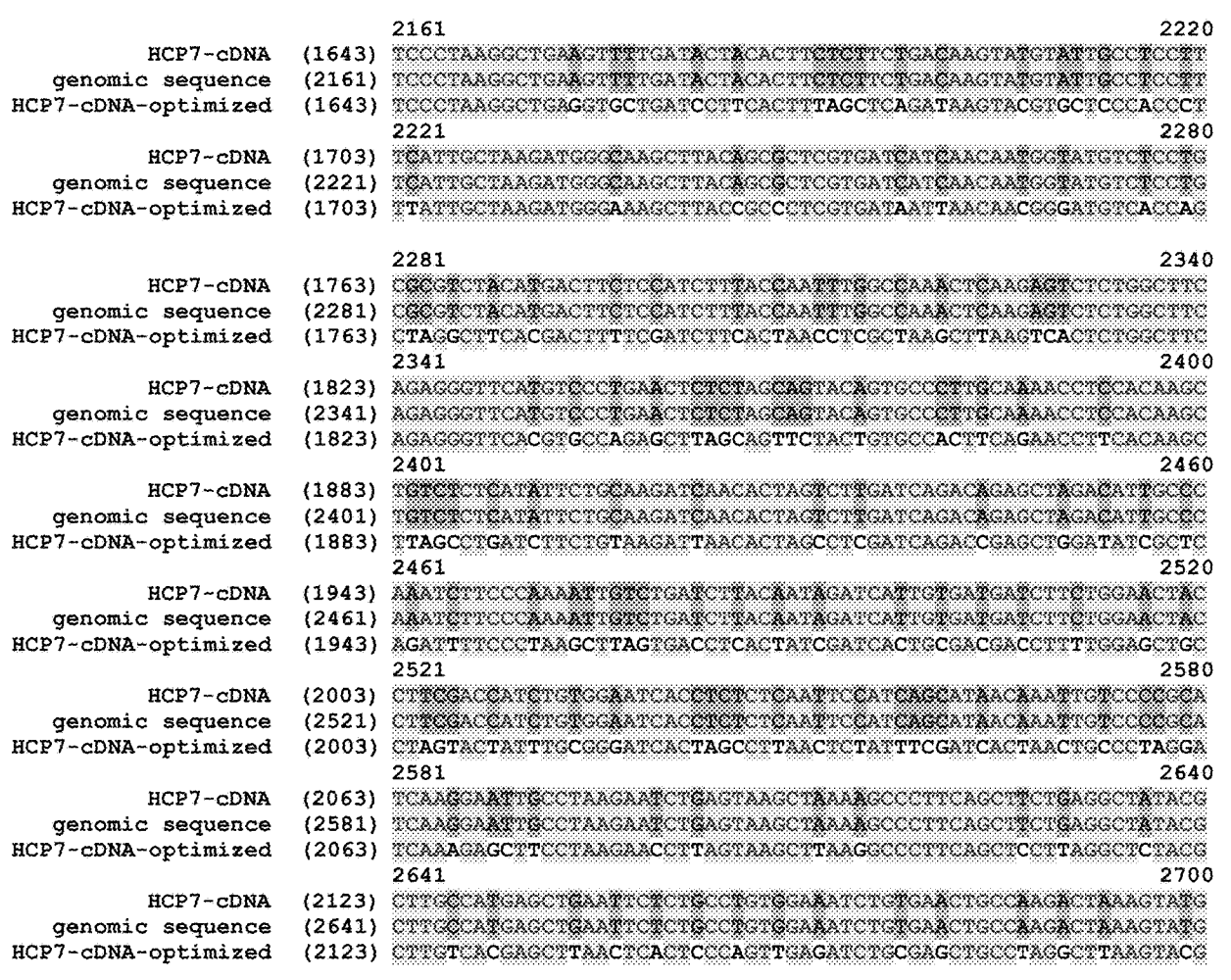

FIG. 3 shows the alignment of the *Arabidopsis* HCP7 genomic sequence (accession No NM_120554, At5g04720, SEQ ID NO: 3) and the HCP7 sequence (derived from the genomic sequence At5g04720; accession No NM_124099, HCP7-cDNA, SEQ ID NO: 1) and the sequence of the codon-optimized version of HCP7 (HCP7-cDNA-optimized, SEQ ID NO: 4) that has a codon-optimized sequence that is optimal for expression in soybean (codes for the same protein sequence as HCP7-cDNA and which is given in SEQ ID NO: 2).

FIG. 4 shows the full-length-sequence of the HCP7 gene from *Arabidopsis thaliana* having SEQ ID NO: 1.

FIG. 5 shows the sequence of the HCP7 protein (SEQ ID NO: 2).

FIG. 6 shows the nucleotide sequence of the optimized version of HCP7, which is codon optimized for optimal expression in soybean (SEQ ID NO: 4).

FIG. 7 shows the result of the scoring of 36 transgenic soy plants (derived from 4 independent events, 7-10 plants per event) expressing the HCP7 overexpression vector construct. $T_1$ soybean plants expressing HCP7 protein were inoculated with spores of *Phakopsora pachyrhizi* The evaluation of the diseased leaf area on all leaves was performed 14 days after inoculation. The average of the percentage of the leaf area showing fungal colonies or strong yellowing/browning on all leaves was considered as diseased leaf area. At all 36 soybean $T_1$ plants expressing HCP7 (expression checked by RT-PCR) were evaluated in parallel to non-transgenic control plants. The average of the diseased leaf area is shown in FIG. 7. Overexpression of HCP7 significantly (*: $p<0.05$) reduces the diseased leaf area in comparison to non-transgenic control plants by 21.1%.

FIG. 8 contains a brief description of the sequences of the sequence listing.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc. (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar functional activity as the unmodified protein coded by the unmodified nucleic acid from which they are derived. In particular, homologues of a nucleic acid may encompass substitutions on the basis of the degenerative amino acid code.

The terms "identity", "homology" and "similarity" are used herein interchangeably. "Identity" or "homology" or "similarity" between two nucleic acids sequences or amino acid sequences refers in each case over the entire length of the respective HCP7 nucleic acid sequence or HCP7 amino acid sequence.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The sequence identity may also be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:
Multiple alignment parameter:
Gap opening penalty 10
Gap extension penalty 10
Gap separation penalty range 8
Gap separation penalty off
% identity for alignment delay 40
Residue specific gaps off
Hydrophilic residue gap off
Transition weighing 0
Pairwise alignment parameter:
FAST algorithm on
K-tuple size 1
Gap penalty 3
Window size 5
Number of best diagonals 5

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings
DNA Gap Open Penalty 15.0 DNA Gap Extension Penalty 6.66
DNA Matrix Identity
Protein Gap Open Penalty 10.0
Protein Gap Extension Penalty 0.2
Protein matrix Gonnet
Protein/DNA ENDGAP −1
Protein/DNA GAPDIST 4

Sequence identity between the nucleic acid or protein useful according to the present invention and the HCP7 nucleic acids or HCP7 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Taylor W. R. (1986) The classification of amino acid conservation J Theor Biol., 119:205-18 and Table 1 below).

TABLE 1

Examples of conserved amino acid substitutions

| Residue | Conservative Substitutions | Residue | Conservative Substitutions |
|---|---|---|---|
| A | G, V, I, L, M | L | M, I, V, A, G |
| C | S, T | N | Q |
| E | D | Q | N |
| D | E | P | |
| G | A, V, I, L, M | S | T, C |
| F | Y, W | R | K, H |
| I | V, A, G, L, M | T | S, C |
| H | R, K | W | Y, F |
| K | R, H | V | I, A, G, L, M |
| M | L, I, V, A, G | Y | F, W |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by non-coding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phacopsoracea, in particular *Phakopsora pachyrhizi* and *Phakopsora meibomiae*—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous HCP7 nucleic acid, functional fragments thereof and/or an exogenous nucleic acid capable of hybridizing with an HCP7 nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% G+C)$, when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole HCP7 nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous HCP7 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous HCP7 nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more HCP7 nucleic acids, all those constructions brought about by man by genetechnological methods in which either (a) the sequences of the HCP7 nucleic acids or a part thereof, or (b) genetic control sequence(s) which is operably linked with the HCP7 nucleic acid sequence according to the invention, for example a promoter, or (c) a) and b)

are not located in their natural genetic environment or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

For instance, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

For instance, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous HCP7 nucleic acid, recombinant construct, vector or expression cassette including one or more HCP7 nucleic acids is integrated into the genome by means of genetechnology.

A "wild type" plant, "wild type" plant part, or "wild type" plant cell means that said plant, plant part, or plant cell does not express exogenous HCP7 nucleic acid or exogenous HCP7 protein.

Natural locus means the location on a specific chromosome, preferably the location between certain genes, more preferably the same sequence background as in the original plant which is transformed.

Preferably, the transgenic plant, plant cell or tissue thereof expresses the HCP7 nucleic acids, HCP7 constructs or HCP7 expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the HCP7 nucleic acids has an identity as defined above over a length of at least 20%, at least 30%, at least 50%, at least 75%, at least 90% of the nucleotides of the respective HCP7 nucleic acid.

The term "splice variant" as used herein encompasses variants of a nucleic acid sequence in which selected introns and/or exons have been excised, replaced, displaced or added, or in which introns have been shortened or lengthened. Thus, a splice variant can have one or more or even all introns removed or added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the HCP7 nucleotide sequence as defined by SEQ ID NO: 1 or 4.

The term "increased activity" or "enhanced activity" as used herein means any protein having increased activity and which provides an increased fungal resistance compared with the wildtype plant merely expressing the respective endogenous HCP7 nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

HCP7 Nucleic Acids

Figure 1:
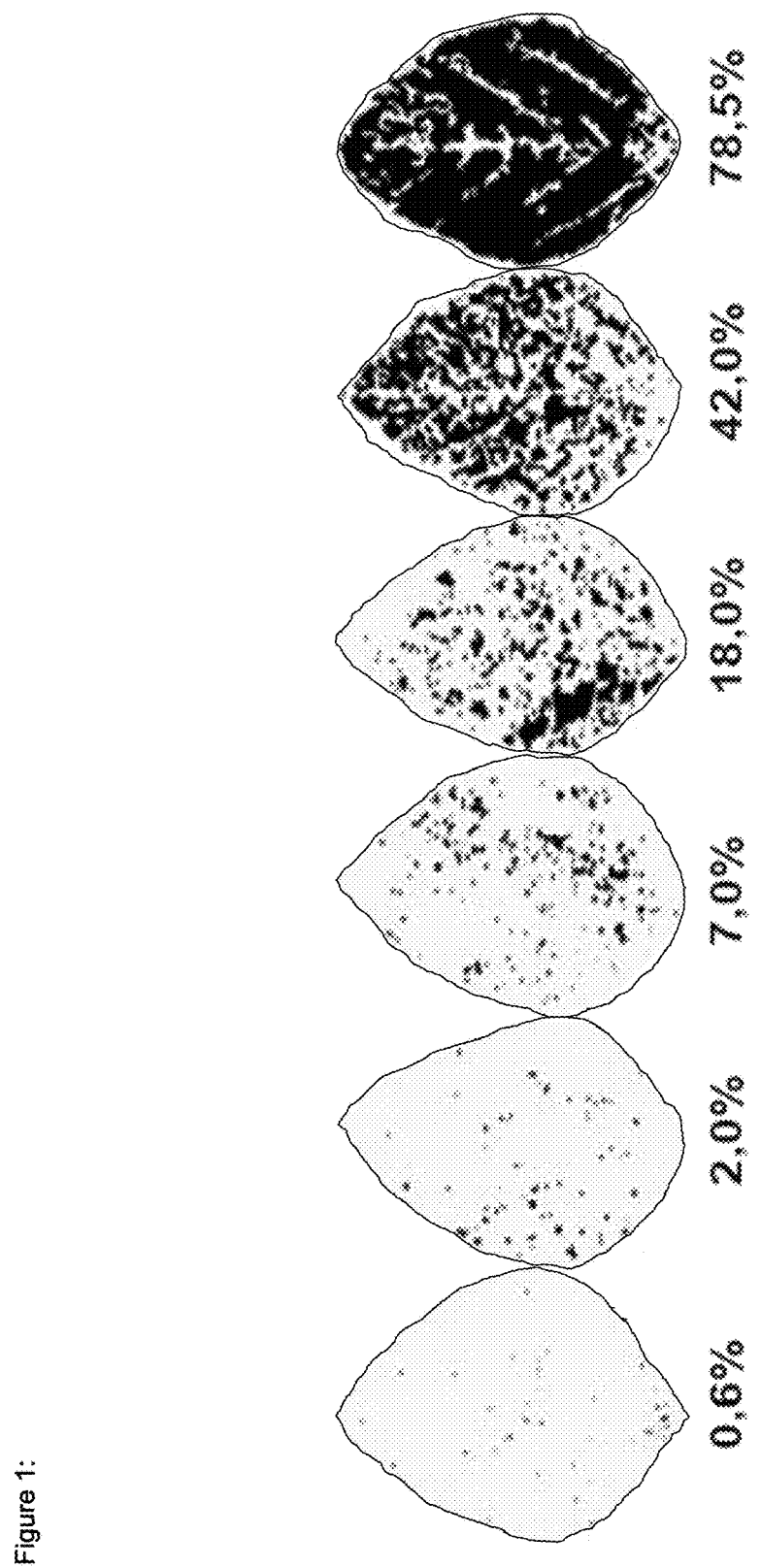

The HCP7 nucleic acid to be overexpressed in order to achieve increased resistance to fungal pathogens, e.g., of the family Phacopsoraceae, for example soybean rust, is preferably a nucleic acid coding for an HCP7 protein, and is preferably as defined by SEQ ID NO: 4, 1, 3, 7, 9, 11, 13, 15, 17, 19, 21, 23, 24, 25, 26, 27, 28, 29, or 30, or a fragment, homolog, derivative, orthologue or paralogue thereof, or a splice variant thereof. Preferably, the nucleic acid coding for an HCP7 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30, or is a functional fragment thereof, or a splice variant thereof. Most preferred is at least 90% identity, at least 92%, at least 95%, at least 97% identity, more preferred is at least 98% or at least 99% identity with SEQ ID NO: 4, 1, 3, 7, 9, 11, 13, 15, 17, 19, 21, 23, 24, 25, 26, 27, 28, 29, or 30.

Preferably, the HCP7 nucleic acid to be overexpressed in order to achieve increased resistance to fungal pathogens, e.g., of the family Phacopsoraceae, for example soybean rust, is preferably a nucleic acid coding for an HCP7 protein, and is preferably as defined by SEQ ID NO: 4, or a fragment, homolog, derivative, orthologue or paralogue thereof, or a splice variant thereof. Preferably, the nucleic acid coding for an HCP7 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 4 or is a functional fragment thereof, or a splice variant thereof. Most preferred is at least 90% identity, at least 92%, at least 95%, at least 97% identity, more preferred is at least 98% or at least 99% identity with SEQ ID NO: 4.

More preferably, the HCP7 nucleic acid to be overexpressed in order to achieve increased resistance to fungal pathogens, e.g., of the family Phacopsoraceae, for example soybean rust, is preferably a nucleic acid coding for an HCP7 protein, and is preferably as defined by SEQ ID NO: 1, or a fragment, homolog, derivative, orthologue or paralogue thereof, or a splice variant thereof. Preferably, the nucleic acid coding for an HCP7 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 1 or is a functional fragment thereof, or a splice variant thereof. Most preferred is at least 92%, at least 95%, at least 97% identity, more preferred is at least 98% or at least 99% identity with SEQ ID NO: 1.

SEQ ID NO: 4 corresponds to SEQ ID NO: 1, wherein the codon usage has been optimized for expression in soy.

Preferably the HCP7 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, 1, 3, 7, 9, 11, 13, 15, 17, 19, 21, 23, 24, 25, 26, 27, 28, 29, or 30, or a functional fragment, derivative, orthologue, or paralogue thereof, or a splice variant thereof, wherein overexpression of the sequence confers enhanced fungal resistance in the plant relative to a control plant;

(ii) a nucleic acid encoding a HCP7 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 8, 10, 12, 14, 16, 18, 20, or 22, or a functional fragment, derivative, orthologue, or paralogue thereof, wherein overexpression of the sequence confers enhanced fungal resistance in the plant relative to a control plant; preferably the HCP7 protein has essentially the same biological activity as an HCP7 protein encoded by SEQ ID NO: 4, 1, or 3; preferably the HCP7 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same HCP7 protein as the HCP7 nucleic acids of (i) to (iii) above, but differing from the HCP7 nucleic acids of (i) to (iii) above due to the degeneracy of the genetic code.

Preferably the HCP7 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof, wherein overexpression of the sequence confers enhanced fungal resistance in the plant relative to a control plant;

(ii) a nucleic acid encoding a HCP7 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof, wherein overexpression of the sequence confers enhanced fungal resistance in the plant relative to a control plant; preferably the HCP7 protein has essentially the same biological activity as an HCP7 protein encoded by SEQ ID NO: 1, preferably the HCP7 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same HCP7 protein as the HCP7 nucleic acids of (i) to (iii) above, but differing from the HCP7 nucleic acids of (i) to (iii) above due to the degeneracy of the genetic code.

Preferably the HCP7 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, or a functional fragment, derivative, orthologue, or paralogue thereof, or a splice variant thereof;

(ii) a nucleic acid encoding a HCP7 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the HCP7 protein has essentially the same biological activity as an HCP7 protein encoded by SEQ ID NO: 4, preferably the HCP7 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same HCP7 protein as the HCP7 nucleic acids of (i) to (iii) above, but differing from the HCP7 nucleic acids of (i) to (iii) above due to the degeneracy of the genetic code.

Percentages of identity of a nucleic acid are indicated with reference to the entire nucleotide region given in a sequence specifically disclosed herein.

Preferably the portion of the HCP7 nucleic acid is about 1000-1500, about 1500-2000, about 2000-2250, about 2250-2500, about 2500-2700, about 2700-3000, or about 3000-3173 nucleotides, preferably consecutive nucleotides, preferably counted from the 5' or 3' end of the nucleic acid, in length, of the nucleic acid sequences given in SEQ ID NO: 4, 1, 3, 7, 9, 11, 13, 15, 17, 19, 21, 23, 24, 25, 26, 27, 28, 29, or 30.

Preferably, the HCP7 nucleic acid comprises at least about 1000, at least about 1500, at least about 2000, at least about 2250, at least about 2500, at least about 2750, at least about 2800, at least about 2900, at least about 3000, or at least about 3100 nucleotides, preferably continuous nucleotides, preferably counted from the 5' or 3' end of the nucleic acid or up to the full length of the nucleic acid sequence set out in SEQ ID NO: 4, 1, 3, 7, 9, 11, 13, 15, 17, 19, 21, 23, 24, 25, 26, 27, 28, 29, or 30.

Preferably, the HCP7 nucleic acid comprises at least about 1000, at least about 1500, at least about 1600, at least about 1700, at least about 1800, at least about 1900, at least about 2000, at least about 2100, at least about 2200, at least about 2300, or at least about 2400 nucleotides, preferably continuous nucleotides, preferably counted from the 5' or 3' end of the nucleic acid or up to the full length of the nucleic acid sequence set out in SEQ ID NO: 1, 4, 7, 9, 11, 13, 15, 17, 19, 21, 23, 24, 25, 26, 27, 28, 29, or 30.

Preferably the portion of the HCP7 nucleic acid is about 1000-1500, about 1500-1600, about 1600-1700, about 1700-1800, about 1800-1900, about 1900-2000, about 2100-2200, about 2200-2300, about 2300-2400, or at least about 2400-2436 nucleotides, preferably consecutive nucleotides, preferably counted from the 5' or 3' end of the nucleic acid, in length, of the nucleic acid sequences given in SEQ ID NO: 1, 4, 7, 9, 11, 13, 15, 17, 19, 21, 23, 24, 25, 26, 27, 28, 29, or 30.

Preferably, the HCP7 nucleic acid comprises at least about 1000, at least about 1500, at least about 1600, at least about 1700, at least about 1800, at least about 1900, at least about 2000, at least about 2100, at least about 2200, at least about 2300, or at least about 2400 nucleotides, preferably continuous nucleotides, preferably counted from the 5' or 3' end of the nucleic acid or up to the full length of the nucleic acid sequence set out in SEQ ID NO: 4.

Preferably the portion of the HCP7 nucleic acid is about 1000-1500, about 1500-1600, about 1600-1700, about 1700-1800, about 1800-1900, about 1900-2000, about 2100-2200, about 2200-2300, about 2300-2400, or at least about 2400-2436 nucleotides, preferably consecutive nucleotides, preferably counted from the 5' or 3' end of the nucleic acid, in length, of the nucleic acid sequences given in SEQ ID NO: 4.

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix.

Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The HCP7 nucleic acids described herein are useful in the constructs, methods, plants, harvestable parts and products of the invention.

HCP7 Proteins

The HCP7 protein is preferably defined by SEQ ID NO: 2, 8, 10, 12, 14, 16, 18, 20, or 22, or a fragment, homolog, derivative, orthologue or paralogue thereof. Preferably, the HCP7 protein of the present invention is encoded by a nucleic acid, which has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30, or a functional fragment thereof. More preferably, the HCP7 protein of the present invention has at least 60%, preferably at least 70% sequence identity, at least 80%, at least 90%, at least 92%, at least 95%, at least 97%, at least 98%, at least 99% sequence identity, or even 100% sequence identity with SEQ ID NO: 2, 8, 10, 12, 14, 16, 18, 20, or 22, or is a functional fragment thereof, an orthologue or a paralogue thereof. Most preferred is at least 90% identity, at least 92%, at least 95%, at least 97% identity, more preferred is at least 98% or at least 99% identity with SEQ ID NO: 2, 8, 10, 12, 14, 16, 18, 20, or 22.

More preferably, the HCP7 protein of the present invention has at least 60%, preferably at least 70% sequence identity, at least 80%, at least 90%, at least 92%, at least 95%, at least 97%, at least 98%, at least 99% sequence identity, or even 100% sequence identity with SEQ ID NO: 2 or is a functional fragment thereof, an orthologue or a paralogue thereof.

Preferably, the HCP7 protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 8, 10, 12, 14, 16, 18, 20, or 22, or a functional fragment, derivative, orthologue, or paralogue thereof, wherein overexpression of the sequence confers enhanced fungal resistance in the plant relative to a control plant; preferably the HCP7 protein has essentially the same biological activity as an HCP7 protein encoded by SEQ ID NO: 4, 1, or 3; preferably the HCP7 protein confers enhanced fungal resistance relative to control plants; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, 1, 3, 7, 9, 11, 13, 15, 17, 19, 21, 23, 24, 25, 26, 27, 28, 29, or 30, or a functional fragment, derivative, orthologue, or paralogue thereof, or a splice variant thereof, wherein overexpression of the sequence confers enhanced fungal resistance in the plant relative to a control plant; preferably the HCP7 protein confers enhanced fungal resistance relative to control plants.

Preferably, the HCP7 protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof, wherein overexpression of the sequence confers enhanced fungal resistance in the plant relative to a control plant; preferably the HCP7 protein has essentially the same biological activity as an HCP7 protein encoded by SEQ ID NO: 1; preferably the HCP7 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 4, or a functional fragment, derivative, orthologue, or paralogue thereof, or a splice variant thereof, wherein overexpression of the sequence confers enhanced fungal resistance in the plant relative to a control plant; preferably the HCP7 protein confers enhanced fungal resistance relative to control plants.

A preferred derivative of a HCP7 protein is a HCP7 protein consisting of or comprising an amino acid sequence selected from the group consisting of:
an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence represented by SEQ ID NO: 2, 8, 10, 12, 14, 16, 18, 20, or 22, wherein the non-identical amino acid residues are conservative amino acid substitutions, preferably as shown in Table 1, of the corresponding amino acid residue of SEQ ID NO: 2, 8, 10, 12, 14, 16, 18, 20, or 22; preferably the HCP7 protein has essentially the same biological activity as SEQ ID NO: 2, or as a HCP7 protein encoded by SEQ ID NO: 4, 1, or 3; preferably the HCP7 protein confers enhanced fungal resistance relative to control plants.

Preferably, the HCP7 protein consists of or comprises an amino acid sequence represented by SEQ ID NO: 2, 8, 10, 12, 14, 16, 18, 20, or 22 with one or more conservative amino acid substitutions, preferably as shown in Table 1, of the corresponding amino acid residues of SEQ ID NO: 2, 8, 10, 12, 14, 16, 18, 20, or 22. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 amino acid residues of SEQ ID NO: 2, 8, 10, 12, 14, 16, 18, 20, or 22 are conservative amino acid substitutions, preferably as shown in Table 1, of the corresponding amino acid residue of SEQ ID NO: 2, 8, 10, 12, 14, 16, 18, 20, or 22.

More preferably, the HCP7 protein consists of or comprises an amino acid sequence having at least 80%, at least 85%, at least 90%, at least 95%, at least 98% or at least 99% sequence identity with an amino acid sequence as represented by SEQ ID NO: 2, 8, 10, 12, 14, 16, 18, 20, or 22, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, or at least 120 of the non-identical amino acid residues, or wherein 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 or even all of the non-identical amino acid residues are conservative amino acid substitutions, preferably as shown in Table 1, of the corresponding amino acid residue of SEQ ID NO: 2, 8, 10, 12, 14, 16, 18, 20, or 22.

Percentages of identity of a polypeptide or protein are indicated with reference to the entire amino acid sequence specifically disclosed herein.

Preferably, the HCP7 protein comprises at least about 500, at least about 550, at least about 600, at least about 650, at least about 700, at least about 750, at least about 800, or at least about 810 amino acid residues, preferably continuous amino acid residues, preferably counted from the N-terminus or the C-terminus of the amino acid sequence, or up to the full length of the amino acid sequence set out in SEQ ID NO: 2, 8, 10, 12, 14, 16, 18, 20, or 22.

Preferably, the HCP7 polypeptide comprises about 500-550, about 550-600, about 650-700, about 750-760, about 760-770, about 770-780, about 780-790, about 790-800, or about 800-811 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 2, 8, 10, 12, 14, 16, 18, 20, or 22.

The HCP7 proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phacopsoracea, for example soy bean rust, in a plant, plant part, or plant cell by increasing the expression of an HCP7 protein or a functional fragment, orthologue, paralogue or homologue thereof in comparison to wild-type plants, wild-type plant parts or wild-type plant cells.

The present invention also provides a method for increasing resistance to fungal pathogens, in particular a heminecrotrophic pathogen, in particular to rust pathogens (i.e., fungal pathogens of the order Pucciniales), preferably fungal pathogens of the family Phacopsoraceae, preferably against fungal pathogens of the genus *Phacopsora*, most preferably against *Phakopsora pachyrhizi* and *Phakopsora meibomiae*, also known as soy bean rust in plants or plant cells, wherein in comparison to wild type plants, wild type plant parts, or wild type plant cells an HCP7 protein is overexpressed.

The present invention further provides a method for increasing resistance to fungal pathogens of the genus *Phacopsora*, most preferably against *Phakopsora pachyrhizi* and *Phakopsora meibomiae*, also known as soy bean rust in plants or plant cells by overexpression of an HCP7 protein.

In preferred embodiments, the protein amount and/or function of the HCP7 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the HCP7 nucleic acid.

In one embodiment of the invention, the HCP7 protein is encoded by a nucleic acid comprising (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 4, 1, 3, 7, 9, 11, 13, 15, 17, 19, 21, 23, 24, 25, 26, 27, 28, 29, or 30, a functional fragment thereof, or an orthologue or a paralogue thereof, or a splice variant thereof; or by (ii) an exogenous nucleic acid encoding a protein comprising an amino acid sequence having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 8, 10, 12, 14, 16, 18, 20, or 22, a functional fragment thereof, an orthologue or a paralogue thereof, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; or by (iv) an exogenous nucleic acid encoding the same HCP7 protein as the nucleic acids of (i) to (iii) above, but differing from the nucleic acids of (i) to (iii) above due to the degeneracy of the genetic code.

A method for increasing fungal resistance, preferably resistance to Phacopsoracea, for example soy bean rust, in a plant, plant part, or plant cell, by increasing the expression of an HCP7 protein or a functional fragment, orthologue, paralogue or homologue thereof, or a splice variant thereof, wherein the HCP7 protein is encoded by a nucleic acid comprising (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30, or a functional fragment thereof, an orthologue or a paralogue thereof, or a splice variant thereof;

(ii) an exogenous nucleic acid encoding a protein comprising an amino acid sequence having at least 60%, preferably at least 70% sequence identity, at least 80%, at least 90%, at least 95%, at least 98%, at least 99% sequence identity, or even 100% sequence identity with SEQ ID NO: 2, 8, 10, 12, 14, 16, 18, 20, or 22, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP7 protein as the nucleic acids of (i) to (iii) above, but differing from the nucleic acids of (i) to (iii) above due to the degeneracy of the genetic code;

is a further embodiment of the invention.

A method for increasing fungal resistance, preferably resistance to Phacopsoracea, for example soy bean rust, in a plant, plant part, or plant cell, by increasing the expression of an HCP7 protein or a functional fragment, orthologue, paralogue or homologue thereof, or a splice variant thereof, wherein the HCP7 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP7 protein as the nucleic acids of (i) to (iii) above, but differing from the nucleic acids of (i) to (iii) above due to the degeneracy of the genetic code is a further embodiment of the invention.

A method for increasing fungal resistance, preferably resistance to Phacopsoracea, for example soy bean rust, in a plant, plant part, or plant cell, by increasing the expression of an HCP7 protein or a functional fragment, orthologue, paralogue or homologue thereof, or a splice variant thereof, wherein the HCP7 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP7 protein as the nucleic acids of (i) to (iii) above, but differing from the nucleic acids of (i) to (iii) above due to the degeneracy of the genetic code is a further embodiment of the invention.

In a further method of the invention, the method comprises the steps of (a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30, or a functional fragment thereof, or an orthologue or a paralogue thereof, or a splice variant thereof;
  (ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 2, 8, 10, 12, 14, 16, 18, 20, or 22, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
  (iv) a nucleic acid encoding the same HCP7 polypeptide as the nucleic acids of (i) to (iii) above, but differing from the nucleic acids of (i) to (iii) above due to the degeneracy of the genetic code,
in functional linkage with a promoter;
(b) regenerating the plant from the plant cell; and
(c) expressing said nucleic acid, optionally wherein the nucleic acid which codes for an HCP7 protein is expressed in an amount and for a period sufficient to generate or to increase soybean rust resistance in said plant.

Preferably, the method comprises the steps of (a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
  (iv) a nucleic acid encoding the same HCP7 polypeptide as the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for an HCP7 protein is expressed in an amount and for a period sufficient to generate or to increase soybean rust resistance in said plant.

Preferably, the method comprises the steps of (a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 4, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
(iv) a nucleic acid encoding the same HCP7 polypeptide as the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for an HCP7 protein is expressed in an amount and for a period sufficient to generate or to increase soybean rust resistance in said plant.

Preferably, the promoter is a rust induced and/or mesophyll-specific promoter, preferably the rust induced mesophyll specific promoter 820.

Preferably, the method for increasing fungal resistance, preferably resistance to Phacopsoracea, for example soy bean rust, in a plant, plant part, or plant cell further comprises the step of selecting a transgenic plant expressing
(i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30, or a functional fragment thereof, or an orthologue or a paralogue thereof, or a splice variant thereof;
(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 8, 10, 12, 14, 16, 18, 20, or 22, a functional fragment thereof, an orthologue or a paralogue thereof; preferably the encoded protein confers enhanced fungal resistance relative to control plants;
(iii) an exogenous nucleic acid capable of hybridizing under stringent conditions a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
(iv) an exogenous nucleic acid encoding the same HCP7 polypeptide as the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of an HCP7 protein, wherein the HCP7 protein is encoded by a nucleic acid comprising
(i) an exogenous nucleic acid having at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30;
(ii) an exogenous nucleic acid encoding a protein comprising an amino acid sequence having at least 80%, at least 90%, at least 95%, at least 98%, at least 99% sequence identity, or even 100% sequence identity with SEQ ID NO: 2, 8, 10, 12, 14, 16, 18, 20, or 22; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
(iv) an exogenous nucleic acid encoding the same HCP7 protein as the nucleic acids of (i) to (iii) above, but differing from the nucleic acids of (i) to (iii) above due to the degeneracy of the genetic code, wherein increasing the expression of the HCP7 protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of an HCP7 protein, wherein the HCP7 protein is encoded by a nucleic acid comprising
(i) an exogenous nucleic acid having at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30;
(ii) an exogenous nucleic acid encoding a protein comprising an amino acid sequence having at least 80%, at least 90%, at least 95%, at least 98%, at least 99% sequence identity, or even 100% sequence identity with SEQ ID NO: 2, 8, 10, 12, 14, 16, 18, 20, or 22; preferably the encoded protein confers enhanced fungal resistance relative to control plants; or
(iii) an exogenous nucleic acid encoding the same HCP7 protein as the nucleic acids of (i) to (ii) above, but differing from the nucleic acids of (i) to (ii) above due to the degeneracy of the genetic code, wherein increasing the expression of the HCP7 protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
| --- | --- |
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi, P. meibomiae* |
| Rust (tropical corn) | *Physopella pallescens, P. zeae = Angiopsora zeae* |

TABLE 3

Diseases caused by necrotrophic and/or hemibiotrophic fungi and Oomycetes

| Disease | Pathogen |
| --- | --- |
| Plume blotch | *Septoria (Stagonospora) nodorum* |
| Leaf blotch | *Septoria tritici* |
| Ear *fusarioses* | *Fusarium* spp. |
| Late blight | *Phytophthora infestans* |
| *Anthrocnose* leaf blight | *Colletotrichum graminicola* (teleomorph: *Glomerella graminicola* Politis); *Glomerella tucumanensis* (anamorph: *Glomerella falcatum* Went) |
| *Anthracnose* stalk rot | |
| *Curvularia* leaf spot | *Curvularia clavata, C. eragrostidis, = C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| *Didymella* leaf spot | *Didymella exitalis* |
| *Diplodia* leaf spot or streak | *Stenocarpella macrospora = Diplodialeaf macrospora* |
| Brown stripe downy mildew | *Sclerophthora rayssiae var. zeae* |
| Crazy top downy mildew | *Sclerophthora macrospora = Sclerospora macrospora* |
| Green ear downy mildew (*graminicola* downy mildew) | *Sclerospora graminicola* |
| Leaf spots, minor | *Alternaria alternata, Ascochyta maydis, A. tritici, A. zeicola, Bipolaris victoriae =Helminthosporium victoriae* (teleomorph: *Cochliobolus victoriae), C. sativus* (anamorph: *Bipolaris sorokiniana = H. sorokinianum = H. sativum), Epicoccum nigrum, Exserohilum prolatum = Drechslera prolata* (teleomorph: *Setosphaeria prolata) Graphium penicillioides, Leptosphaeria maydis, Leptothyrium zeae, Ophiosphaerella herpotricha*, (anamorph: *Scolecosporiella* sp.), *Paraphaeosphaeria michotii, Phoma* sp., *Septoria zeae, S. zeicola, S. zeina* |
| Northern corn leaf blight (white blast, crown stalk rot, stripe) | *Setosphaeria turcica* (anamorph: *Exserohilum turcicum = Helminthosporium turcicum*) |
| Northern corn leaf spot *Helminthosporium* ear rot (race 1) | *Cochliobolus carbonum* (anamorph: *Bipolaris zeicola = Helminthosporium carbonum*) |
| *Phaeosphaeria* leaf spot | *Phaeosphaeria maydis = Sphaerulina maydis* |

TABLE 3-continued

Diseases caused by necrotrophic and/or hemibiotrophic fungi and Oomycetes

| Disease | Pathogen |
| --- | --- |
| *Rostratum* leaf spot (*Helminthosporium* leaf disease, ear and stalk rot) | *Setosphaeria rostrata*, (anamorph: *xserohilum rostratum = Helminthosporium rostratum*) |
| Java downy mildew | *Peronosclerospora maydis = Sclerospora maydis* |
| Philippine downy mildew | *Peronosclerospora philippinensis = Sclerospora philippinensis* |
| *Sorghum* downy mildew | *Peronosclerospora sorghi = Sclerospora sorghi* |
| *Spontaneum* downy mildew | *Peronosclerospora spontanea = Sclerospora spontanea* |
| Sugarcane downy mildew | *Peronosclerospora sacchari = Sclerospora sacchari* |
| *Sclerotium* ear rot (southern blight) | *Sclerotium rolfsii* Sacc. (teleomorph: *Athelia rolfsii*) |
| Seed rot-seedling blight | *Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae* (anamorph: *F. graminearum), Macrophomina phaseolina, Penicillium* spp., *Phomopsis* sp., *Pythium* spp., *Rhizoctonia solani, R. zeae, Sclerotium rolfsii, Spicaria* sp. |
| *Selenophoma* leaf spot | *Selenophoma* sp. |
| Yellow leaf blight | *Ascochyta ischaemi, Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea*, *Polymyxa graminis*, Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium* wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, more preferably heminecrotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales (rust), previously known as Uredinales, among which in particular the Melompsoraceae. Preferred are Phakopsoraceae, more preferably *Phakopsora*. Especially preferred are *Phakopsora pachyrhizi* and/or *Phakopsora meibomiae*.

Also preferred rust fungi are selected from the group of *Puccinia, Gymnosporangium, Juniperus, Cronartium, Hemileia,* and *Uromyces*; preferably *Puccinia sorghi, Gymnosporangium junlperi-virginianae, Juniperus virginiana, Cronartium ribicola, Hemilela vastatrix, Puccinia graminis, Puccinia coronata, Uromyces phaseoli, Puccinia hemerocallidis, Puccinia persistens* subsp. *Triticina, Puccinia striiformis, Puccinia graminis* causes, and/or *Uromyces appendeculatus.*

Further preferred pathogens, preferably pathogens of maize, are pathogens causing stalk rot diseases, in particular *Fusarium* stalk rot, *Gibberella* stalk rot, *Diplodia* stalk rot, and Charcoal rot and pathogens causing anthracnose. Preferred pathogens causing *Fusarium* stalk rot are *Fusarium verticillioides Fusarium proliferatum* or *Fusarium subglutinans*. A preferred pathogen causing *Gibberella* stalk rot is *Fusarium graminearum*. A preferred pathogen causing *Diplodia* stalk rot is *Diplodia maydis*. A preferred pathogen causing Charcoal rot is *Macrophomina phaseolina*. A preferred pathogen causing anthracnose is *Colletotrichum graminicola.*

HCP7 Expression Constructs and Vector Constructs

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30, or a functional fragment thereof, or an orthologue or a paralogue thereof, or a splice variant thereof;
 (ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 2, 8, 10, 12, 14, 16, 18, 20, or 22, a functional fragment thereof, an orthologue or a paralogue thereof; preferably the encoded protein confers enhanced fungal resistance relative to control plants;
 (iii) a nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
 (iv) a nucleic acid encoding the same HCP7 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30;
 (ii) a nucleic acid coding for a protein comprising an amino acid sequence having at least 80%, at least 90%, at least 95%, at least 98%, at least 99% sequence identity, or even 100% sequence identity with SEQ ID NO: 2, 8, 10, 12, 14, 16, 18, 20, or 22; preferably the encoded protein confers enhanced fungal resistance relative to control plants;
 (iii) a nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
 (iv) a nucleic acid encoding the same HCP7 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 1,
 (ii) a nucleic acid coding for a protein having at least 80%, at least 90%, at least 95%, at least 98%, at least 99% sequence identity, or even 100% sequence identity with SEQ ID NO: 2; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) a nucleic acid encoding the same HCP7 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 4;

(ii) a nucleic acid coding for a protein having at least 80%, at least 90%, at least 95%, at least 98%, at least 99% sequence identity, or even 100% sequence identity with SEQ ID NO: 2; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) a nucleic acid encoding the same HCP7 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

In the case of a genomic library, the natural genetic environment of the nucleic acid sequence is preferably retained, at least in part. The environment preferably flanks the nucleic acid sequence at least on one side and has a sequence length of at least 50 bp, preferably at least 500 bp, especially preferably at least 1000 bp, most preferably at least 5000 bp.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

In preferred embodiments, the increase in the protein amount and/or activity of the HCP7 protein takes place in a constitutive or tissue-specific manner. In especially preferred embodiments, an essentially pathogen-induced increase in the protein amount and/or protein activity takes place, for example by recombinant expression of the HCP7 nucleic acid under the control of a fungal-inducable promoter. In particular, the expression of the HCP7 nucleic acid takes place on fungal infected sites, where, however, preferably the expression of the HCP7 nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis*

(PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:
WIR5 (=GstA1); acc. X56012; Dudler & Schweizer,
GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998),
GLP2a, acc. AJ237942, Schweizer P., Christoffel A. and Dudler R., Plant J. 20, 541 (1999);
Prx7, acc. AJ003141, Kristensen B. K., Ammitzboll H., Rasmussen S. K. and Nielsen K. A., Molecular Plant Pathology, 2(6), 311 (2001);
GerA, acc. AF250933; Wu S., Druka A., Horvath H., Kleinhofs A., Kannangara G. and von Wettstein D., Plant Phys Biochem 38, 685 (2000);
OsROC1, acc. AP004656
RTBV, acc. AAV62708, AAV62707; Kloti A., Henrich C., Bieri S., He X., Chen G., Burkhardt P. K., Wünn J., Lucca P., Hohn T., Potrykus I. and Fütterer J., PMB 40, 249 (1999);
Chitinase ChtC2-Promoter from potato (Ancillo et al., Planta. 217(4), 566, (2003));
AtProT3 Promoter (Grallath et al., Plant Physiology. 137(1), 117 (2005));
SHN-Promoters from *Arabidopsis* (AP2/EREBP transcription factors involved in cutin and wax production) (Aarón et al., Plant Cell. 16(9), 2463 (2004)); and/or
GSTA1 from wheat (Dudler et al., WP2005306368 and Altpeter et al., Plant Molecular Biology. 57(2), 271 (2005)).

Mesophyll-specific promoters may be selected from the group consisting of:
PPCZm1 (=PEPC); Kausch A. P., Owen T. P., Zachwieja S. J., Flynn A. R. and Sheen J., Plant Mol. Biol. 45, 1 (2001);
OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993); OsPPDK, acc. AC099041;
TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1b, acc. X74940; Bryngelsson et al., Mol. Plant Microbe Interact. 7(2), 267 (1994);
HvB1,3gluc; acc. AF479647;
HvPrx8, acc. AJ276227; Kristensen et al., Molecular Plant Pathology, 2(6), 311 (2001); and/or
HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of
PcUbi promoter from parsley (WO 03/102198)
CaMV 35S promoter: Cauliflower Mosaic Virus 35S promoter (Benfey et al. 1989 EMBO J. 8(8): 2195-2202),
STPT promoter: *Arabidopsis thaliana* Short Triose phosphate translocator promoter (Accession NM_123979)
Act1 promoter: *Oryza sativa* actin 1 gene promoter (McElroy et al. 1990 PLANT CELL 2(2) 163-171 a) and/or
EF1A2 promoter: *Glycine max* translation elongation factor EF1 alpha (US 20090133159).

In preferred embodiments, the increase in the protein quantity or function of the HCP7 protein takes place in a constitutive or tissue-specific manner. In especially preferred embodiments, an essentially pathogen-induced increase in the protein quantity or protein function takes place, for example by exogenous expression of the HCP7 nucleic acid under the control of a fungal-inducible promoter, preferably a rust-inducible promoter. In particular, the expression of the HCP7 nucleic acid takes place on fungal infected sites, where, however, preferably the expression of the HCP7 nucleic acid sequence remains essentially unchanged in tissues not infected by fungus.

Preferably, the HCP7 nucleic acid is under the control of a rust induced mesophyll specific promoter. More preferably, the promoter is the rust induced mesophyll specific promoter 820.

A preferred terminator is the terminator of the cathepsin D inhibitor gene from *Solanum tuberosum*.

Preferred promoter-terminator combinations with the gene of interest in between are a promoter from parsley, preferably, the parsley ubiquitine promoter or the maize ubiquitin promoter, in combination with the terminator of the cathepsin D inhibitor gene from *Solanum tuberosum*. Another preferred promoter-terminator combination is the rust induced mesophyll specific promoter 820 in combination with the terminator of the cathepsin D inhibitor gene from *Solanum tuberosum*.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

Transgenic Organisms; Transgenic Plants, Plant Parts, and Plant Cells

A preferred embodiment is a transgenic plant, transgenic plant part, or transgenic plant cell overexpressing an exogenous HCP7 protein. Preferably, the HCP7 protein overexpressed in the plant, plant part or plant cell is encoded by a nucleic acid comprising (i) an exogenous nucleic acid having at least 60% identity with SEQ ID NO: 4, 1, 3, 7, 9, 11, 13, 15, 17, 19, 21, 23, 24, 25, 26, 27, 28, 29, or 30, or a functional fragment, thereof, an orthologue or a paralogue thereof, or a splice variant thereof; or by (ii) an exogenous nucleic acid encoding a protein comprising an amino acid sequence having at least 60% identity with SEQ ID NO: 2, 8, 10, 12, 14, 16, 18, 20, or 22, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP7 protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30; or comprises an exogenous nucleic acid encoding a protein having at least 80%, at least 90%, at least 95%, at least 98%, at least 99% sequence identity, or even 100% sequence identity with SEQ ID NO: 2, 8, 10, 12, 14, 16, 18, 20, or 22.

A preferred embodiment is a transgenic plant, transgenic plant part, or transgenic plant cell overexpressing an exogenous HCP7 protein. Preferably, the HCP7 protein overexpressed in the plant, plant part or plant cell is encoded by (i) an exogenous nucleic acid having at least 60% identity with SEQ ID NO: 1 or a functional fragment, thereof, an orthologue or a paralogue thereof, or a splice variant thereof; or by (ii) an exogenous nucleic acid encoding a protein having at least 60% identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP7 protein as the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous HCP7 protein. Preferably, the HCP7 protein overexpressed in the plant, plant part or plant cell is encoded by (i) an exogenous nucleic acid having at least 60% identity with SEQ ID NO: 4 or a functional fragment, thereof, an orthologue or a paralogue thereof, or a splice variant thereof; or by (ii) an exogenous nucleic acid encoding a protein having at least 60% identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP7 protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 80%, at least 90%, at least 95%, at least 98%, at least 99% sequence identity, or even 100% sequence identity with SEQ ID NO: 2.

In preferred embodiments, the protein amount of a HCP7 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the HCP7 nucleic acid.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos.

5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the HCP7 nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, constructs or vectors or expression cassettes are not present in the genome of the original plant or are present in the genome of the transgenic plant not at their natural locus of the genome of the original plant.

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. medullare Alef. emend. C.O. Lehm), sugar pea (*Pisum sativum* L. convar. axiphium Alef emend. C.O. Lehm), also called snow pea, edible-podded pea or mangetout, (*Pisum granda sneida* L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, *dolichos* bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phacosporaceae, for example soybean rust, wherein the recombinant nucleic acid used to generate a transgenic plant comprises a promoter that is functional in the plant cell, operably linked to an HCP7 nucleic acid, which is preferably SEQ ID NO: 1, and a terminator regulatory sequence.

In one embodiment, the present invention refers to a method for the production of a transgenic plant, transgenic plant part, or transgenic plant cell having increased fungal resistance, comprising
(a) introducing a recombinant vector construct according to the present invention into a plant, a plant part or a plant cell and
(b) generating a transgenic plant from the plant, plant part or plant cell.

Preferably, the method for the production of the transgenic plant, transgenic plant part, or transgenic plant cell further comprises the step
(c) expressing the HCP7 protein, preferably encoded by a nucleic acid comprising
  (i) an exogenous nucleic acid having at least 60% identity with SEQ ID NO: 4, 1, 3, 7, 9, 11, 13, 15, 17, 19, 21, 23, 24, 25, 26, 27, 28, 29, or 30, a functional fragment thereof, an orthologue or a paralogue thereof, or a splice variant thereof;
  (ii) an exogenous nucleic acid encoding a protein comprising an amino acid sequence having at least 60% identity with SEQ ID NO: 2, 8, 10, 12, 14, 16, 18, 20, or 22, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
  (iv) an exogenous nucleic acid encoding the same HCP7 protein as the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step
(c) expressing the HCP7 protein, preferably encoded by
  (i) an exogenous nucleic acid having at least 60% identity with SEQ ID NO: 1, a functional fragment thereof, an orthologue or a paralogue thereof, or a splice variant thereof;
  (ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
  (iv) an exogenous nucleic acid encoding the same HCP7 protein as the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step
(c) expressing the HCP7 protein, preferably encoded by
  (i) an exogenous nucleic acid having at least 60% identity with SEQ ID NO: 4, a functional fragment thereof, an orthologue or a paralogue thereof, or a splice variant thereof;
  (ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same HCP7 protein as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 7, 9, 11, 13, 15, 17, 19, 21, 23, 24, 25, 26, 27, 28, 29, or 30, or a functional fragment thereof, or an orthologue or a paralogue thereof, or a splice variant thereof;

(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 8, 10, 12, 14, 16, 18, 20, or 22, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) an exogenous nucleic acid encoding the same HCP7 polypeptide as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises (i) the exogenous nucleic acid having at least 60% identity with SEQ ID NO: 4, 1, 3, 7, 9, 11, 13, 15, 17, 19, 21, 23, 24, 25, 26, 27, 28, 29, or 30, a functional fragment thereof, an orthologue or a paralogue thereof, or a splice variant thereof;

(ii) the exogenous nucleic acid encoding a protein comprising an amino acid sequence having at least 60% identity with SEQ ID NO: 2, 8, 10, 12, 14, 16, 18, 20, or 22, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) the exogenous nucleic acid encoding the same HCP7 protein as the nucleic acids of (i) to (iii) above, but differing from the nucleic acids of (i) to (iii) above due to the degeneracy of the genetic code;

preferably, the step of harvesting the seeds of the transgenic plant and planting the seeds and growing the seeds to plants, wherein the grown plant(s) comprises (i) the exogenous nucleic acid having at least 60% identity with SEQ ID NO: 4, 1, 3, 7, 9, 11, 13, 15, 17, 19, 21, 23, 24, 25, 26, 27, 28, 29, or 30, a functional fragment thereof, an orthologue or a paralogue thereof, or a splice variant thereof;

(ii) the exogenous nucleic acid encoding a protein comprising an amino acid sequence having at least 60% identity with SEQ ID NO: 2, 8, 10, 12, 14, 16, 18, 20, or 22, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) the exogenous nucleic acid encoding the same HCP7 protein as the nucleic acids of (i) to (iii) above, but differing from the nucleic acids of (i) to (iii) above due to the degeneracy of the genetic code;

is repeated more than one time, preferably, 1, 2, 3, 4, 5, 6, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the HCP7 gene or by directly screening for the HCP7 nucleic acid).

Furthermore, the use of the exogenous HCP7 nucleic acid or the recombinant vector construct comprising the HCP7 nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the HCP7 nucleic acid or HCP7 protein. The harvestable parts may be seeds, roots, leaves and/or flowers comprising the HCP7 nucleic acid or HCP7 protein or parts thereof. Preferred parts of soy plants are soy beans comprising the HCP7 nucleic acid or HCP7 protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the HCP7 nucleic acid or HCP7 protein.

Methods for Manufacturing a Product

In one embodiment the method for the production of a product comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/ Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the HCP7 nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing an HCP7 protein, preferably encoded by a nucleic acid comprising
  (i) an exogenous nucleic acid having at least 60% identity with SEQ ID NO: 4, 1, 3, 7, 9, 11, 13, 15, 17, 19, 21, 23, 24, 25, 26, 27, 28, 29, or 30, a functional fragment thereof, an orthologue or a paralogue thereof, or a splice variant thereof;
  (ii) an exogenous nucleic acid encoding a protein comprising an amino acid sequence having at least 60% identity with SEQ ID NO: 2, 8, 10, 12, 14, 16, 18, 20, or 22, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP7 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
  (iv) an exogenous nucleic acid encoding the same HCP7 protein as the nucleic acids of (i) to (iii) above, but differing from the nucleic acids of (i) to (iii) above due to the degeneracy of the genetic code.

Another preferred embodiment is a method for plant improvement comprising
(a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding the HCP7 protein; and optionally
(f) producing propagation material from the plants expressing the nucleic acid encoding the HCP7 protein.

The transgenic plants may be selected by known methods as described above (e.g., by screening for the presence of one or more markers which are encoded by plant-expressible genes co-transferred with the HCP7 gene or screening for the HCP7 nucleic acid itself).

According to the present invention, the introduced HCP7 nucleic acid may be maintained in the plant cell stably if it is incorporated into a non-chromosomal autonomous replicon or integrated into the plant chromosomes. Whether present in an extra-chromosomal non-replicating or replicating vector construct or a vector construct that is integrated into a chromosome, the exogenous HCP7 nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary Agrobacterium vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of E. coli cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The cDNA was produced from *Arabidopsis thaliana* (ecotype Col-0) RNA by using the Superscript II cDNA synthesis kit (Invitrogen). All steps of cDNA preparation and purification were performed according as described in the manual.

First, the full-length HCP7 sequence from ATG to Stop (SEQ ID NO: 1) was specifically amplified from the cDNA by PCR as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.2 mM of each dNTP, 100 ng cDNA of *Arabidopsis thaliana* (var Columbia-0), 20 pmol forward primer, 20 pmol reverse primer, 1 u Phusion hot-start, Pfu Ultra, Pfu Turbo or Herculase DNA polymerase.

The amplification cycles were as follows:
1 cycle of 60 seconds at 98° C., followed by 35 cycles of in each case 10 seconds at 98° C., 30 seconds at 65° C. and 60 seconds at 72° C., followed by 1 cycle of 10 minutes at 72° C., then 4° C.

The primers (as shown in SEQ ID NO: 5 and 6) were designed in a way that the specifically bind to sequences in the 5' and 3'UTR upstream of the start ATG an downstream of the stop codon of the HCP7 coding sequence. The primers are designed in a way that an Acc65I restriction site is located in front of the start-ATG and a SalI restriction site downstream of the stop-codon i) forward primer:
(SEQ ID NO: 5)
5'-CAGGTACC<u>ATG</u>GCAGATATAATCGGC-3' ii) reverse primer:
(SEQ ID NO: 6)
5'-TAGTCGAC<u>CTA</u>ATCGTCGAGCCAATC-3'

The amplified fragment (2452 bp) was eluted and purified from an 1% agarose gel by using the Nucleospin Extract II Kit (Macherey and Nagel, Dueren, Germany).

As the amount of recovered DNA was very low, a Re-PCR was performed using the same primers (SEQ ID NO: 5 and 6) as before. The HCP7 full-length sequence (SEQ ID NO: 1) was specifically amplified from the eluted PCR fragment (see above) by PCR as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.2 mM of each dNTP, 10-50 ng template DNA derived from the previous PCR of, 20 pmol forward primer, 20 pmol reverse primer, 1 u Phusion hot-start, Pfu Ultra, Pfu Turbo or Herculase DNA polymerase.

The amplification cycles were as follows:
1 cycle of 60 seconds at 98° C., followed by 35 cycles of in each case 10 seconds at 98° C., 30 seconds at 60° C. and 60 seconds at 72° C., followed by 1 cycle of 10 minutes at 72° C., then 4° C.

Re-PCR was performed using the same primers (SEQ ID NO: 5 and 6) as before.

The amplified fragments were digested using the restriction enzymes Acc65I and SalI (NEB Biolabs) and ligated in a Acc65I/SalI digested Gateway pENTRY-B vector (Invitrogen, Life Technologies, Carlsbad, Calif., USA) in a way that the full-length HCP7 fragment is located in sense direction between the attL1 and attL2 recombination sites.

It is also possible to generate all DNA fragments mentioned in this invention by DNA synthesis (Geneart, Regensburg, Germany), as done for the optimized HCP7 sequence (SEQ ID NO: 4).

Figure 2:
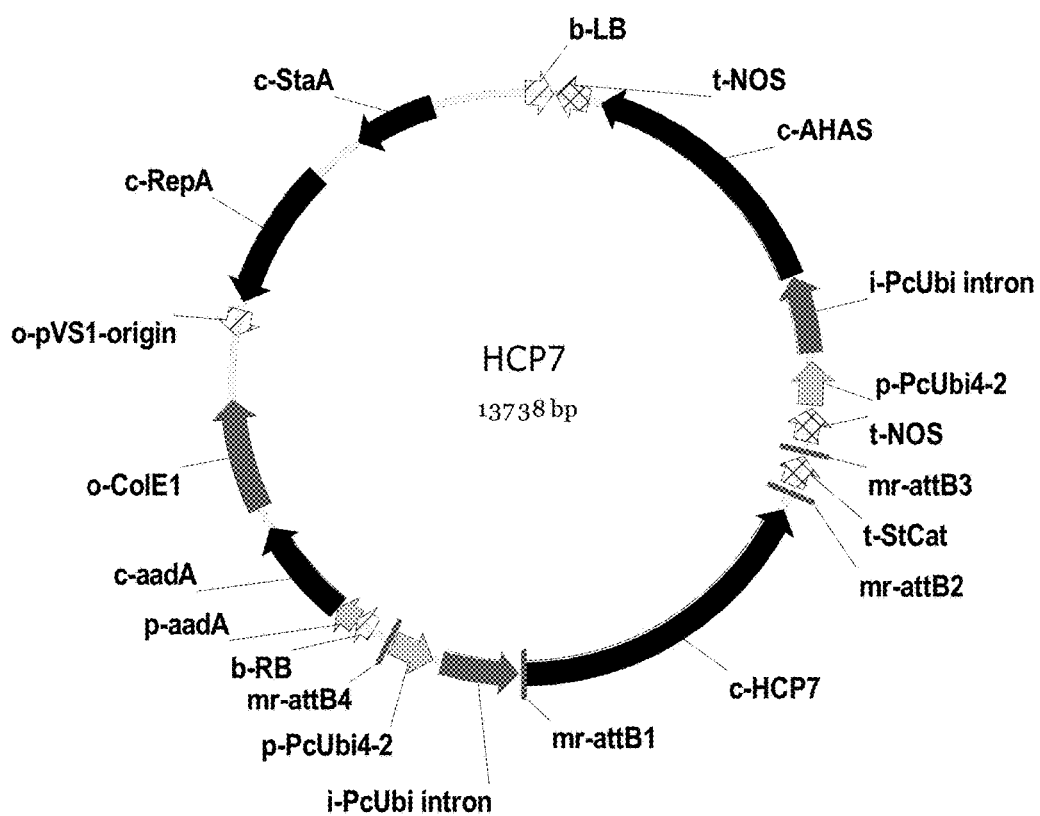

To obtain the binary plant transformation vector, a triple LR reaction (Gateway system, Invitrogen, Life Technologies, Carlsbad, Calif., USA) was performed according to manufacturer's protocol by using a pENTRY-A vector containing a parsley ubiquitine promoter, the HCP-7 full-length gene in a pENTRY-B vector and a pENTRY-C vector containing the terminator of the cathepsin D inhibitor gene from *Solanum tuberosum*. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection under control of a pcUbi-promoter (see FIG. 2). The recombination reaction was transformed into *E. coli* (DH5alpha), mini-prepped and screened by specific restriction digestions. A positive clone from each vector construct was sequenced and submitted soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an OD$_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 µl to 3 ml of working *Agrobacterium* stock in a 500 ml Erlenmeyer flask. The flask was shaken overnight at 25° C. until the OD$_{600}$ was between 0.8 and 1.0. Before preparing the soy explants, the Agrobacteria were pelleted by centrifugation for 10 min at 5,500×g at 20° C. The pellet was resuspended in liquid CCM to the desired density (OD$_{600}$ 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were sub-cultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soy-plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol. Plant (2007) 43:536-549; to remove excess *Agrobacterium*) or Modwash medium (1× B5 major salts, 1× B5 minor salts, 1×MSIII iron, 3% Sucrose, 1× B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 µE/m²s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Growth of Plants

10 $T_1$ plants per event were potted and grown for 3-4 weeks in the phytochamber (16 h-day—und 8 h-night-Rhythm at a temperature of 16 and 22° C. und a humidity of 75%) till the first 2 trifoliate leaves were fully expanded.

4.2 Inoculation

The plants were inoculated with spores of *P. pachyrhizi*.

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×10 spores/ml. For the microscopy, a density of >5×10$^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 36 T1 soybean plants (4 independent events, 7-10 plants each) expressing HCP7 protein were inoculated with spores of *Phakopsora pachyrhizi*. The macroscopic disease symptoms of soy against *P. pachyrhizi* of the inoculated soybean plants were scored 14 days after inoculation.

Figure 7:
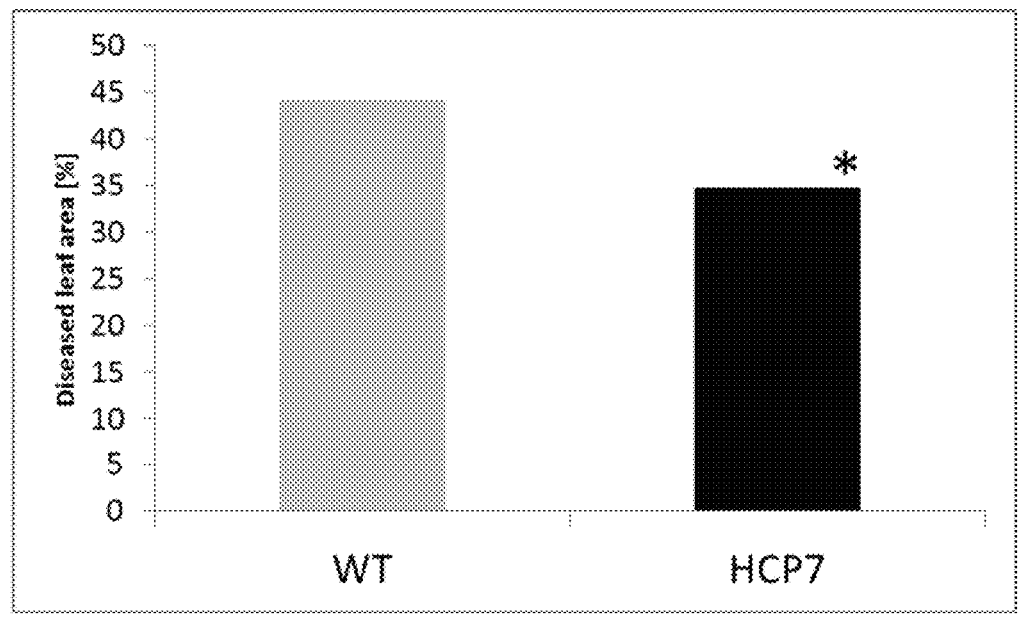

The average of the percentage of the leaf area showing fungal colonies or strong yellowing/browning on all leaves was considered as diseased leaf area. At all 36 soybean T1 plants expressing HCP7 (expression checked by RT-PCR) were evaluated in parallel to non-transgenic control plants. Non-transgenic soy plants grown in parallel to the transgenic plants were used as control. The average of the diseased leaf area is shown in FIG. 7 for plants expressing recombinant HCP7 compared with wildtype plants. Overexpression of HCP7 reduces the diseased leaf area in comparison to non-transgenic control plants by 21.1% in average over all events and plants generated. This data clearly indicates that the in-planta expression of the HCP7 expression vector construct lead to a lower disease scoring of transgenic plants compared to non-transgenic controls. So, the expression of HCP7 protein (as shown in SEQ ID NO: 2) in soybean significantly ($p<0.05$) increases the resistance of soy against soybean rust.

Example 7: Construction of Maize Expression Cassettes

The nucleic acid sequence encoding the optimized cDNA of HCP7 (as shown in SEQ ID NO:4) was synthesized in a way that enables further cloning. The expression cassettes were then assembled in a vector by cloning the synthesized DNA encoding the HCP7 gene from *Arabidopsis thaliana* downstream of a SCBV254 promoter (Sugarcane Bacilliform Virus promoter fragment ScBV-254) and upstream of a t-nos terminator (3'UTR of Nopaline Synthase from *Agrobacterium tumefaciens*). An intron from the rice Met1 gene was also cloned in between of the promoter and the HCP7 sequence.

Plant transformation binary vectors such as pBi-nAR were used (Höfgen & Willmitzer 1990, Plant Sci. 66:221-230). Further examples for plant binary vectors are the pSUN300 or pSUN2-GW vectors and the pPZP vectors (Hajdukiewicz et al., Plant Molecular Biology 25: 989-994, 1994). As target a binary plant transformation vector was used which is composed of: (1) a Kanamycin resistance cassette for bacterial selection (2) a pVS1 origin for replication in Agrobacteria (3) a ColE1 origin of replication for stable maintenance in *E. coli* and (4) between the right and left border a ZmAHAS gene as selectable marker under control of a ZmAHAS-promoter.

Construction of the binary vectors was performed by ligation of the HCP7 expression cassette, as described above, into the binary vector. The recombinant vector containing the HCP7 expression cassette was transformed into Top10 cells (Invitrogen) using standard conditions. Transformed cells were selected on LB agar containing 50 µg/ml kanamycin grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al., 1989, "Molecular Cloning: A Laboratory Manual," 2nd Edition, Cold Spring Harbor Laboratory Press, Cold Spring Harbor, N.Y.).

Example 8: Maize Transformation

*Agrobacterium* cells harboring a plasmid containing the gene of interest and the mutated maize AHAS gene were grown in YP medium supplemented with appropriate antibiotics for 1-2 days. One loop of *Agrobacterium* cells was collected and suspended in 1.8 ml M-LS-002 medium (LS-inf). The cultures were incubated while shaking at 1,200 rpm for 5 min-3 hrs. Corn cobs were harvested at 8-11 days after pollination. The cobs were sterilized in 20% Clorox solution for 5 min, followed by spraying with 70% Ethanol and then thoroughly rinsed with sterile water. Immature embryos 0.8-2.0 mm in size were dissected into the tube containing *Agrobacterium* cells in LS-inf solution.

The constructs were transformed into immature embryos by a protocol modified from Japan Tobacco *Agrobacterium* mediated plant transformation method (U.S. Pat. Nos. 5,591,616; 5,731,179; 6,653,529; and U.S. Patent Application Publication No. 2009/0249514). Two types of plasmid vectors were used for transformation. One type had only one T-DNA border on each of left and right side of the border, and selectable marker gene and gene of interest were between the left and right T-DNA borders. The other type was so called "two T-DNA constructs" as described in Japan Tobacco U.S. Pat. No. 5,731,179. In the two DNA constructs, the selectable marker gene was located between one set of T-DNA borders and the gene of interest was included in between the second set of T-DNA borders. Either plasmid vector can be used. The plasmid vector was electroporated into *Agrobacterium*.

*Agrobacterium* infection of the embryos was carried out by inverting the tube several times. The mixture was poured onto a filter paper disk on the surface of a plate containing co-cultivation medium (M-LS-011). The liquid agro-solution was removed and the embryos were checked under a microscope and placed scutellum side up. Embryos were cultured in the dark at 22° C. for 2-4 days, and transferred to M-MS-101 medium without selection and incubated for four to seven days. Embryos were then transferred to M-LS-202 medium containing 0.75 µM imazethapyr and grown for three weeks at 27° C. to select for transformed callus cells.

Plant regeneration was initiated by transferring resistant calli to M-LS-504 medium supplemented with 0.75 µM imazethapyr and growing under light at 2&C for two to three weeks. Regenerated shoots were then transferred to a rooting box with M-MS-618 medium (0.5 µM imazethapyr). Plantlets with roots were transferred to soil-less potting mixture and grown in a growth chamber for a week, then transplanted to larger pots and maintained in a greenhouse until maturity.

Transgenic maize plant production is also described, for example, in U.S. Pat. Nos. 5,591,616 and 6,653,529; U.S. Patent Application Publication No. 2009/0249514; and WO/2006136596, each of which are hereby incorporated by reference in their entirety. Transformation of maize may be made using *Agrobacterium* transformation, as described in U.S. Pat. Nos. 5,591,616; 5,731,179: U.S. Patent Application Publication No. 2002/0104132, and the like. Transformation of maize (*Zea mays* L.) can also be performed with a modification of the method described by Ishida et al. (Nature Biotech., 1996, 14:745-750). The inbred line A188 (University of Minnesota) or hybrids with A188 as a parent are good sources of donor material for transformation (Fromm et al., Biotech, 1990, 8:833), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system is described in WO 94/00977 and WO 95/06722. Vectors are constructed as described. Various selection marker genes are used including the maize gene encoding a mutated acetohydroxy acid synthase (AHAS) enzyme (U.S. Pat. No. 6,025,541). Similarly, various promoters are used to regulate the trait gene to provide constitutive, developmental, inducible, tissue or environmental regulation of gene transcription.

Excised embryos can be used and can be grown on callus induction medium, then maize regeneration medium, containing imidazolinone as a selection agent. The Petri dishes are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

Example 9: *Fusarium* and *Colletotrichum* Resistance Screening

Transgenic plants are grown in greenhouse or phyto-chamber under standard growing conditions in a controlled environment (20-25° C., 60-90% humidity). Shortly after plants enter the reproductive phase the transgenic plants are inoculated near the base of the stalk using a fungal suspension of spores (105 spores in PBS solution) of *Fusarium* ssp. or *Colletotrichum graminicola*. Plants are incubated for 2-4 weeks at 20-25° C. and 60-90% humidity.

For scoring the disease, stalks are split and the progression of the disease was scored by observation of the characteristic brown to black color of the fungus as it grows up the stalk. Disease ratings were conducted by assigning a visual score. Per experiment the diseased leaf area of more than 10 transgenic plants (and wild-type plants as control) is scored. For analysis the average of the diseased leaf area of the non-transgenic mother plant is set to 100% to calculate the relative diseased leaf area of the transgenic lines The expression of the HCP7 gene will lead to enhanced resistance of corn against *Fusarium* ssp. And *Colletotrichum graminicola*.

The invention claimed is:

1. A method for increasing soybean rust resistance in a soybean plant, a soybean plant part, or a soybean plant cell, said method comprising
increasing the expression and/or activity of a HCP7 protein in the soybean plant, soybean plant part, or soybean plant cell in comparison to a wild type soybean plant, wild type soybean plant part or wild type soybean plant cell, wherein the HCP7 protein is encoded by an exogenous nucleic acid encoding a protein having an amino acid sequence with at least 80% identity to SEQ ID NO: 2, wherein the HCP7 protein confers increased resistance against soybean rust to the soybean plant, soybean plant part, or soybean plant cell in comparison to a wild type soybean plant, wild type soybean plant part or wild type soybean plant cell.

2. The method of claim 1, comprising (a) stably transforming a soybean plant cell with an expression cassette comprising an exogenous nucleic acid encoding an HCP7 protein having an amino acid sequence with at least 80% identity to SEQ ID NO: 2 in functional linkage with a promoter; and (b) regenerating the soybean plant from the soybean plant cell.

3. A recombinant vector construct comprising:

(a) a nucleic acid encoding a protein having an amino acid sequence with at least 80% identity to SEQ ID NO: 2 operably linked with (b) a heterologous promoter and (c) a transcription termination sequence, wherein expression of said recombinant vector construct in a soybean plant, soybean plant part, or soybean plant cell confers increased resistance against soybean rust thereto in comparison to a wild type soybean plant, wild type soybean plant part, or wild type soybean plant cell.

4. The method of claim 2, wherein the promoter is a constitutive promoter, pathogen-inducible promoter, a mesophyll-specific promoter or an epidermis specific-promoter.

5. A transgenic soybean plant, transgenic soybean plant part, or transgenic soybean plant cell comprising an exogenous nucleic acid encoding an HCP7 protein comprising an amino acid sequence with at least 80% identity with SEQ ID NO: 2, wherein expression of said exogenous nucleic acid in the transgenic soybean plant, transgenic soybean plant part, or transgenic soybean plant cell confers increased resistance against soybean rust thereto in comparison to a wild type soybean plant, wild type soybean plant part, or wild type soybean plant cell.

6. A method for the production of a transgenic soybean plant, transgenic soybean plant part, or transgenic soybean plant cell having increased resistance against soybean rust, comprising (a) introducing the recombinant vector construct of claim 3 into a soybean plant, a soybean plant part, or a soybean plant cell; and (b) generating a transgenic soybean plant, transgenic soybean plant part, or transgenic soybean plant cell from the soybean plant, soybean plant part or soybean plant cell.

7. The method of claim 6, further comprising the step of harvesting the seeds of the transgenic soybean plant and planting the seeds and growing the seeds to soybean plants, wherein the grown soybean plants comprise the exogenous nucleic acid encoding a protein having an amino acid sequence with at least 80% identity with SEQ ID NO: 2.

8. A harvestable part of the transgenic soybean plant of claim 5, wherein the part comprises the exogenous nucleic acid encoding a protein having an amino acid sequence with at least 80% identity with SEQ ID NO: 2.

9. A product derived from the soybean plant of claim 5, wherein the product comprises the exogenous nucleic acid encoding a protein having an amino acid sequence with at least 80% identity with SEQ ID NO: 2.

10. A method for the production of a product comprising a) growing the soybean plant of claim 5; and b) producing said product from or by the soybean plant or a part of the soybean plant.

11. The method of claim 10 comprising a) growing the soybean plant and removing the harvestable parts from the soybean plant; and b) producing said product from or by the harvestable parts of the soybean plant.

12. The method of claim 10, wherein the product is meal or oil.

13. The method of claim 1, wherein the resistance against soybean rust is resistance against *Phakopsora meibomiae, Phakopsora pachyrhizi*, or a combination thereof.

14. A method for breeding a fungal resistant soybean plant comprising (a) crossing the soybean plant of claim 5 with a second soybean plant;

(b) obtaining seed from the cross of step (a);

(c) planting said seeds and growing the seeds to soybean plants; and (d) selecting from the soybean plants produced in step (c) plants expressing the HCP7 protein.

15. A method for controlling soybean rust in a soybean plant, said method comprising providing a transgenic soybean plant comprising an exogenous nucleic acid encoding an HCP7 protein having an amino acid sequence with at least 80% identity to SEQ ID NO: 2, wherein expression of the nucleic acid leads to increased soybean rust resistance in said soybean plant as compared to a wild type soybean plant such that soybean rust is controlled in the transgenic soybean plant.

16. The method of claim 15, wherein the soybean rust that is controlled is *Phakopsora meibomiae* and/or *Phakopsora pachyrhizi*.

17. The method of claim 1, wherein the HCP7 protein has an amino acid sequence with at least 85% identity to SEQ ID NO:2.

18. The method of claim 1, wherein the HCP7 protein has an amino acid sequence with at least 90% identity to SEQ ID NO:2.

19. The recombinant vector construct of claim 3, wherein the HCP7 protein has an amino acid sequence with at least 85% identity to SEQ ID NO:2.

20. The recombinant vector construct of claim 3, wherein the HCP7 protein has an amino acid sequence with at least 90% identity to SEQ ID NO:2.

21. The transgenic soybean plant, transgenic soybean plant part, or transgenic soybean plant cell of claim 5, wherein the HCP7 protein has an amino acid sequence with at least 85% identity to SEQ ID NO:2.

22. The transgenic soybean plant, transgenic soybean plant part, or transgenic soybean plant cell of claim 5, wherein the HCP7 protein has an amino acid sequence with at least 90% identity to SEQ ID NO:2.

* * * * *

SEQUENCE LISTING

<160> NUMBER OF SEQ ID NOS: 30

<210> SEQ ID NO 1
<211> LENGTH: 2436
<212> TYPE: DNA

<213> ORGANISM: Arabidopsis thaliana
<220> FEATURE:
<221> NAME/KEY: source
<222> LOCATION: 1..2436
<223> OTHER INFORMATION: /organism="Arabidopsis thaliana"
      /mol_type="unassigned DNA"

<400> SEQUENCE: 1

```
atggcagata taatcggcgg cgaagttgtg acggagctcg tgaggcagct ctatgcggtt     60
tctcaaaaaa ccctcagatg cagaggcatc gccaaaaatc tcgccaccat gatcgatggt    120
cttcaaccaa cgatcaagga gatccaatac agcggcgtcg agctcacacc tcatcgccag    180
gctcagttgc gtatgttctc ggaaacctta gacaagtgta ggaagctcac cgagaaagtt    240
cttaaatcca gccgttggaa catggttaga cagctactcc atgttaggaa aatggagaat    300
cttcagagta aagtgtctag ctttctcaac ggtcaattgt tagtccatgt tctcgctgat    360
gttcatcatg ttcgagccga ttctgaattc cggttcgatc ggattgatag aaggttgat    420
agtttgaatg agaagcttgg ttctatgaaa ctcaggggaa gtgaatcgtt gcgtgaggcg    480
ttgaagacgg ccgaggctac cgttgagatg gtgacaaccg atggtgctga tttggggtg    540
ggattggatt tgggaaagag gaaggtgaag gagatgttgt ttaaatccat tgatggggaa    600
agacttattg gtatctctgg gatgagtggt tcagggaaaa ccactcttgc caaagagctt    660
gcccgggacg aggaggttcg aggccacttt gggaacaagg ttttgtttct gactgtgtca    720
caatctccca atcttgagga gcttagagcc catatatggg gatttcttac tagttatgag    780
gctggggttg gtgctactct tccagaatcg aggaagctag tgatccttga tgatgtttgg    840
acaagggaat ctctggacca gctgatgttc gaaaatattc ctggaaccac aactcttgtg    900
gtctcacggt ctaaactcgc agattctaga gtcacttatg atgtagagtt actcaatgaa    960
catgaagcaa cggccctgtt ctgtctctct gttttcaatc agaaattagt gccttcaggg   1020
ttcagccaaa gtttggtcaa gcaggttgtt ggggagtgta aggtctacc tttgtctctg   1080
aaagtcattg gtgcttcatt gaaagaacga cctgaaaaat attgggaagg tgcagtggag   1140
aggctatcaa gaggtgaacc tgctgatgaa actcatgaga gtagagtgtt tgctcaaatc   1200
gaagcaactc tagaaaatct tgaccctaaa accagagatt gtttcttggt tctcggtgct   1260
ttccctgaag ataagaagat ccctcttgat gttctcatca acgtgttggt tgagttgcat   1320
gatctcgagg atgcaactgc ttttgctgtt attgttgatt tagcaaacag gaatctcctt   1380
actcttgtga aagatccaag gtttggacat atgtacacta gctactatga tatatttgtc   1440
acgcagcatg atgttctaag agatgtagca cttcgtctta gcaatcatgg gaaagtaaat   1500
aacagagagc ggttattgat gccaaaaaga gagtcaatgc ttccgagaga atgggagagg   1560
aacaatgatg agccatacaa agccagagta gtttccattc acacaggaga aatgactcag   1620
atggattggt ttgacatgga actccctaag gctgaagttt tgatactaca cttctcttct   1680
gacaagtatg tattgcctcc tttcattgct aagatgggca agcttacagc gctcgtgatc   1740
atcaacaatg gtatgtctcc tgcgcgtcta catgacttct ccatctttac caatttggcc   1800
aaactcaaga gtctctggct tcagagggtt catgtccctg aactctctag cagtacagtg   1860
cccttgcaaa acctccacaa gctgtctctc atattctgca agatcaacac tagtcttgat   1920
cagacagagc tagacattgc ccaaatcttc ccaaaattgt ctgatcttac aatagatcat   1980
tgtgatgatc ttctggaact accttcgacc atctgtggaa tcacctctct caattccatc   2040
agcataacaa attgtccccg catcaaggaa ttgcctaaga atctgagtaa gctaaaagcc   2100
```

-continued

```
cttcagcttc tgaggctata cgcttgccat gagctgaatt ctctgcctgt ggaaatctgt      2160
gaactgccaa gactaaagta tgttgacatt tctcaatgtg tcagcctgag ttctcttccg      2220
gaaaagatag gaaaggtaaa gacacttgag aaaatcgaca cgagggaatg cagcttatcg      2280
agcataccaa actctgtggt tttattgact tctctacgcc atgtaatatg cgatagagag      2340
gctttatgga tgtgggaaaa ggtccagaag gcggttgcag gacttcgtgt tgaagctgcg      2400
gaaaaatctt tcagcaggga ttggctcgac gattag                                2436
```

```
<210> SEQ ID NO 2
<211> LENGTH: 811
<212> TYPE: PRT
<213> ORGANISM: Arabidopsis thaliana

<400> SEQUENCE: 2

Met Ala Asp Ile Ile Gly Gly Glu Val Val Thr Glu Leu Val Arg Gln
1               5                   10                  15

Leu Tyr Ala Val Ser Gln Lys Thr Leu Arg Cys Arg Gly Ile Ala Lys
            20                  25                  30

Asn Leu Ala Thr Met Ile Asp Gly Leu Gln Pro Thr Ile Lys Glu Ile
        35                  40                  45

Gln Tyr Ser Gly Val Glu Leu Thr Pro His Arg Gln Ala Gln Leu Arg
    50                  55                  60

Met Phe Ser Glu Thr Leu Asp Lys Cys Arg Lys Leu Thr Glu Lys Val
65                  70                  75                  80

Leu Lys Ser Ser Arg Trp Asn Met Val Arg Gln Leu Leu His Val Arg
                85                  90                  95

Lys Met Glu Asn Leu Gln Ser Lys Val Ser Ser Phe Leu Asn Gly Gln
            100                 105                 110

Leu Leu Val His Val Leu Ala Asp Val His His Val Arg Ala Asp Ser
        115                 120                 125

Glu Phe Arg Phe Asp Arg Ile Asp Arg Lys Val Asp Ser Leu Asn Glu
    130                 135                 140

Lys Leu Gly Ser Met Lys Leu Arg Gly Ser Glu Ser Leu Arg Glu Ala
145                 150                 155                 160

Leu Lys Thr Ala Glu Ala Thr Val Glu Met Val Thr Asp Gly Ala
                165                 170                 175

Asp Leu Gly Val Gly Leu Asp Leu Gly Lys Arg Lys Val Lys Glu Met
            180                 185                 190

Leu Phe Lys Ser Ile Asp Gly Glu Arg Leu Ile Gly Ile Ser Gly Met
        195                 200                 205

Ser Gly Ser Gly Lys Thr Thr Leu Ala Lys Glu Leu Ala Arg Asp Glu
    210                 215                 220

Glu Val Arg Gly His Phe Gly Asn Lys Val Leu Phe Leu Thr Val Ser
225                 230                 235                 240

Gln Ser Pro Asn Leu Glu Glu Leu Arg Ala His Ile Trp Gly Phe Leu
                245                 250                 255

Thr Ser Tyr Glu Ala Gly Val Gly Ala Thr Leu Pro Glu Ser Arg Lys
            260                 265                 270

Leu Val Ile Leu Asp Asp Val Trp Thr Arg Glu Ser Leu Asp Gln Leu
        275                 280                 285

Met Phe Glu Asn Ile Pro Gly Thr Thr Thr Leu Val Val Ser Arg Ser
    290                 295                 300

Lys Leu Ala Asp Ser Arg Val Thr Tyr Asp Val Glu Leu Leu Asn Glu
305                 310                 315                 320
```

```
His Glu Ala Thr Ala Leu Phe Cys Leu Ser Val Phe Asn Gln Lys Leu
                325                 330                 335

Val Pro Ser Gly Phe Ser Gln Ser Leu Val Lys Gln Val Val Gly Glu
            340                 345                 350

Cys Lys Gly Leu Pro Leu Ser Leu Lys Val Ile Gly Ala Ser Leu Lys
            355                 360                 365

Glu Arg Pro Glu Lys Tyr Trp Glu Gly Ala Val Glu Arg Leu Ser Arg
            370                 375                 380

Gly Glu Pro Ala Asp Glu Thr His Glu Ser Arg Val Phe Ala Gln Ile
385                 390                 395                 400

Glu Ala Thr Leu Glu Asn Leu Asp Pro Lys Thr Arg Asp Cys Phe Leu
                405                 410                 415

Val Leu Gly Ala Phe Pro Glu Asp Lys Lys Ile Pro Leu Asp Val Leu
            420                 425                 430

Ile Asn Val Leu Val Glu Leu His Asp Leu Glu Asp Ala Thr Ala Phe
            435                 440                 445

Ala Val Ile Val Asp Leu Ala Asn Arg Asn Leu Leu Thr Leu Val Lys
            450                 455                 460

Asp Pro Arg Phe Gly His Met Tyr Thr Ser Tyr Tyr Asp Ile Phe Val
465                 470                 475                 480

Thr Gln His Asp Val Leu Arg Asp Val Ala Leu Arg Leu Ser Asn His
            485                 490                 495

Gly Lys Val Asn Asn Arg Glu Arg Leu Leu Met Pro Lys Arg Glu Ser
            500                 505                 510

Met Leu Pro Arg Glu Trp Glu Arg Asn Asn Asp Glu Pro Tyr Lys Ala
            515                 520                 525

Arg Val Val Ser Ile His Thr Gly Glu Met Thr Gln Met Asp Trp Phe
            530                 535                 540

Asp Met Glu Leu Pro Lys Ala Glu Val Leu Ile Leu His Phe Ser Ser
545                 550                 555                 560

Asp Lys Tyr Val Leu Pro Pro Phe Ile Ala Lys Met Gly Lys Leu Thr
                565                 570                 575

Ala Leu Val Ile Ile Asn Asn Gly Met Ser Pro Ala Arg Leu His Asp
            580                 585                 590

Phe Ser Ile Phe Thr Asn Leu Ala Lys Leu Lys Ser Leu Trp Leu Gln
            595                 600                 605

Arg Val His Val Pro Glu Leu Ser Ser Ser Thr Val Pro Leu Gln Asn
            610                 615                 620

Leu His Lys Leu Ser Leu Ile Phe Cys Lys Ile Asn Thr Ser Leu Asp
625                 630                 635                 640

Gln Thr Glu Leu Asp Ile Ala Gln Ile Phe Pro Lys Leu Ser Asp Leu
                645                 650                 655

Thr Ile Asp His Cys Asp Asp Leu Leu Glu Leu Pro Ser Thr Ile Cys
                660                 665                 670

Gly Ile Thr Ser Leu Asn Ser Ile Ser Ile Thr Asn Cys Pro Arg Ile
            675                 680                 685

Lys Glu Leu Pro Lys Asn Leu Ser Lys Leu Lys Ala Leu Gln Leu Leu
            690                 695                 700

Arg Leu Tyr Ala Cys His Glu Leu Asn Ser Leu Pro Val Glu Ile Cys
705                 710                 715                 720

Glu Leu Pro Arg Leu Lys Tyr Val Asp Ile Ser Gln Cys Val Ser Leu
                725                 730                 735
```

```
Ser Ser Leu Pro Glu Lys Ile Gly Lys Val Lys Thr Leu Glu Lys Ile
            740                 745                 750

Asp Thr Arg Glu Cys Ser Leu Ser Ile Pro Asn Ser Val Val Leu
        755                 760                 765

Leu Thr Ser Leu Arg His Val Ile Cys Asp Arg Glu Ala Leu Trp Met
    770                 775                 780

Trp Glu Lys Val Gln Lys Ala Val Ala Gly Leu Arg Val Glu Ala Ala
785                 790                 795                 800

Glu Lys Ser Phe Ser Arg Asp Trp Leu Asp Asp
            805                 810

<210> SEQ ID NO 3
<211> LENGTH: 3173
<212> TYPE: DNA
<213> ORGANISM: Arabidopsis thaliana
<220> FEATURE:
<221> NAME/KEY: source
<222> LOCATION: 1..3173
<223> OTHER INFORMATION: /organism="Arabidopsis thaliana"
      /mol_type="genomic DNA"

<400> SEQUENCE: 3
```

| | | | | | |
|---|---|---|---|---|---|
| acttatctct | ctctcttttt | ctcatcggcc | tttgccatgg | cagatataat | cggcggcgaa | 60 |
| gttgtgacgg | agctcgtgag | gcagctctat | gcggtttctc | aaaaaaccct | cagatgcaga | 120 |
| ggcatcgcca | aaatctcgc | caccatgatc | gatggtcttc | aaccaacgat | caaggagatc | 180 |
| caatacagcg | gcgtcgagct | cacacctcat | cgccaggctc | agttgcgtat | gttctcggaa | 240 |
| acttagaca | gtgtaggaa | gctcaccgag | aaagttctta | atccagccg | ttggaacatg | 300 |
| gttagacagc | tactccatgt | taggaaaatg | gagaatcttc | agagtaaagt | gtctagcttt | 360 |
| ctcaacggtc | aattgttagt | ccatgttctc | gctgatgttc | atcatgttcg | agccgattct | 420 |
| gaattccggt | tcgatcggat | tgataggaag | gttgatagtt | tgaatgagaa | gcttggttct | 480 |
| atgaaactca | ggggaagtga | atcgttgcgt | gaggcgttga | agacggccga | ggctaccgtt | 540 |
| gagatggtga | caaccgatgg | tgctgatttg | ggggtgggat | tggatttggg | aaagaggaag | 600 |
| gtgaaggaga | tgttgtttaa | atccattgat | ggggaaagac | ttattggtat | ctctgggatg | 660 |
| agtggttcag | ggaaaaccac | tcttgccaaa | gagcttgccc | gggacgagga | ggttcgaggt | 720 |
| aatgactttt | ctttgctggc | ctctgattcc | atatcgtttg | ttaatttgct | tggtacatct | 780 |
| ttgtgatctc | tattgcagtg | gctttgtggt | gtttcttaat | ggtatatttt | gttggtttat | 840 |
| cttgatgatc | atgcttctat | tgttttgttg | tatagttgag | ttgctaaaat | tgctttcatt | 900 |
| tactgctttt | atacaggcca | ctttgggaac | aaggttttgt | ttctgactgt | gtcacaatct | 960 |
| cccaatcttg | aggagcttag | agcccatata | tggggatttc | ttactagtta | tgaggctggg | 1020 |
| gttggtgcta | ctcttccaga | atcgaggaag | ctagtgatcc | ttgatgatgt | ttggacaagg | 1080 |
| gaatctctgg | accagctgat | gttcgaaaat | attcctggaa | ccacaactct | tgtggtctca | 1140 |
| cggtctaaac | tcgcagattc | tagagtcact | tatgatgtag | agttactcaa | tgaacatgaa | 1200 |
| gcaacggccc | tgttctgtct | ctctgttttc | aatcagaaat | tagtgccttc | agggttcagc | 1260 |
| caaagtttgg | tcaagcaggt | aattggtctg | cttaggtga | cacatgcata | gtagcaatgt | 1320 |
| tctttttttgc | tttcagtact | catattgtat | tgactctgtt | tggtaggttg | ttggggagtg | 1380 |
| taaaggtcta | cctttgtctc | tgaaagtcat | tggtgcttca | ttgaaagaac | gacctgaaaa | 1440 |
| atattgggaa | ggtgcagtgg | agaggctatc | aagaggtgaa | cctgctgatg | aaactcatga | 1500 |
| gagtagagtg | tttgctcaaa | tcgaagcaac | tctagaaaat | cttgacccta | aaaccagaga | 1560 |

-continued

```
ttgtttcttg gttctcggtg cttteectga agataagaag atccctcttg atgttctcat      1620
caacgtgttg gttgagttgc atgatctcga ggatgcaact gcttttgctg ttattgttga      1680
tttagcaaac aggaatctcc ttactcttgt gaaagatcca aggtacggtt ggttataaaa      1740
ctctttatga tctgatctct tgtagccact ttcaacggtt ttattcgttc ttagctaatg      1800
taattaccat cgataaattt tcaggtttgg acatatgtac actagctact atgatatatt      1860
tgtcacgcag catgatgttc taagagatgt agcacttcgt cttagcaatc atgggaaagt      1920
aaataacaga gagcggttat tgatgccaaa agagagtca atgcttccga gagaatggga       1980
gaggaacaat gatgagccat acaaagccag tagtttccc attcacacag gtaaggatt        2040
gttacacgac catcttctaa tgaataattt ggtttgttac tagaataata aagttttgat      2100
atggatttct gttttatttt acaggagaaa tgactcagat ggattggttt gacatggaac      2160
tccctaaggc tgaagttttg atactacact tctcttctga caagtatgta ttgcctcctt      2220
tcattgctaa gatgggcaag cttacagcgc tcgtgatcat caacaatggt atgtctcctg      2280
cgcgtctaca tgacttctcc atctttacca atttggccaa actcaagagt ctctggcttc      2340
agagggttca tgtccctgaa ctctctagca gtacagtgcc cttgcaaaac ctccacaagc      2400
tgtctctcat attctgcaag atcaacacta gtcttgatca gacagagcta gacattgccc      2460
aaatcttccc aaaattgtct gatcttacaa tagatcattg tgatgatctt ctggaactac      2520
cttcgaccat ctgtggaatc acctctctca attccatcag cataacaaat tgtccccgca      2580
tcaaggaatt gcctaagaat ctgagtaagc taaaagccct tcagcttctg aggctatacg      2640
cttgccatga gctgaattct ctgcctgtgg aaatctgtga actgccaaga ctaaagtatg      2700
ttgacatttc tcaatgtgtc agcctgagtt ctcttccgga aaagatagga aaggtaaaga      2760
cacttgagaa aatcgacacg agggaatgca gcttatcgag cataccaaac tctgtggttt      2820
tattgacttc tctacgccat gtaatatgcg atagagaggc tttatggatg tgggaaaagg      2880
tccagaaggc ggttgcagga cttcgtgttg aagctgcgga aaaatctttc agcagggatt      2940
ggctcgacga ttaggttcgt gattctctcc ctccgagccc ttagaagcat gttgtataaa      3000
atacttaatt gctaatctgt agcaaagtct tgtataatat tatattttat gagcacactc      3060
aagagtcaag agtcagtgca aacttcgttc ttgctctttc tccagaaatt tatctaacta      3120
taaaatttcc attcaagaat cagatttatg ttagtatcat tccagattcc ttt            3173
```

<210> SEQ ID NO 4
<211> LENGTH: 2436
<212> TYPE: DNA
<213> ORGANISM: Arabidopsis thaliana
<220> FEATURE:
<221> NAME/KEY: source
<222> LOCATION: 1..2436
<223> OTHER INFORMATION: /organism="Arabidopsis thaliana"
       /mol_type="unassigned DNA"

<400> SEQUENCE: 4

```
atggccgata taatcggagg tgaggttgtg actgagcttg ttaggcagct ctacgccgtt       60
agtcaaaaga cccttaggtg taggggatc gctaagaacc tcgctactat gattgacggc       120
cttcagccta ctatcaaaga aattcagtac tcaggcgtgg aactcacccc tcacagacaa      180
gctcaactta ggatgtttag cgagactctc gataagtgcc gtaagctcac cgagaaagtg      240
cttaagagtt ctaggtggaa tatggttagg cagctgcttc acgttaggaa gatggaaaac      300
cttcagtcta aagttagcag tttccttaac ggtcagctcc tcgttcacgt gctcgctgac      360
```

```
gttcaccacg ttagggctga ctcagagttt aggttcgata ggatcgaccg taaggtggac      420
tcacttaacg agaagctcgg ctctatgaag cttaggggct cagagtcact tagagaggct      480
cttaagactg ctgaggctac cgttgagatg gttactaccg acggtgctga tcttggagtg      540
ggacttgatc tcggtaagcg taaggtgaaa gagatgctct ttaagtctat cgacggcgag      600
aggctgatcg ggattagtgg aatgtcaggc tcaggtaaga ctaccctcgc taaagaactt      660
gctagggacg aagaggttag gggccacttc ggtaacaagg tgttgttcct taccgttagt      720
cagtcaccta acctcgagga acttaggggct catatctggg gattcctcac tagttacgag      780
gctggtgttg gagctactct tccagagtct agaaagctcg tgattctcga cgacgtgtgg      840
actagagagt cactcgatca gctgatgttc gagaatatcc caggtactac taccctcgtg      900
gttagtaggt ctaagttggc cgattctagg gtgacctacg acgtggaact tcttaacgaa      960
cacgaggcta ccgctctgtt ctgccttagt gtgtttaatc agaaactcgt gcctagcggc     1020
tttagtcaga gtttggttaa gcaggttgtg ggcgagtgta agggactccc acttagcctt     1080
aaggtgatcg gcgctagtct taaagagagg ccagagaagt attgggaggg tgctgttgag     1140
agacttagta gaggtgaacc agctgacgag actcacgagt ctagagtgtt cgctcaaatt     1200
gaggctaccc tcgagaacct cgatcctaag actagggatt gcttccttgt gctcggagct     1260
ttcccagagg ataagaaaat cccactcgac gtgctgatta acgtgctcgt tgagcttcac     1320
gatctcgagg acgctactgc tttcgctgtg attgtggacc tcgctaatag gaaccttctc     1380
actttagtta aggaccctag gttcggtcac atgtacacta gctactacga tatcttcgtg     1440
actcagcacg acgtattgag ggacgtagca cttaggctta gtaatcacgg taaggttaac     1500
aatagggaaa ggctcctgat gcctaagcgt gagtctatgc ttcctagaga gtgggagcgt     1560
aacaacgacg aaccctataa ggctagagtg gtctcgattc acaccggcga gatgactcag     1620
atggactggt tcgatatgga actccctaag gctgaggtgc tgatccttca ctttagctca     1680
gataagtacg tgctcccacc ctttattgct aagatgggaa agcttaccgc cctcgtgata     1740
attaacaacg ggatgtcacc agctaggctt cacgactttt cgatcttcac taaccctcgct    1800 aagcttaagt cactctggct tcagagggtt cacgtgccag agcttagcag ttctactgtg     1860
ccacttcaga accttcacaa gcttagcctg atcttctgta agattaacac tagcctcgat     1920
cagaccgagc tggatatcgc tcagatttttc cctaagctta gtgacctcac tatcgatcac    1980
tgcgacgacc ttttggagct gcctagtact atttgcggga tcactagcct taactctatt    2040
tcgatcacta actgccctag gatcaaagag cttcctaaga accttagtaa gcttaaggcc    2100
cttcagctcc ttaggctcta cgcttgtcac gagcttaact cactcccagt tgagatctgc    2160
gagctgccta ggcttaagta cgtagacatt agtcagtgcg ttagccttag ctcactcccc    2220
gagaagattg gtaaggttaa gaccctcgag aagatcgata cccgtgagtg ctcacttagc    2280
tctatcccta actcagtggt gctcctcact agtcttaggc acgttatctg cgatagggaa    2340
gctttgtgga tgtgggagaa ggttcagaag gctgttgctg gacttagagt tgaggctgcc    2400
gagaagagtt tctctaggga ttggctcgac gactaa                              2436
```

<210> SEQ ID NO 5
<211> LENGTH: 26
<212> TYPE: DNA
<213> ORGANISM: Arabidopsis thaliana
<220> FEATURE:
<221> NAME/KEY: source
<222> LOCATION: 1..26

```
<223> OTHER INFORMATION: /organism="Arabidopsis thaliana"
     /mol_type="unassigned DNA"

<400> SEQUENCE: 5
caggtaccat ggcagatata atcggc                                          26

<210> SEQ ID NO 6
<211> LENGTH: 26
<212> TYPE: DNA
<213> ORGANISM: Arabidopsis thaliana
<220> FEATURE:
<221> NAME/KEY: source
<222> LOCATION: 1..26
<223> OTHER INFORMATION: /organism="Arabidopsis thaliana"
     /mol_type="unassigned DNA"

<400> SEQUENCE: 6
tagtcgacct aatcgtcgag ccaatc                                          26

<210> SEQ ID NO 7
<211> LENGTH: 2433
<212> TYPE: DNA
<213> ORGANISM: Artificial Sequence
<220> FEATURE:
<221> NAME/KEY: source
<222> LOCATION: 1..2433
<223> OTHER INFORMATION: /organism="Artificial Sequence"
     /note="Nucleotide sequence HCP7, variant 1"
     /mol_type="unassigned DNA"

<400> SEQUENCE: 7
atggccgaca tcatcggcgg cgaggtggtg accgagctgg tgagacagct gtacgccgtg      60
agccagaaga ccctgagatg cagaggcatc gccaagaacc tggccaccat gatcgacggc     120
ctgcagccca ccatcaagga gatccagtac agcggcgtgg agctgacccc ccacagacag     180
gcccagctga gaatgttcag cgagaccctg acaagtgca gaaagctgac cgagaaggtg      240
ctgaagagca gcagatggaa catggtgaga cagctgctgc acgtgagaaa gatggagaac     300
ctgcagagca aggtgagcag cttcctgaac ggccagctgc tggtgcacgt gctggccgac     360
gtgcaccacg tgagagccga cagcgagttc agattcgaca gaatcgacaa gaaggtggag     420
tgcctgcagg agcacctgct gagcatgaga ctgagaggct gcgagaccct gagagagatg     480
atccacagcc tggacgtgtg cggcgagatg gtgaccaccg acggcgccga cctgggcgtg     540
ggcctggacc tgggcaagag aaaggtgaag gagatgctgt tcaagagcat cgacggcgag     600
agactgatcg gcatcagcgg catgagcggc agcggcaaga ccaccctggc caaggagctg     660
gccagagacg aggaggtgag aggccacttc ggcaacaagg tgctgttcct gaccgtgagc     720
cagagcccca acctggagga gctgagagcc cacatctggg gcttcctgac cagctacgag     780
gccggcgtgg gcgccaccct gcccgagagc agaaagctgg tgatcctgga cgacgtgtgg     840
accagagaga gcctggacca gctgatgttc gagaacatcc ccggcaccac caccctggtg     900
gtgtgcagaa gcaaggtggt ggagaccaga gtgtgcttcg agatcgagat gggcaacgag     960
cacgaggcca ccgccgtgta ctgcctgagc gtgttccaga caagctgct gcccagcgcc    1020 tggagccaga gcctggtgaa gcagatcggc ggcgagacca agggcatgcc catgagcctg    1080
aaggtgggcg tgatgagcct gcacgagaga cccgagagat acttcgacgg cctggccgac    1140
agactgaccc acgtggaccc cctggaggac tgcaaggaga ccagagtgta cgtgcagatc    1200
gaggccaccc tggagaacct ggaccccaag accagagact gcttcctggt gctgggcgcc    1260
ttccccgagg acaagaagat cccccctgga cgtgctgatca acgtgctggt ggagctgcac    1320
```

-continued

```
gacctggagg acgccaccgc cttcgccgtg atcgtggagc tggcccagca ccagctggtg   1380
agcatcgtga aggaccccaa gtacggccac gccttcagca ccttcttcga gctgtacgtg   1440
tgccagagag acgtgggcca cgacggcgcc ctgagagtga cccagcacat gaaggccaac   1500
aacaaggaca gactgctgat gcccaagaga gacagcatcc tgccccacga ctgggagaga   1560
aacaacgagg accoctggag agccaaggtg atgaccatcc acagcatcga catgagccag   1620
gtggagtact gggacgccga gatgcccaag gccgacggcc tgatcatgca cttctgcagc   1680
gacaagtggg tgctgccccc cttcgtggcc agaggcggca gagcctgcat cgtggtggcc   1740
atccagaacg gcatgagccc cgcccacctg cacgactaca gcatcttcac caacgtggcc   1800
aagctgaagt gcctgtggat caacaagatg agagtgcccg acctgaccag cagcaccgtg   1860
cccgccaaca acggcacaa gatcaccgcc atctggacca agatgcagag caccatggag   1920
aacaccgaga tcgaggccct gcaggtgtac cccaaggtga ccgaggccac catcgagaag   1980
accgacgaga tggtggagct gcccagcacc atctgcctgg cctgcagcgt gcagagcctg   2040
agcatcaccc agagccccag aatcagagag ctgcccaaga acctgagcca cgtgaaggcc   2100
ggccagctgg gcagactgtt cgcctgcaag gagctgcaga ccctgcccat cgagggctgc   2160 gagctgccc acatcagatt cgtggacatc agccagagcg tgagcctgag ctgcatcccc   2220
gagaagatcg gcaagctgaa gagcggcgac aagatggaga gccacgagac ctgcctgtgc   2280
tgcatccccc agagcggcat cggcatcacc agcatccaca gagtgatcac cgagagagac   2340
gccctgtgga tgttcgacaa ggtgaacaag atggtggcca tgatcaaggt ggacatgggc   2400
gagaagtgct tcagccacga gtgggccgag gac                                2433
```

<210> SEQ ID NO 8
<211> LENGTH: 811
<212> TYPE: PRT
<213> ORGANISM: Artificial Sequence
<220> FEATURE:
<223> OTHER INFORMATION: Amino acid sequence HCP7, variant 1

<400> SEQUENCE: 8

```
Met Ala Asp Ile Ile Gly Gly Glu Val Val Thr Glu Leu Val Arg Gln
1               5                   10                  15

Leu Tyr Ala Val Ser Gln Lys Thr Leu Arg Cys Arg Gly Ile Ala Lys
            20                  25                  30

Asn Leu Ala Thr Met Ile Asp Gly Leu Gln Pro Thr Ile Lys Glu Ile
        35                  40                  45

Gln Tyr Ser Gly Val Glu Leu Thr Pro His Arg Gln Ala Gln Leu Arg
    50                  55                  60

Met Phe Ser Glu Thr Leu Asp Lys Cys Arg Lys Leu Thr Glu Lys Val
65                  70                  75                  80

Leu Lys Ser Ser Arg Trp Asn Met Val Arg Gln Leu Leu His Val Arg
                85                  90                  95

Lys Met Glu Asn Leu Gln Ser Lys Val Ser Ser Phe Leu Asn Gly Gln
            100                 105                 110

Leu Leu Val His Val Leu Ala Asp Val His Val Arg Ala Asp Ser
        115                 120                 125

Glu Phe Arg Phe Asp Arg Ile Asp Lys Lys Val Glu Cys Leu Gln Glu
    130                 135                 140

His Leu Leu Ser Met Arg Leu Arg Gly Cys Glu Thr Leu Arg Glu Met
145                 150                 155                 160
```

Ile His Ser Leu Asp Val Cys Gly Glu Met Val Thr Thr Asp Gly Ala
                165                 170                 175

Asp Leu Gly Val Gly Leu Asp Leu Gly Lys Arg Lys Val Lys Glu Met
            180                 185                 190

Leu Phe Lys Ser Ile Asp Gly Glu Arg Leu Ile Gly Ile Ser Gly Met
        195                 200                 205

Ser Gly Ser Gly Lys Thr Thr Leu Ala Lys Glu Leu Ala Arg Asp Glu
    210                 215                 220

Glu Val Arg Gly His Phe Gly Asn Lys Val Leu Phe Leu Thr Val Ser
225                 230                 235                 240

Gln Ser Pro Asn Leu Glu Glu Leu Arg Ala His Ile Trp Gly Phe Leu
                245                 250                 255

Thr Ser Tyr Glu Ala Gly Val Gly Ala Thr Leu Pro Glu Ser Arg Lys
            260                 265                 270

Leu Val Ile Leu Asp Asp Val Trp Thr Arg Glu Ser Leu Asp Gln Leu
        275                 280                 285

Met Phe Glu Asn Ile Pro Gly Thr Thr Thr Leu Val Val Cys Arg Ser
    290                 295                 300

Lys Val Val Glu Thr Arg Val Cys Phe Glu Ile Glu Met Gly Asn Glu
305                 310                 315                 320

His Glu Ala Thr Ala Val Tyr Cys Leu Ser Val Phe Gln Asn Lys Leu
                325                 330                 335

Leu Pro Ser Ala Trp Ser Gln Ser Leu Val Lys Gln Ile Gly Gly Glu
            340                 345                 350

Thr Lys Gly Met Pro Met Ser Leu Lys Val Gly Val Met Ser Leu His
        355                 360                 365

Glu Arg Pro Glu Arg Tyr Phe Asp Gly Leu Ala Asp Arg Leu Thr His
    370                 375                 380

Val Asp Pro Leu Glu Asp Cys Lys Glu Thr Arg Val Tyr Val Gln Ile
385                 390                 395                 400

Glu Ala Thr Leu Glu Asn Leu Asp Pro Lys Thr Arg Asp Cys Phe Leu
                405                 410                 415

Val Leu Gly Ala Phe Pro Glu Asp Lys Lys Ile Pro Leu Asp Val Leu
            420                 425                 430

Ile Asn Val Leu Val Glu Leu His Asp Leu Glu Asp Ala Thr Ala Phe
        435                 440                 445

Ala Val Ile Val Glu Leu Ala Gln His Gln Leu Val Ser Ile Val Lys
    450                 455                 460

Asp Pro Lys Tyr Gly His Ala Phe Ser Thr Phe Phe Glu Leu Tyr Val
465                 470                 475                 480

Cys Gln Arg Asp Val Gly His Asp Gly Ala Leu Arg Val Thr Gln His
                485                 490                 495

Met Lys Ala Asn Asn Lys Asp Arg Leu Leu Met Pro Lys Arg Asp Ser
            500                 505                 510

Ile Leu Pro His Asp Trp Glu Arg Asn Glu Asp Pro Trp Arg Ala
        515                 520                 525

Lys Val Met Thr Ile His Ser Ile Asp Met Ser Gln Val Glu Tyr Trp
530                 535                 540

Asp Ala Glu Met Pro Lys Ala Asp Gly Leu Ile Met His Phe Cys Ser
545                 550                 555                 560

Asp Lys Trp Val Leu Pro Pro Phe Val Ala Arg Gly Gly Arg Ala Cys
            565                 570                 575

Ile Val Val Ala Ile Gln Asn Gly Met Ser Pro Ala His Leu His Asp 580             585                 590
Tyr Ser Ile Phe Thr Asn Val Ala Lys Leu Lys Cys Leu Trp Ile Asn
            595                 600                 605

Lys Met Arg Val Pro Asp Leu Thr Ser Thr Val Pro Ala Asn Asn
    610                 615                 620

Gly His Lys Ile Thr Ala Ile Trp Thr Lys Met Gln Ser Thr Met Glu
625                 630                 635                 640

Asn Thr Glu Ile Glu Ala Leu Gln Val Tyr Pro Lys Val Thr Glu Ala
                645                 650                 655

Thr Ile Glu Lys Thr Asp Glu Met Val Glu Leu Pro Ser Thr Ile Cys
            660                 665                 670

Leu Ala Cys Ser Val Gln Ser Leu Ser Ile Thr Gln Ser Pro Arg Ile
            675                 680                 685

Arg Glu Leu Pro Lys Asn Leu Ser His Val Lys Ala Gly Gln Leu Gly
            690                 695                 700

Arg Leu Phe Ala Cys Lys Glu Leu Gln Thr Leu Pro Ile Glu Gly Cys
705                 710                 715                 720

Glu Leu Pro His Ile Arg Phe Val Asp Ile Ser Gln Ser Val Ser Leu
                725                 730                 735

Ser Cys Ile Pro Glu Lys Ile Gly Lys Leu Lys Ser Gly Asp Lys Met
            740                 745                 750

Glu Ser His Glu Thr Cys Leu Cys Cys Ile Pro Gln Ser Gly Ile Gly
            755                 760                 765

Ile Thr Ser Ile His Arg Val Ile Thr Glu Arg Asp Ala Leu Trp Met
770                 775                 780

Phe Asp Lys Val Asn Lys Met Val Ala Met Ile Lys Val Asp Met Gly
785                 790                 795                 800

Glu Lys Cys Phe Ser His Glu Trp Ala Glu Asp
                805                 810

<210> SEQ ID NO 9
<211> LENGTH: 2433
<212> TYPE: DNA
<213> ORGANISM: Artificial Sequence
<220> FEATURE:
<221> NAME/KEY: source
<222> LOCATION: 1..2433
<223> OTHER INFORMATION: /organism="Artificial Sequence"
      /note="Nucleotide sequence HCP7, variant 2"
      /mol_type="unassigned DNA"

<400> SEQUENCE: 9
atggccgaca tcatcggcgg cgaggtggtg accgagctgg tgagacagct gtacgccgtg      60
agccagaaga ccctgagatg cagaggcatc gccaagaacc tggccaccat gatcgacggc     120
ctgcagccca ccatcaagga gatccagtac agcggcgtgg agctgacccc ccacagacag     180
gcccagctga atgttcag cgagaccctg acaagtgca gaaagctgac cgagaaggtg        240
ctgaagagca gcagatggaa catggtgaga cagctgctgc acgtgagaaa gatggagaac     300
ctgcagagca aggtgagcag cttcctgaac ggccagctgc tggtgcacgt gctggccgac     360
gtgcaccacg tgagagccga cagcgagttc agattcgaca gaatcgacag aaagctggac     420
tgcctgcagg agaagctggg ctgcatgaag ctgagactga gcgacagcct gagagaggtg     480
atcaagaccg ccgaggccac cctggagatg gtgaccaccg acggcgccga cctgggcgtg     540
ggcctggacc tgggcaagag aaaggtgaag gagatgctgt tcaagagcat cgacggcgag     600
agactgatcg gcatcagcgg catgagcggc agcggcaaga ccaccctggc caaggagctg     660

```
gccagagacg aggaggtgag aggccacttc ggcaacaagg tgctgttcct gaccgtgagc    720
cagagcccca acctggagga gctgagagcc cacatctggg gcttcctgac cagctacgag    780
gccggcgtgg gcgccaccct gcccgagagc agaaagctgg tgatcctgga cgacgtgtgg    840
accagagaga gcctggacca gctgatgttc gagaacatcc ccggcaccac caccctggtg    900
gtgagcagaa gcaagggcgc cgagtgccac gtgacctggg acgtggacct gatgaacgag    960
cacgaggcca ccgccctgtt cagcgccacc ctgtacaacc agaagctggt gcccagcggc   1020
tggagccaga gcctggtgag acaggtggtg ggcgactgcc acggcgtgcc cgccagcctg   1080
cacgtgatcg gcgtgaccat caaggagaga cccgacagat acttcgacat ggccctggag   1140
agactgagca gaggcgaccc cgccgaggag acccacgaca ccaagggctt cgccaacatc   1200
gaggccaccc tggagaacct ggaccccaag accagagact gcttcctggt gctgggcgcc   1260
ttccccgagg acaagaagat ccccctggac gtgctgatca acgtgctggt ggagctgcac   1320
gacctggagg acgccaccgc cttcgccgtg atcgtggaga tcgcccagag aaacatcctg   1380
accctgatga aggaccccag attcgtgcac gcctggagca cctactacga catctacgtg   1440
acccagaagg aggtgctgaa ggaggtggcc ctgagactga gcaacagagg caagatgaac   1500
aacagagaca gagccatcat gcccaagcac gagagcatgg tgcccaagga gttcgagaga   1560
cagcaggagg agccctggaa gggcagaatc gtgagcgcca gatgcggcga gatgacccag   1620
atggactggt tcgagatgga cctgccccac gccgaggtga tgctgctgag atactgcagc   1680
gagagattcg tgctgccccc ctggatcatc aagatgatca gactgaccgc cctggtgatc   1740
ctgaaccagc tggtgagccc catgagactg cacgagttca gcatctggag ccagctggcc   1800
aagctgagat gcctgttcct gcagagaggc agaatgcccg acctgaccag cacctgcgtg   1860
cccctgcagc aggtgaagca cctgagcctg atcttctgca gaatccagag cagcctggac   1920
aactgcgacc tggacgccat ccaggtgttc cccagactgt gcgagctgac catcgacaga   1980
tgcgacgaga tgctggagct gcccacctgc atcagcgccc tgaccagcct gcagagcatc   2040
agcggctgca actgccccaa gatcaaggag gcccccaagc agatctgcag actgcacatg   2100
gcccagctgc tgcacctgta cgcctgcaag gaggtgcaga ccctgcccgt ggaggtgtgc   2160 gacgccccec acctgaagtg gctggacatc tgccagtgcg tgagcgtgtg caccatcccc   2220
gagaagatcg tgcacctgaa gtgcgtggag cacatcgaca gcagagactg ctgcgccagc   2280
accatcccca cagcgtgggg catcctgacc agcctgagac acggcatcac cgagagagag   2340
gccctgtggc tgtgggagca cgtgcagaag ggcggcatcg tggtgagagt ggagatcgtg   2400
gacagaagct tctgcagaga ctggctggac gag                                 2433
```

<210> SEQ ID NO 10
<211> LENGTH: 811
<212> TYPE: PRT
<213> ORGANISM: Artificial Sequence
<220> FEATURE:
<223> OTHER INFORMATION: Amino acid sequence HCP7, variant 2

<400> SEQUENCE: 10

```
Met Ala Asp Ile Ile Gly Gly Glu Val Val Thr Glu Leu Val Arg Gln
1               5                   10                  15

Leu Tyr Ala Val Ser Gln Lys Thr Leu Arg Cys Arg Gly Ile Ala Lys
            20                  25                  30

Asn Leu Ala Thr Met Ile Asp Gly Leu Gln Pro Thr Ile Lys Glu Ile
        35                  40                  45
```

```
Gln Tyr Ser Gly Val Glu Leu Thr Pro His Arg Gln Ala Gln Leu Arg
 50                  55                  60

Met Phe Ser Glu Thr Leu Asp Lys Cys Arg Lys Leu Thr Glu Lys Val
 65                  70                  75                  80

Leu Lys Ser Ser Arg Trp Asn Met Val Arg Gln Leu Leu His Val Arg
                 85                  90                  95

Lys Met Glu Asn Leu Gln Ser Lys Val Ser Ser Phe Leu Asn Gly Gln
                100                 105                 110

Leu Leu Val His Val Leu Ala Asp Val His His Val Arg Ala Asp Ser
            115                 120                 125

Glu Phe Arg Phe Asp Arg Ile Asp Arg Lys Leu Asp Cys Leu Gln Glu
            130                 135                 140

Lys Leu Gly Cys Met Lys Leu Arg Leu Ser Asp Ser Leu Arg Glu Val
145                 150                 155                 160

Ile Lys Thr Ala Glu Ala Thr Leu Glu Met Val Thr Thr Asp Gly Ala
                165                 170                 175

Asp Leu Gly Val Gly Leu Asp Leu Gly Lys Arg Lys Val Lys Glu Met
            180                 185                 190

Leu Phe Lys Ser Ile Asp Gly Glu Arg Leu Ile Gly Ile Ser Gly Met
            195                 200                 205

Ser Gly Ser Gly Lys Thr Thr Leu Ala Lys Glu Leu Ala Arg Asp Glu
210                 215                 220

Glu Val Arg Gly His Phe Gly Asn Lys Val Leu Phe Leu Thr Val Ser
225                 230                 235                 240

Gln Ser Pro Asn Leu Glu Glu Leu Arg Ala His Ile Trp Gly Phe Leu
                245                 250                 255

Thr Ser Tyr Glu Ala Gly Val Gly Ala Thr Leu Pro Glu Ser Arg Lys
            260                 265                 270

Leu Val Ile Leu Asp Asp Val Trp Thr Arg Glu Ser Leu Asp Gln Leu
            275                 280                 285

Met Phe Glu Asn Ile Pro Gly Thr Thr Thr Leu Val Val Ser Arg Ser
290                 295                 300

Lys Gly Ala Glu Cys His Val Thr Trp Asp Val Asp Leu Met Asn Glu
305                 310                 315                 320

His Glu Ala Thr Ala Leu Phe Ser Ala Thr Leu Tyr Asn Gln Lys Leu
                325                 330                 335

Val Pro Ser Gly Trp Ser Gln Ser Leu Val Arg Gln Val Val Gly Asp
            340                 345                 350

Cys His Gly Val Pro Ala Ser Leu His Val Ile Gly Val Thr Ile Lys
            355                 360                 365

Glu Arg Pro Asp Arg Tyr Phe Asp Met Ala Leu Glu Arg Leu Ser Arg
            370                 375                 380

Gly Asp Pro Ala Glu Glu Thr His Asp Thr Lys Gly Phe Ala Asn Ile
385                 390                 395                 400

Glu Ala Thr Leu Glu Asn Leu Asp Pro Lys Thr Arg Asp Cys Phe Leu
                405                 410                 415

Val Leu Gly Ala Phe Pro Glu Asp Lys Lys Ile Pro Leu Asp Val Leu
            420                 425                 430

Ile Asn Val Leu Val Glu Leu His Asp Leu Glu Asp Ala Thr Ala Phe
            435                 440                 445

Ala Val Ile Val Glu Ile Ala Gln Arg Asn Ile Leu Thr Leu Met Lys
450                 455                 460
```

Asp Pro Arg Phe Val His Ala Trp Ser Thr Tyr Tyr Asp Ile Tyr Val
465                 470                 475                 480

Thr Gln Lys Glu Val Leu Lys Glu Val Ala Leu Arg Leu Ser Asn Arg
            485                 490                 495

Gly Lys Met Asn Asn Arg Asp Arg Ala Ile Met Pro Lys His Glu Ser
        500                 505                 510

Met Val Pro Lys Glu Phe Glu Arg Gln Gln Glu Pro Trp Lys Gly
    515                 520                 525

Arg Ile Val Ser Ala Arg Cys Gly Glu Met Thr Gln Met Asp Trp Phe
    530                 535                 540

Glu Met Asp Leu Pro His Ala Glu Val Met Leu Leu Arg Tyr Cys Ser
545                 550                 555                 560

Glu Arg Phe Val Leu Pro Pro Trp Ile Ile Lys Met Ile Arg Leu Thr
                565                 570                 575

Ala Leu Val Ile Leu Asn Gln Leu Val Ser Pro Met Arg Leu His Glu
                580                 585                 590

Phe Ser Ile Trp Ser Gln Leu Ala Lys Leu Arg Cys Leu Phe Leu Gln
            595                 600                 605

Arg Gly Arg Met Pro Asp Leu Thr Ser Thr Cys Val Pro Leu Gln Gln
    610                 615                 620

Val Lys His Leu Ser Leu Ile Phe Cys Arg Ile Gln Ser Ser Leu Asp
625                 630                 635                 640

Asn Cys Asp Leu Asp Ala Ile Gln Val Phe Pro Arg Leu Cys Glu Leu
                645                 650                 655

Thr Ile Asp Arg Cys Asp Glu Met Leu Glu Leu Pro Thr Cys Ile Ser
                660                 665                 670

Ala Leu Thr Ser Leu Gln Ser Ile Ser Gly Cys Asn Cys Pro Lys Ile
            675                 680                 685

Lys Glu Ala Pro Lys Gln Ile Cys Arg Leu His Met Ala Gln Leu Leu
    690                 695                 700

His Leu Tyr Ala Cys Lys Glu Val Gln Thr Leu Pro Val Glu Val Cys
705                 710                 715                 720

Asp Ala Pro His Leu Lys Trp Leu Asp Ile Cys Gln Cys Val Ser Val
                725                 730                 735

Cys Thr Ile Pro Glu Lys Ile Val His Leu Lys Cys Val Glu His Ile
                740                 745                 750

Asp Ser Arg Asp Cys Cys Ala Ser Thr Ile Pro Asn Ser Val Gly Ile
            755                 760                 765

Leu Thr Ser Leu Arg His Gly Ile Thr Glu Arg Glu Ala Leu Trp Leu
    770                 775                 780

Trp Glu His Val Gln Lys Gly Gly Ile Val Val Arg Val Glu Ile Val
785                 790                 795                 800

Asp Arg Ser Phe Cys Arg Asp Trp Leu Asp Glu
                805                 810

<210> SEQ ID NO 11
<211> LENGTH: 2433
<212> TYPE: DNA
<213> ORGANISM: Artificial Sequence
<220> FEATURE:
<221> NAME/KEY: source
<222> LOCATION: 1..2433
<223> OTHER INFORMATION: /organism="Artificial Sequence"
      /note="Nucleotide sequence HCP7, variant 3"
      /mol_type="unassigned DNA"

<400> SEQUENCE: 11

```
atggccgaca tcatcggcgg cgaggtggtg accgagctgg tgagacagct gtacgccgtg        60
agccagaaga ccctgagatg cagaggcatc gccaagaacc tggccaccat gatcgacggc       120
ctgcagccca ccatcaagga gatccagtac agcggcgtgg agctgacccc ccacagacag       180
gcccagctga gaatgttcag cgagaccctg acaagtgcag aaagctgacc gagaaggtg        240 ctgaagagca gcagatggaa catggtgaga cagctgctgc acgtgagaaa gatggagaac       300
ctgcagagca aggtgagcag cttcctgaac ggccagctgc tggtgcacgt gctggccgac       360
gtgcaccacg tgagagccga cagcgagttc agattcgaca gaatcgacca caaggtggac       420
agcctgaacg acaagctggg cagcggcaga gccagaggca gcgagagcgt gagagagatg       480
ctgaagagcg ccgacgcctg cgtggagatg gtgaccaccg acggcgccga cctgggcgtg       540
ggcctggacc tgggcaagag aaaggtgaag gagatgctgt tcaagagcat cgacggcgag       600
agactgatcg gcatcagcgg catgagcggc agcggcaaga ccaccctggc caaggagctg       660
gccagagacg aggaggtgag aggccacttc ggcaacaagg tgctgttcct gaccgtgagc       720
cagagcccca acctggagga gctgagagcc cacatctggg gcttcctgac cagctacgag       780
gccggcgtgg gcgccaccct gcccgagagc agaaagctgg tgatcctgga cgacgtgtgg       840
accagagaga gcctggacca gctgatgttc gagaacatcc ccggcaccac caccctggtg       900
gtgtgcagaa gcaagctggg cgagtgcaga atgacctacg acgtggacat gctgcaggag       960
cacgacgcca ccggcctgtt caccctgagc gtgttcaacc agaagctggt gcccagcgtg      1020
tacacccaga gcctggtgaa gcagctggtg atggagagca gaggcctgcc cggcagcctg      1080
aagatgatca tcgccagcgt gcacgacaga cccgagaagt actgggaggt gctggtggag      1140
agactgagca gaggcgagcc cgccgaggac accaaggaca gcagagtgtt cgccaacatc      1200
gaggccaccc tggagaacct ggaccccaag accagagact gcttcctggt gctgggcgcc      1260
ttccccgagg acaagaagat ccccctggac gtgctgatca acgtgctggt ggagctgcac      1320
gacctggagg acgccaccgc cttcgccgtg atcatggagc tgcccagag acaggtgctg      1380 agcatcgtgc acgaccccag attcgtgcac atgtggacca cctggttcga cgtgttcgtg      1440
acccagcacg acgccctgca cgacgtgatg ctgagaatca ccaaccacgc ccacctgaac      1500
cagagagacc acctgatcat gcccagaaga gagagcctgc tgccccacga gtgggagaga      1560
aaccaggacg acccctacag agtgagagcc gtgagcatcc acaccggcga gatgagccag      1620
atggagtact tcgacgccga cctgcccaag gccgaggtgc tggtgctgca ctacagctgc      1680
gagagatacc tgatccccccc cttcatcgcc aagatgatga cctgagcct gggcgtgatc      1740 ggccagaacg gcgccagccc cgccagactg cacgagttca gcatcttcac caacctgatg      1800
aagctgaaga gcctgtggct gaacagagtg cacatgcccg agctgagcag cagctgcgtg      1860
cccctgcaga acgtgcacaa gggcagcctg atcttcaccc acatccagac cagcgtggac      1920
cagaccgagc tggacatcgc ccaggccttc cccaaggtga gcgagctgag catcgagcac      1980
tgcgaggacc tgctggagat ccctgcacc atcagcggca tcaccagcct gcagagcatc      2040
agcatcacca actgccccag aatcagagag gtgcccaagc agctgagcag actgaaggcc      2100
ctgcagctgc tgagactgta cgcctgcaag gagctgaact gcatgccat ggagatctgc      2160 gacctgccca gctgcactga cgtggagatc agcaacagcg tgaccctgtg cagcatcccc      2220
gacaaggccg gcaaggtgaa gagcctggag aagatcgact gcagagactg cagcctgagc      2280
agcgccccca acagcgtggt gctgctgacc agcctgagac acgtggtgtg cgagaaggac      2340
```

```
gccggctacg cctgggagaa ggcccagcac ggcgtgctgg gcctgaaggt ggaggtggcc      2400
gacaagagct ggaccagaga cttcctggac gag                                   2433

<210> SEQ ID NO 12
<211> LENGTH: 811
<212> TYPE: PRT
<213> ORGANISM: Artificial Sequence
<220> FEATURE:
<223> OTHER INFORMATION: Amino acid sequence HCP7, variant 3

<400> SEQUENCE: 12
```

Met Ala Asp Ile Ile Gly Gly Glu Val Thr Glu Leu Val Arg Gln
1               5                   10                  15

Leu Tyr Ala Val Ser Gln Lys Thr Leu Arg Cys Arg Gly Ile Ala Lys
            20                  25                  30

Asn Leu Ala Thr Met Ile Asp Gly Leu Gln Pro Thr Ile Lys Glu Ile
        35                  40                  45

Gln Tyr Ser Gly Val Glu Leu Thr Pro His Arg Gln Ala Gln Leu Arg
    50                  55                  60

Met Phe Ser Glu Thr Leu Asp Lys Cys Arg Lys Leu Thr Glu Lys Val
65                  70                  75                  80

Leu Lys Ser Ser Arg Trp Asn Met Val Arg Gln Leu Leu His Val Arg
                85                  90                  95

Lys Met Glu Asn Leu Gln Ser Lys Val Ser Ser Phe Leu Asn Gly Gln
            100                 105                 110

Leu Leu Val His Val Leu Ala Asp Val His His Val Arg Ala Asp Ser
        115                 120                 125

Glu Phe Arg Phe Asp Arg Ile Asp His Lys Val Asp Ser Leu Asn Asp
    130                 135                 140

Lys Leu Gly Ser Gly Arg Ala Arg Gly Ser Glu Ser Val Arg Glu Met
145                 150                 155                 160

Leu Lys Ser Ala Asp Ala Cys Val Glu Met Val Thr Thr Asp Gly Ala
                165                 170                 175

Asp Leu Gly Val Gly Leu Asp Leu Gly Lys Arg Lys Val Lys Glu Met
            180                 185                 190

Leu Phe Lys Ser Ile Asp Gly Glu Arg Leu Ile Gly Ile Ser Gly Met
        195                 200                 205

Ser Gly Ser Gly Lys Thr Thr Leu Ala Lys Glu Leu Ala Arg Asp Glu
    210                 215                 220

Glu Val Arg Gly His Phe Gly Asn Lys Val Leu Phe Leu Thr Val Ser
225                 230                 235                 240

Gln Ser Pro Asn Leu Glu Glu Leu Arg Ala His Ile Trp Gly Phe Leu
                245                 250                 255

Thr Ser Tyr Glu Ala Gly Val Gly Ala Thr Leu Pro Glu Ser Arg Lys
            260                 265                 270

Leu Val Ile Leu Asp Asp Val Trp Thr Arg Glu Ser Leu Asp Gln Leu
        275                 280                 285

Met Phe Glu Asn Ile Pro Gly Thr Thr Thr Leu Val Val Cys Arg Ser
    290                 295                 300

Lys Leu Gly Glu Cys Arg Met Thr Tyr Asp Val Asp Met Leu Gln Glu
305                 310                 315                 320

His Asp Ala Thr Gly Leu Phe Thr Leu Ser Val Phe Asn Gln Lys Leu
                325                 330                 335

Val Pro Ser Val Tyr Thr Gln Ser Leu Val Lys Gln Leu Val Met Glu
            340                 345                 350

```
Ser Arg Gly Leu Pro Gly Ser Leu Lys Met Ile Ile Ala Ser Val His
    355                 360                 365

Asp Arg Pro Glu Lys Tyr Trp Glu Val Leu Val Glu Arg Leu Ser Arg
    370                 375                 380

Gly Glu Pro Ala Glu Asp Thr Lys Asp Ser Arg Val Phe Ala Asn Ile
385                 390                 395                 400

Glu Ala Thr Leu Glu Asn Leu Asp Pro Lys Thr Arg Asp Cys Phe Leu
                405                 410                 415

Val Leu Gly Ala Phe Pro Glu Asp Lys Lys Ile Pro Leu Asp Val Leu
            420                 425                 430

Ile Asn Val Leu Val Glu Leu His Asp Leu Glu Asp Ala Thr Ala Phe
        435                 440                 445

Ala Val Ile Met Glu Leu Ala Gln Arg Gln Val Leu Ser Ile Val His
    450                 455                 460

Asp Pro Arg Phe Val His Met Trp Thr Thr Trp Phe Asp Val Phe Val
465                 470                 475                 480

Thr Gln His Asp Ala Leu His Asp Val Met Leu Arg Ile Thr Asn His
                485                 490                 495

Ala His Leu Asn Gln Arg Asp His Leu Ile Met Pro Arg Arg Glu Ser
            500                 505                 510

Leu Leu Pro His Glu Trp Glu Arg Asn Gln Asp Asp Pro Tyr Arg Val
        515                 520                 525

Arg Ala Val Ser Ile His Thr Gly Glu Met Ser Gln Met Glu Tyr Phe
    530                 535                 540

Asp Ala Asp Leu Pro Lys Ala Glu Val Leu Val Leu His Tyr Ser Cys
545                 550                 555                 560

Glu Arg Tyr Leu Ile Pro Pro Phe Ile Ala Lys Met Met His Leu Ser
                565                 570                 575

Leu Gly Val Ile Gly Gln Asn Gly Ala Ser Pro Ala Arg Leu His Glu
            580                 585                 590

Phe Ser Ile Phe Thr Asn Leu Met Lys Leu Lys Ser Leu Trp Leu Asn
        595                 600                 605

Arg Val His Met Pro Glu Leu Ser Ser Ser Cys Val Pro Leu Gln Asn
    610                 615                 620

Val His Lys Gly Ser Leu Ile Phe Thr His Ile Gln Thr Ser Val Asp
625                 630                 635                 640

Gln Thr Glu Leu Asp Ile Ala Gln Ala Phe Pro Lys Val Ser Glu Leu
                645                 650                 655

Ser Ile Glu His Cys Glu Asp Leu Leu Glu Ile Pro Cys Thr Ile Ser
            660                 665                 670

Gly Ile Thr Ser Leu Gln Ser Ile Ser Ile Thr Asn Cys Pro Arg Ile
        675                 680                 685

Arg Glu Val Pro Lys Gln Leu Ser Arg Leu Lys Ala Leu Gln Leu Leu
    690                 695                 700

Arg Leu Tyr Ala Cys Lys Glu Leu Asn Cys Met Pro Met Glu Ile Cys
705                 710                 715                 720

Asp Leu Pro Lys Leu His Tyr Val Glu Ile Ser Asn Ser Val Thr Leu
                725                 730                 735

Cys Ser Ile Pro Asp Lys Ala Gly Lys Val Lys Ser Leu Glu Lys Ile
            740                 745                 750

Asp Cys Arg Asp Cys Ser Leu Ser Ser Ala Pro Asn Ser Val Val Leu
        755                 760                 765
```

Leu Thr Ser Leu Arg His Val Val Cys Glu Lys Asp Ala Gly Tyr Ala
            770                 775                 780

Trp Glu Lys Ala Gln His Gly Val Leu Gly Leu Lys Val Glu Val Ala
785                 790                 795                 800

Asp Lys Ser Trp Thr Arg Asp Phe Leu Asp Glu
                805                 810

<210> SEQ ID NO 13
<211> LENGTH: 2433
<212> TYPE: DNA
<213> ORGANISM: Artificial Sequence
<220> FEATURE:
<221> NAME/KEY: source
<222> LOCATION: 1..2433
<223> OTHER INFORMATION: /organism="Artificial Sequence"
     /note="Nucleotide sequence HCP7, variant 4"
     /mol_type="unassigned DNA"

<400> SEQUENCE: 13

| | | | | | |
|---|---|---|---|---|---|
| atggccgaca | tcatcggcgg | cgaggtggtg | accgagctgg | tgagacagct | gtacgccgtg | 60 |
| agccagaaga | ccctgagatg | cagaggcatc | gccaagaacc | tggccaccat | gatcgacggc | 120 |
| ctgcagccca | ccatcaagga | gatccagtac | agcggcgtgg | agctgacccc | ccacagacag | 180 |
| gcccagctga | gaatgttcag | cgagaccctg | gacaagtgca | gaaagctgac | cgagaaggtg | 240 |
| ctgaagagca | gcagatggaa | catggtgaga | cagctgctgc | acgtgagaaa | gatggagaac | 300 |
| ctgcagagca | aggtgagcag | cttcctgaac | ggccagctgc | tggtgcacgt | gctggccgac | 360 |
| gtgcaccacg | tgagagccga | cagcgagttc | agattcgaca | gaatcgacag | aaaggtggac | 420 |
| agcctgcagg | agcacatcat | caccatgcac | ctgagaggca | ccgacagcct | gaaggaggcc | 480 |
| ctgaagaccg | ccgaggccac | catcgagatg | gtgaccaccg | acggcgccga | cctgggcgtg | 540 |
| ggcctggacc | tgggcaagag | aaaggtgaag | gagatgctgt | tcaagagcat | cgacggcgag | 600 |
| agactgatcg | gcatcagcgg | catgagcggc | agcggcaaga | ccaccctggc | caaggagctg | 660 |
| gccagagacg | aggaggtgag | aggccacttc | ggcaacaagg | tgctgttcct | gaccgtgagc | 720 |
| cagagcccca | acctggagga | gctgagagcc | cacatctggg | gcttcctgac | cagctacgag | 780 |
| gccggcgtgg | gcgccaccct | gcccgagagc | agaaagctgg | tgatcctgga | cgacgtgtgg | 840 |
| accagagaga | gcctggacca | gctgatgttc | gagaacatcc | ccggcaccac | caccctggtg | 900 |
| gtgagcagaa | gcaagctgct | ggacaccaga | gtgtgcttcg | acgccgacct | gggccaggag | 960 |
| cacgaggtga | gcgccctgtt | ctgcgccagc | gtgtacaacc | agaagctggt | gcccagcggc | 1020 |
| ttcacccaga | gcggcgtgaa | gcaggtggtg | ggcgagtgca | agctgctgcc | cctgagcatc | 1080 |
| aagatgatcg | gcgccagcct | gaaggacaga | cccgagaagt | actgggaggg | cctggtggag | 1140 |
| agactgagcg | aggcgagcc | cctggacgag | acccacgaga | gcaaggtgtt | cgcccagatc | 1200 |
| gaggccaccc | tggagaacct | ggaccccaag | accagagact | gcttcctggt | gctgggcgcc | 1260 |
| ttccccgagg | acaagaagat | ccccctggac | gtgctgatca | acgtgctggt | ggagctgcac | 1320 |
| gacctggagg | acgccaccgc | cttcgccgtg | atcgtggacc | tggcccagca | caacgtgggc | 1380 |
| accatggtga | aggaccccag | attcggccac | atgtggtgca | cctactacga | cctgttcgtg | 1440 |
| accaaccacg | acatcctgag | agacctggcc | ggcagactga | gcaaccacat | gcacggcaac | 1500 |
| aaccacgaga | gactgctgat | gcccaagaga | gagtgcatga | tccccagaga | gtgggagaga | 1560 |
| aaccaggacg | acccctacaa | ggccagactg | gtgagcatcc | acaccggcga | gctgaccaac | 1620 |
| atcgactggt | tcgacatgga | gctgcccac | gccgacgtgc | tgatcctgca | cttcagcagc | 1680 |

```
gagaagtacg tgctgccccc ctggatcgcc cacatgggca agctgaccgc cctggtgatc    1740
atcaacaacg gcatgagccc cgccagactg cacgacttca ccgcctacac ccagctggcc    1800
aagatgaagt gcctgtggat ccagagagtg aaggtgcccg aggtgagcag cagcaccgcc    1860
cccctgcaga acggccacaa gctgtgcggc atctggtgca agctgaacac cagcgtggac    1920
cagaccgagc tggacatcgc ccagatctgg ccccacctga gcgacctgac catcgaccac    1980
tgcgacgacc tgctggagct gcccaccacc atcagcggca tcaccagcgg ccagagcatc    2040
agcatctgca actgccccag aatcaaggag ctgcccagaa acctgagcag actgagagcc    2100
ctgcagctgc tgagaatgta cgcctgccac gagctgcaga gcctgcccgt ggacatctgc    2160
gagatgccca gactgagata cgtggacatc acccagtgcg tgaccgtgag caccctgccc    2220
gagagaatcg gcaaggtgaa gtgcctggac aagatcgaca ccagagagtg cagcctgagc    2280
agcatccccc agagcggcgg catcctgtgc agcctgagac acggcgcctg cgacagagag    2340
gccgcctgga tctgggagaa ggtgcagcac atggtgggcg gcctgagagt ggaggccgcc    2400
gagaagagct tctgcaagga ctggctggag gag                                 2433
```

<210> SEQ ID NO 14
<211> LENGTH: 811
<212> TYPE: PRT
<213> ORGANISM: Artificial Sequence
<220> FEATURE:
<223> OTHER INFORMATION: Amino acid sequence HCP7, variant 4

<400> SEQUENCE: 14

```
Met Ala Asp Ile Ile Gly Gly Glu Val Val Thr Glu Leu Val Arg Gln
1               5                   10                  15

Leu Tyr Ala Val Ser Gln Lys Thr Leu Arg Cys Arg Gly Ile Ala Lys
            20                  25                  30

Asn Leu Ala Thr Met Ile Asp Gly Leu Gln Pro Thr Ile Lys Glu Ile
        35                  40                  45

Gln Tyr Ser Gly Val Glu Leu Thr Pro His Arg Gln Ala Gln Leu Arg
    50                  55                  60

Met Phe Ser Glu Thr Leu Asp Lys Cys Arg Lys Leu Thr Glu Lys Val
65                  70                  75                  80

Leu Lys Ser Ser Arg Trp Asn Met Val Arg Gln Leu Leu His Val Arg
                85                  90                  95

Lys Met Glu Asn Leu Gln Ser Lys Val Ser Ser Phe Leu Asn Gly Gln
            100                 105                 110

Leu Leu Val His Val Leu Ala Asp Val His His Val Arg Ala Asp Ser
        115                 120                 125

Glu Phe Arg Phe Asp Arg Ile Asp Arg Lys Val Asp Ser Leu Gln Glu
    130                 135                 140

His Ile Ile Thr Met His Leu Arg Gly Thr Asp Ser Leu Lys Glu Ala
145                 150                 155                 160

Leu Lys Thr Ala Glu Ala Thr Ile Glu Met Val Thr Thr Asp Gly Ala
                165                 170                 175

Asp Leu Gly Val Gly Leu Asp Leu Gly Lys Arg Lys Val Lys Glu Met
            180                 185                 190

Leu Phe Lys Ser Ile Asp Gly Glu Arg Leu Ile Gly Ile Ser Gly Met
        195                 200                 205

Ser Gly Ser Gly Lys Thr Thr Leu Ala Lys Glu Leu Ala Arg Asp Glu
    210                 215                 220

Glu Val Arg Gly His Phe Gly Asn Lys Val Leu Phe Leu Thr Val Ser
```

```
            225                 230                 235                 240
Gln Ser Pro Asn Leu Glu Glu Leu Arg Ala His Ile Trp Gly Phe Leu
            245                 250                 255

Thr Ser Tyr Glu Ala Gly Val Gly Ala Thr Leu Pro Glu Ser Arg Lys
            260                 265                 270

Leu Val Ile Leu Asp Asp Val Trp Thr Arg Glu Ser Leu Asp Gln Leu
            275                 280                 285

Met Phe Glu Asn Ile Pro Gly Thr Thr Thr Leu Val Val Ser Arg Ser
290                 295                 300

Lys Leu Leu Asp Thr Arg Val Cys Phe Asp Ala Asp Leu Gly Gln Glu
305                 310                 315                 320

His Glu Val Ser Ala Leu Phe Cys Ala Ser Val Tyr Asn Gln Lys Leu
                    325                 330                 335

Val Pro Ser Gly Phe Thr Gln Ser Gly Val Lys Gln Val Val Gly Glu
                    340                 345                 350

Cys Lys Leu Leu Pro Leu Ser Ile Lys Met Ile Gly Ala Ser Leu Lys
                    355                 360                 365

Asp Arg Pro Glu Lys Tyr Trp Glu Gly Leu Val Glu Arg Leu Ser Arg
                    370                 375                 380

Gly Glu Pro Leu Asp Glu Thr His Glu Ser Lys Val Phe Ala Gln Ile
385                 390                 395                 400

Glu Ala Thr Leu Glu Asn Leu Asp Pro Lys Thr Arg Asp Cys Phe Leu
                    405                 410                 415

Val Leu Gly Ala Phe Pro Glu Asp Lys Lys Ile Pro Leu Asp Val Leu
                    420                 425                 430

Ile Asn Val Leu Val Glu Leu His Asp Leu Glu Asp Ala Thr Ala Phe
                    435                 440                 445

Ala Val Ile Val Asp Leu Ala Gln His Asn Val Gly Thr Met Val Lys
                    450                 455                 460

Asp Pro Arg Phe Gly His Met Trp Cys Thr Tyr Tyr Asp Leu Phe Val
465                 470                 475                 480

Thr Asn His Asp Ile Leu Arg Asp Leu Ala Gly Arg Leu Ser Asn His
                    485                 490                 495

Met His Gly Asn Asn His Glu Arg Leu Leu Met Pro Lys Arg Glu Cys
                    500                 505                 510

Met Ile Pro Arg Glu Trp Glu Arg Asn Gln Asp Asp Pro Tyr Lys Ala
                    515                 520                 525

Arg Leu Val Ser Ile His Thr Gly Glu Leu Thr Asn Ile Asp Trp Phe
                    530                 535                 540

Asp Met Glu Leu Pro His Ala Asp Val Leu Ile Leu His Phe Ser Ser
545                 550                 555                 560

Glu Lys Tyr Val Leu Pro Pro Trp Ile Ala His Met Gly Lys Leu Thr
                    565                 570                 575

Ala Leu Val Ile Ile Asn Asn Gly Met Ser Pro Ala Arg Leu His Asp
                    580                 585                 590

Phe Thr Ala Tyr Thr Gln Leu Ala Lys Met Lys Cys Leu Trp Ile Gln
                    595                 600                 605

Arg Val Lys Val Pro Glu Val Ser Ser Ser Thr Ala Pro Leu Gln Asn
                    610                 615                 620

Gly His Lys Leu Cys Gly Ile Trp Cys Lys Leu Asn Thr Ser Val Asp
625                 630                 635                 640

Gln Thr Glu Leu Asp Ile Ala Gln Ile Trp Pro His Leu Ser Asp Leu
                    645                 650                 655
```

Thr Ile Asp His Cys Asp Asp Leu Leu Glu Leu Pro Thr Thr Ile Ser
        660                 665                 670

Gly Ile Thr Ser Gly Gln Ser Ile Ser Ile Cys Asn Cys Pro Arg Ile
        675                 680                 685

Lys Glu Leu Pro Arg Asn Leu Ser Arg Leu Arg Ala Leu Gln Leu Leu
        690                 695                 700

Arg Met Tyr Ala Cys His Glu Leu Gln Ser Leu Pro Val Asp Ile Cys
705                 710                 715                 720

Glu Met Pro Arg Leu Arg Tyr Val Asp Ile Thr Gln Cys Val Thr Val
                725                 730                 735

Ser Thr Leu Pro Glu Arg Ile Gly Lys Val Lys Cys Leu Asp Lys Ile
            740                 745                 750

Asp Thr Arg Glu Cys Ser Leu Ser Ser Ile Pro Gln Ser Gly Gly Ile
        755                 760                 765

Leu Cys Ser Leu Arg His Gly Ala Cys Asp Arg Glu Ala Ala Trp Ile
    770                 775                 780

Trp Glu Lys Val Gln His Met Val Gly Gly Leu Arg Val Glu Ala Ala
785                 790                 795                 800

Glu Lys Ser Phe Cys Lys Asp Trp Leu Glu Glu
                805                 810

<210> SEQ ID NO 15
<211> LENGTH: 2433
<212> TYPE: DNA
<213> ORGANISM: Artificial Sequence
<220> FEATURE:
<221> NAME/KEY: source
<222> LOCATION: 1..2433
<223> OTHER INFORMATION: /organism="Artificial Sequence"
    /note="Nucleotide sequence HCP7, variant 5"
    /mol_type="unassigned DNA"

<400> SEQUENCE: 15
atggccgaca tcatcggcgg cgaggtggtg accgagctgg tgagacagct gtacgccgtg      60
agccagaaga ccctgagatg cagaggcatc gccaagaacc tggccaccat gatcgacggc     120
ctgcagccca ccatcaagga gatccagtac agcggcgtgg agctgacccc ccacagacag     180
gcccagctga atgttcag cgagaccctg acaagtgca gaaagctgac cgagaaggtg        240
ctgaagagca gcagatggaa catggtgaga cagctgctgc acgtgagaaa gatggagaac     300
ctgcagagca aggtgagcag cttcctgaac ggccagctgc tggtgcacgt gctggccgac     360
gtgcaccacg tgagagccga cagcgagttc agattcgaca gaatcgacag aaaggtggac     420
tgcctgaacg agaagctggg cagcatgaag ctgagaggca gcgagaccct gagagaggcc     480
ggcaagaccg ccgacgcctg cgtggagatg gtgaccaccg acggcgccga cctgggcgtg     540
ggcctggacc tgggcaagag aaaggtgaag gagatgctgt caagagcat cgacggcgag      600 agactgatcg gcatcagcgg catgagcggc agcggcaaga ccaccctggc caaggagctg     660
gccagagacg aggaggtgag aggccacttc ggcaacaagg tgctgttcct gaccgtgagc     720
cagagcccca acctggagga gctgagagcc cacatctggg gcttcctgac cagctacgag     780
gccggcgtgg gcgccaccct gcccgagagc agaaagctgg tgatcctgga cgacgtgtgg     840
accagagaga gcctggacca gctgatgttc gagaacatcc ccggcaccac caccctggtg     900
gtgaccagat gccacatcgc cgacaccaga gtgacctacg acgtggacct gctgaacgag     960
cacgaggcca gcgccctgtt ctgcctgagc gtgttcaacc agaagctggt gcccagcggc    1020

```
ttcagccagt gcctggtgaa gaacgtgctg ctggagacca gaggcctgcc cctgaccctg    1080
aaggtgatcg cgccagcgg caaggagaga cccgagaagt actgggacgg cgccgtggac    1140
agactgagca gaggcgagcc cgccgacgag acccacgaga gcagagtgtt cgcccagatc    1200
gaggccaccc tggagaacct ggaccccaag accagagact gcttcctggt gctgggcgcc    1260
ttccccgagg acaagaagat cccccctggac gtgctgatca acgtgctggt ggagctgcac    1320
gacctggagg acgccaccgc cttcgccgtg atcgtggacc tggccaacaa gaacctgatc    1380
accctggtga aggaccccag attcggccac atgttcacca gctactacga catcttcgtg    1440
acccagagag acgtgctgaa ggacgtggcc ctgagactgt gcaaccacgg caagctgaac    1500
aacagagaga gactgatcat gcccaagaga gagagcatgc tgcccagaga gtgggagaag    1560
aaccaggacg accctacaa ggccaaggtg gtgagcatcc acaccggcga gatgtgccag    1620
atggagtggt gggacatgga gctgcccaag gccgaggtgc tgatcgccaa gttcagcacc    1680
gacaagtacg tggtgccccc cttcggcgcc aagatgggca agctgaccgc cctggtgatg    1740
atcaacaacc ccgtgagccc cgcccacctg aaggagttca gcatcttcac caacggcggc    1800
aaggccaaga gcctgtggct gaacagagtg cacgcccccg agctgagcag cagcaccgtg    1860
cccatgcagc agctgcacaa gatcagcctg atcttctgca aggccaacac cagcctggac    1920
aacaccgagc tggaggccgc ccagatcttc ccccacctga ccgacctgac catcgaccac    1980
tgcgacgacc tgctggaggg ccccagcacc atctgcggca tcaccaccct gaacagcatc    2040
agcatcacca cagccccag aatcaaggag ctgcccaagc agctgagcaa gctgaaggcc    2100
ctgcagctgc tgagaggcta cgcctgccac gacctgaaca cgggcccgt ggagatctgc    2160
gagatgccca gactgaagta cgtggacatc agccagtgcg tgagcctgag cagcctgccc    2220
gagaagatcg gcaaggtgag aaccggcgag aagatcgaga ccagagagtg cagcctgagc    2280
agcatcccca cagcgtggt gctgctgacc tgcctgagac acgtgatctg cgacagagag    2340
gccctgtgga tgtgggagaa ggtgcagaag gccgtggccg gcctgagagt ggaggccgcc    2400
gagagaagct tctgcagaga ctggctggag gac                                 2433
```

<210> SEQ ID NO 16
<211> LENGTH: 811
<212> TYPE: PRT
<213> ORGANISM: Artificial Sequence
<220> FEATURE:
<223> OTHER INFORMATION: Amino acid sequence HCP7, variant 5

<400> SEQUENCE: 16

```
Met Ala Asp Ile Ile Gly Gly Glu Val Val Thr Glu Leu Val Arg Gln
1               5                   10                  15

Leu Tyr Ala Val Ser Gln Lys Thr Leu Arg Cys Arg Gly Ile Ala Lys
            20                  25                  30

Asn Leu Ala Thr Met Ile Asp Gly Leu Gln Pro Thr Ile Lys Glu Ile
        35                  40                  45

Gln Tyr Ser Gly Val Glu Leu Thr Pro His Arg Gln Ala Gln Leu Arg
    50                  55                  60

Met Phe Ser Glu Thr Leu Asp Lys Cys Arg Lys Leu Thr Glu Lys Val
65                  70                  75                  80

Leu Lys Ser Ser Arg Trp Asn Met Val Arg Gln Leu Leu His Val Arg
                85                  90                  95

Lys Met Glu Asn Leu Gln Ser Lys Val Ser Ser Phe Leu Asn Gly Gln
            100                 105                 110
```

```
Leu Leu Val His Val Leu Ala Asp Val His His Val Arg Ala Asp Ser
            115                 120                 125

Glu Phe Arg Phe Asp Arg Ile Asp Arg Lys Val Asp Cys Leu Asn Glu
130                 135                 140

Lys Leu Gly Ser Met Lys Leu Arg Gly Ser Glu Thr Leu Arg Glu Ala
145                 150                 155                 160

Gly Lys Thr Ala Asp Ala Cys Val Glu Met Val Thr Thr Asp Gly Ala
                165                 170                 175

Asp Leu Gly Val Gly Leu Asp Leu Gly Lys Arg Lys Val Lys Glu Met
            180                 185                 190

Leu Phe Lys Ser Ile Asp Gly Glu Arg Leu Ile Gly Ile Ser Gly Met
        195                 200                 205

Ser Gly Ser Gly Lys Thr Thr Leu Ala Lys Glu Leu Ala Arg Asp Glu
210                 215                 220

Glu Val Arg Gly His Phe Gly Asn Lys Val Leu Phe Leu Thr Val Ser
225                 230                 235                 240

Gln Ser Pro Asn Leu Glu Glu Leu Arg Ala His Ile Trp Gly Phe Leu
                245                 250                 255

Thr Ser Tyr Glu Ala Gly Val Gly Ala Thr Leu Pro Glu Ser Arg Lys
                260                 265                 270

Leu Val Ile Leu Asp Asp Val Trp Thr Arg Glu Ser Leu Asp Gln Leu
            275                 280                 285

Met Phe Glu Asn Ile Pro Gly Thr Thr Thr Leu Val Val Thr Arg Cys
        290                 295                 300

His Ile Ala Asp Thr Arg Val Thr Tyr Asp Val Asp Leu Leu Asn Glu
305                 310                 315                 320

His Glu Ala Ser Ala Leu Phe Cys Leu Ser Val Phe Asn Gln Lys Leu
                325                 330                 335

Val Pro Ser Gly Phe Ser Gln Cys Leu Val Lys Asn Val Leu Leu Glu
                340                 345                 350

Thr Arg Gly Leu Pro Leu Thr Leu Lys Val Ile Gly Ala Ser Gly Lys
            355                 360                 365

Glu Arg Pro Glu Lys Tyr Trp Asp Gly Ala Val Asp Arg Leu Ser Arg
370                 375                 380

Gly Glu Pro Ala Asp Glu Thr His Glu Ser Arg Val Phe Ala Gln Ile
385                 390                 395                 400

Glu Ala Thr Leu Glu Asn Leu Asp Pro Lys Thr Arg Asp Cys Phe Leu
                405                 410                 415

Val Leu Gly Ala Phe Pro Glu Asp Lys Lys Ile Pro Leu Asp Val Leu
                420                 425                 430

Ile Asn Val Leu Val Glu Leu His Asp Leu Glu Asp Ala Thr Ala Phe
            435                 440                 445

Ala Val Ile Val Asp Leu Ala Asn Lys Asn Leu Ile Thr Leu Val Lys
        450                 455                 460

Asp Pro Arg Phe Gly His Met Phe Thr Ser Tyr Tyr Asp Ile Phe Val
465                 470                 475                 480

Thr Gln Arg Asp Val Leu Lys Asp Val Ala Leu Arg Leu Cys Asn His
                485                 490                 495

Gly Lys Leu Asn Asn Arg Glu Arg Leu Ile Met Pro Lys Arg Glu Ser
                500                 505                 510

Met Leu Pro Arg Glu Trp Glu Lys Asn Gln Asp Asp Pro Tyr Lys Ala
            515                 520                 525

Lys Val Val Ser Ile His Thr Gly Glu Met Cys Gln Met Glu Trp Trp
```

Asp Met Glu Leu Pro Lys Ala Glu Val Leu Ile Ala Lys Phe Ser Thr
545                 550                 555                 560

Asp Lys Tyr Val Val Pro Pro Phe Gly Ala Lys Met Gly Lys Leu Thr
                565                 570                 575

Ala Leu Val Met Ile Asn Asn Ala Val Ser Pro Ala His Leu Lys Glu
            580                 585                 590

Phe Ser Ile Phe Thr Asn Gly Gly Lys Ala Lys Ser Leu Trp Leu Asn
        595                 600                 605

Arg Val His Ala Pro Glu Leu Ser Ser Ser Thr Val Pro Met Gln Gln
    610                 615                 620

Leu His Lys Ile Ser Leu Ile Phe Cys Lys Ala Asn Thr Ser Leu Asp
625                 630                 635                 640

Asn Thr Glu Leu Glu Ala Ala Gln Ile Phe Pro His Leu Thr Asp Leu
                645                 650                 655

Thr Ile Asp His Cys Asp Asp Leu Leu Glu Gly Pro Ser Thr Ile Cys
                660                 665                 670

Gly Ile Thr Thr Leu Asn Ser Ile Ser Ile Thr Asn Ser Pro Arg Ile
            675                 680                 685

Lys Glu Leu Pro Lys Gln Leu Ser Lys Leu Lys Ala Leu Gln Leu Leu
690                 695                 700

Arg Gly Tyr Ala Cys His Asp Leu Asn Ser Gly Pro Val Glu Ile Cys
705                 710                 715                 720

Glu Met Pro Arg Leu Lys Tyr Val Asp Ile Ser Gln Cys Val Ser Leu
                725                 730                 735

Ser Ser Leu Pro Glu Lys Ile Gly Lys Val Arg Thr Gly Glu Lys Ile
            740                 745                 750

Glu Thr Arg Glu Cys Ser Leu Ser Ser Ile Pro Asn Ser Val Val Leu
        755                 760                 765

Leu Thr Cys Leu Arg His Val Ile Cys Asp Arg Glu Ala Leu Trp Met
    770                 775                 780

Trp Glu Lys Val Gln Lys Ala Val Ala Gly Leu Arg Val Glu Ala Ala
785                 790                 795                 800

Glu Arg Ser Phe Cys Arg Asp Trp Leu Glu Asp
                805                 810

```
<210> SEQ ID NO 17
<211> LENGTH: 2433
<212> TYPE: DNA
<213> ORGANISM: Artificial Sequence
<220> FEATURE:
<221> NAME/KEY: source
<222> LOCATION: 1..2433
<223> OTHER INFORMATION: /organism="Artificial Sequence"
      /note="Nucleotide sequence HCP7, variant 6"
      /mol_type="unassigned DNA"

<400> SEQUENCE: 17
atggccgaca tcatcggcgg cgaggtggtg accgagctgg tgagacagct gtacgccgtg      60
agccagaaga ccctgagatg cagaggcatc gccaagaacc tggccaccat gatcgacggc     120
ctgcagccca ccatcaagga gatccagtac agcggcgtgg agctgacccc ccacagacag     180
gcccagctga gaatgttcag cgagaccctg gacaagtgca gaaagctgac cgagaaggtg     240
ctgaagagca gcagatggaa catggtgaga cagctgctgc acgtgagaaa gatggagaac     300
ctgcagagca aggtgagcag cttcctgaac ggccagctgt ggtgcacgt gctggccgac     360
```

```
gtgcaccacg tgagagccga cagcgagttc agattcgaca gaatcgacag aaaggtggac    420
agcctgaacg agaagctggg cagcatgaag ctgagaggca gcgagagcct gagagaggcc    480
ctgaagaccg ccgaggccac cgtggacatg gtgaccaccg acggcgccga cctgggcgtg    540
ggcctggacc tgggcaagag aaaggtgaag gagatgctgt tcaagagcat cgacggcgag    600
agactgatcg gcatcagcgg catgagcggc agcggcaaga ccaccctggc caaggagctg    660
gccagagacg aggaggtgag aggccacttc ggcaacaagg tgctgttcct gaccgtgagc    720
cagagcccca acctggagga gctgagagcc cacatctggg gcttcctgac cagctacgag    780
gccggcgtgg gcgccaccct gcccgagagc agaaagctgg tgatcctgga cgacgtgtgg    840
accagagaga gcctggacca gctgatgttc gagaacatcc ccggcaccac caccctggtg    900
gtgaccagat gcaagctgat cgacagcaga gtgtgctacg acgtggagct gctgaacgag    960
aaggaggcca gcgccctgtt ctgcctgagc gtgttcaacc agaagctggt gcccagcggc   1020
ttcagccaga ccctggtgaa gcaggtggtg ggcgagtgca agggcctgcc cctgagcctg   1080
agagtgatcg gcatctgcct gaaggagaga cccgagaagt actgggaggg cgccgtggag   1140
cacctgagca gaggcgagcc cgccgaggag accagagaga gcagagtgtt cgcccagatc   1200
gaggccaccc tggagaacct ggaccccaag accagagact gcttcctggt gctgggcgcc   1260
ttccccgagg acaagaagat cccccctgga cgtgctgatca acgtgctggt ggagctgcac   1320
gacctggagg acgccaccgc cttcgccgtg atcatcgaca tcgtgaacag aaacctgggc   1380
tgcctggtga aggaccccag attcggccac atgtggacca gctactacga catcttcgtg   1440
acccagcacg acgtggtgca cgacgtggcc ctgagactga gcaaccacgg caagggcaac   1500
aacagagaga gactgctgat gcccaagaga gagagcatgc tgcccagaga gtgggagaga   1560
aacaacgacg agccctacaa ggccagagtg gtgagcatcc acaccggcga gatgacccag   1620
atggacttct tcgagatgga gctgcccaga atggagatcc tgatcctgca cttcagcagc   1680
gagaagtacg tgctgccccc cttcatcgcc aagatgggca aggtgagcgc cctggtgatc   1740
atcaacaacg gcatgtgccc cgccagactg cacgacttca gcatcttcac caacatcgcc   1800
aagctgaaga gcctgtggct gcagagagtg cacgtgcccg agctgacctg ctgcaccatg   1860
ccccctgcaga acctgcacaa gctgtgcctg atcttctgca agatccagac cagcgccgac   1920
aacaccgagc tggacatcgc ccagatcttc cccaaggcca cgacctgac cgccgagcac   1980
tgcgaggacc tgctggacct gcccagcacc atcaccggca tcaccagcct gaacagcatc   2040
agcgccacca actgccccag aatcaaggag ctgcccaaga acctgagcaa gctgaaggcc   2100
ctgcagctgc tgagactgta cgcctgccac gagctgaaca gcctgcccgt ggagatctgc   2160
gagggcccca gactgaagtt cgtggacatc agccagtgcg tgagcctgag cagcctgccc   2220
gagaagatcg gcaaggtgaa gaccctggac aagatcgaca ccagagagtg cagcctgagc   2280
agcatcccca caccgtggt gctgctgagc agcctgagac acgtgatctg cgagcacgac   2340
gccctgtgga tgtgggacag agtgcagaag ggcatggtgg gcctgagagt ggaggtggcc   2400
gagcacagct tcagcagaga cttcctggac gac                               2433
```

<210> SEQ ID NO 18
<211> LENGTH: 811
<212> TYPE: PRT
<213> ORGANISM: Artificial Sequence
<220> FEATURE:
<223> OTHER INFORMATION: Amino acid sequence HCP7, variant 6

<400> SEQUENCE: 18

```
Met Ala Asp Ile Ile Gly Gly Glu Val Val Thr Glu Leu Val Arg Gln
1               5                   10                  15

Leu Tyr Ala Val Ser Gln Lys Thr Leu Arg Cys Arg Gly Ile Ala Lys
                20                  25                  30

Asn Leu Ala Thr Met Ile Asp Gly Leu Gln Pro Thr Ile Lys Glu Ile
            35                  40                  45

Gln Tyr Ser Gly Val Glu Leu Thr Pro His Arg Gln Ala Gln Leu Arg
    50                  55                  60

Met Phe Ser Glu Thr Leu Asp Lys Cys Arg Lys Leu Thr Glu Lys Val
65                  70                  75                  80

Leu Lys Ser Ser Arg Trp Asn Met Val Arg Gln Leu Leu His Val Arg
                85                  90                  95

Lys Met Glu Asn Leu Gln Ser Lys Val Ser Ser Phe Leu Asn Gly Gln
            100                 105                 110

Leu Leu Val His Val Leu Ala Asp Val His His Val Arg Ala Asp Ser
            115                 120                 125

Glu Phe Arg Phe Asp Arg Ile Asp Arg Lys Val Asp Ser Leu Asn Glu
    130                 135                 140

Lys Leu Gly Ser Met Lys Leu Arg Gly Ser Glu Ser Leu Arg Glu Ala
145                 150                 155                 160

Leu Lys Thr Ala Glu Ala Thr Val Asp Met Val Thr Thr Asp Gly Ala
                165                 170                 175

Asp Leu Gly Val Gly Leu Asp Leu Gly Lys Arg Lys Val Lys Glu Met
            180                 185                 190

Leu Phe Lys Ser Ile Asp Gly Glu Arg Leu Ile Gly Ile Ser Gly Met
            195                 200                 205

Ser Gly Ser Gly Lys Thr Thr Leu Ala Lys Glu Leu Ala Arg Asp Glu
210                 215                 220

Glu Val Arg Gly His Phe Gly Asn Lys Val Leu Phe Leu Thr Val Ser
225                 230                 235                 240

Gln Ser Pro Asn Leu Glu Glu Leu Arg Ala His Ile Trp Gly Phe Leu
            245                 250                 255

Thr Ser Tyr Glu Ala Gly Val Gly Ala Thr Leu Pro Glu Ser Arg Lys
            260                 265                 270

Leu Val Ile Leu Asp Asp Val Trp Thr Arg Glu Ser Leu Asp Gln Leu
            275                 280                 285

Met Phe Glu Asn Ile Pro Gly Thr Thr Thr Leu Val Val Thr Arg Cys
290                 295                 300

Lys Leu Ile Asp Ser Arg Val Cys Tyr Asp Val Glu Leu Leu Asn Glu
305                 310                 315                 320

Lys Glu Ala Ser Ala Leu Phe Cys Leu Ser Val Phe Asn Gln Lys Leu
            325                 330                 335

Val Pro Ser Gly Phe Ser Gln Thr Leu Val Lys Gln Val Val Gly Glu
            340                 345                 350

Cys Lys Gly Leu Pro Leu Ser Leu Arg Val Ile Gly Ile Cys Leu Lys
            355                 360                 365

Glu Arg Pro Glu Lys Tyr Trp Glu Gly Ala Val Glu His Leu Ser Arg
    370                 375                 380

Gly Glu Pro Ala Glu Glu Thr Arg Glu Ser Arg Val Phe Ala Gln Ile
385                 390                 395                 400

Glu Ala Thr Leu Glu Asn Leu Asp Pro Lys Thr Arg Asp Cys Phe Leu
                405                 410                 415
```

Val Leu Gly Ala Phe Pro Glu Asp Lys Lys Ile Pro Leu Asp Val Leu
            420                 425                 430

Ile Asn Val Leu Val Glu Leu His Asp Leu Glu Asp Ala Thr Ala Phe
            435                 440                 445

Ala Val Ile Ile Asp Ile Val Asn Arg Asn Leu Gly Cys Leu Val Lys
            450                 455                 460

Asp Pro Arg Phe Gly His Met Trp Thr Ser Tyr Tyr Asp Ile Phe Val
465                 470                 475                 480

Thr Gln His Asp Val His Asp Val Ala Leu Arg Leu Ser Asn His
                485                 490                 495

Gly Lys Gly Asn Asn Arg Glu Arg Leu Leu Met Pro Lys Arg Glu Ser
            500                 505                 510

Met Leu Pro Arg Glu Trp Glu Arg Asn Asn Asp Glu Pro Tyr Lys Ala
            515                 520                 525

Arg Val Val Ser Ile His Thr Gly Glu Met Thr Gln Met Asp Phe Phe
530                 535                 540

Glu Met Glu Leu Pro Arg Met Glu Ile Leu Ile Leu His Phe Ser Ser
545                 550                 555                 560

Glu Lys Tyr Val Leu Pro Pro Phe Ile Ala Lys Met Gly Lys Val Ser
            565                 570                 575

Ala Leu Val Ile Ile Asn Asn Gly Met Cys Pro Ala Arg Leu His Asp
            580                 585                 590

Phe Ser Ile Phe Thr Asn Ile Ala Lys Leu Lys Ser Leu Trp Leu Gln
            595                 600                 605

Arg Val His Val Pro Glu Leu Thr Cys Cys Thr Met Pro Leu Gln Asn
610                 615                 620

Leu His Lys Leu Cys Leu Ile Phe Cys Lys Ile Gln Thr Ser Ala Asp
625                 630                 635                 640

Asn Thr Glu Leu Asp Ile Ala Gln Ile Phe Pro Lys Ala Ser Asp Leu
            645                 650                 655

Thr Ala Glu His Cys Glu Asp Leu Leu Asp Leu Pro Ser Thr Ile Thr
            660                 665                 670

Gly Ile Thr Ser Leu Asn Ser Ile Ser Ala Thr Asn Cys Pro Arg Ile
            675                 680                 685

Lys Glu Leu Pro Lys Asn Leu Ser Lys Leu Lys Ala Leu Gln Leu Leu
            690                 695                 700

Arg Leu Tyr Ala Cys His Glu Leu Asn Ser Leu Pro Val Glu Ile Cys
705                 710                 715                 720

Glu Gly Pro Arg Leu Lys Phe Val Asp Ile Ser Gln Cys Val Ser Leu
            725                 730                 735

Ser Ser Leu Pro Glu Lys Ile Gly Lys Val Lys Thr Leu Asp Lys Ile
            740                 745                 750

Asp Thr Arg Glu Cys Ser Leu Ser Ser Ile Pro Asn Thr Val Val Leu
            755                 760                 765

Leu Ser Ser Leu Arg His Val Ile Cys Glu His Asp Ala Leu Trp Met
            770                 775                 780

Trp Asp Arg Val Gln Lys Gly Met Val Gly Leu Arg Val Glu Val Ala
785                 790                 795                 800

Glu His Ser Phe Ser Arg Asp Phe Leu Asp Asp
            805                 810

<210> SEQ ID NO 19
<211> LENGTH: 2433
<212> TYPE: DNA

<213> ORGANISM: Artificial Sequence
<220> FEATURE:
<221> NAME/KEY: source
<222> LOCATION: 1..2433
<223> OTHER INFORMATION: /organism="Artificial Sequence"
　　　　/note="Nucleotide sequence HCP7, variant 7"
　　　　/mol_type="unassigned DNA"

<400> SEQUENCE: 19

```
atggccgaca tcatcggcgg cgaggtggtg accgagctgg tgagacagct gtacgccgtg      60
agccagaaga ccctgagatg cagaggcatc gccaagaacc tggccaccat gatcgacggc     120
ctgcagccca ccatcaagga gatccagtac agcggcgtgg agctgacccc ccacagacag     180
gcccagctga gaatgttcag cgagaccctg acaagtgcag aaagctgac cgagaaggtg      240 ctgaagagca gcagatggaa catggtgaga cagctgctgc acgtgagaaa gatggagaac     300
ctgcagagca aggtgagcag cttcctgaac ggccagctgc tggtgcacgt gctggccgac     360
gtgcaccacg tgagagccga cagcgagttc agattcgaca gaatcgacag aaaggtggac     420
agcctgaacg agaagctggg cagcatgaga ctgagaggca gcgagagcct gagagaggcc     480
ctgaagaccg ccgaggccac cgtggagatg gtgaccaccg acggcgccga cctgggcgtg     540
ggcctggacc tgggcaagag aaaggtgaag gagatgctgt caagagcat cgacggcgag      600 agactgatcg gcatcagcgg catgagcggc agcggcaaga ccaccctggc caaggagctg     660
gccagagacg aggaggtgag aggccacttc ggcaacaagg tgctgttcct gaccgtgagc     720
cagagcccca acctggagga gctgagagcc cacatctggg gcttcctgac cagctacgag     780
gccggcgtgg gcgccaccct gcccgagagc agaaagctgg tgatcctgga cgacgtgtgg     840
accagagaga gcctggacca gctgatgttc gagaacatcc ccggcaccac caccctggtg     900
gtgagcagaa gcaagctggc cgacagcaga gtgtgctacg acgtggaggt gctgaacgag     960
cacgaggcca ccgtgctgtt cagcctgagc gtgttcaaca caagctggt gcccagcggc    1020 ttcagccaga gcctggtgaa gcaggtggtg ggcgagtgca agggcatccc cctgagcctg    1080
aaggtgatcg gcatgagcct gaaggagaga cccgagaagt acttcgagct ggccgtggag    1140
agactgagca gaggcgagcc cgccgacgag agccacgaga gcagtgtt cgcccagatc      1200 gaggccaccc tggagaacct ggaccccaag accagagact gcttcctggt gctgggcgcc    1260
ttccccgagg acaagaagat ccccctggac gtgctgatca cgtgctggt ggagctgcac     1320 gacctggagg acgccaccgc cttcgccgtg atcgtggacc tggccaacag aaacctgctg    1380
accctggtga aggaccccag attcggccac atgtacacca gctactcga catcttcgtg     1440 acccagcacg acgtgggcaa ggacgtgctg ctgagactga gcaaccacat caaggtgaac    1500
cagaaggaca gactgctgat gcccaagaga gagagcatgc tgcccagaga gtgggacaga    1560
aacaacgacg agccctacaa ggccagagtg gtgagcatcc acaccggcga gatgacccag    1620
atggactggt cgacctgga gctgcccaag gccgaggtgc tgatcctgca cttctgcagc     1680
gacaagtacg tgctgccccc cttcatcgcc aagatgggga gctgaccgc cctggtgatc     1740 atcaacaacg gcatgagccc cgccagactg cacgacttca gcggctggac caacctggcc    1800
aagctgaaga ccctgtggct gcagagagtg cacgtgcccg agctgagcag cagcaccgtg    1860
cccgtgcaga acctgaagaa gctgagcctg atcttctgca agatcaacac cagcctggac    1920
cagaccgagc tggacatcat ccagatcttc cccaagctga gcgacctgac catcgaccac    1980
tgcgacgacc tgctggagct gcccagcacc atctgcggcg ccaccagcct gcagagcatc    2040
agcatcacca actgccccag aatcaaggac ctgcccaaga acctgagcaa gctgaaggcc    2100
```

-continued

```
ctgcaggccc tgagactgta cgcctgccac gagctgaaca gcctgcccgt ggaggtgtgc    2160
gacctgccca gactgaagta catggacatc agccagtgcc tgagcctgag cagcctgccc    2220
gagaaggtgg gccacgtgaa gaccctggag aagatcgaca ccagagagtg cagcgccagc    2280
agcatccccc agagcgtggt gctgctgacc agcgccagac acgtgatctg cgacagagag    2340
gccatctgga tgtgggagaa ggtgcagaag gccgtggccg gcctgagagt ggaggccgcc    2400
gagaagagct tcagcagaga ctggctggac gac                                 2433
```

<210> SEQ ID NO 20
<211> LENGTH: 811
<212> TYPE: PRT
<213> ORGANISM: Artificial Sequence
<220> FEATURE:
<223> OTHER INFORMATION: Amino acid sequence HCP7, variant 7

<400> SEQUENCE: 20

```
Met Ala Asp Ile Ile Gly Gly Glu Val Val Thr Glu Leu Val Arg Gln
1               5                   10                  15

Leu Tyr Ala Val Ser Gln Lys Thr Leu Arg Cys Arg Gly Ile Ala Lys
            20                  25                  30

Asn Leu Ala Thr Met Ile Asp Gly Leu Gln Pro Thr Ile Lys Glu Ile
        35                  40                  45

Gln Tyr Ser Gly Val Glu Leu Thr Pro His Arg Gln Ala Gln Leu Arg
    50                  55                  60

Met Phe Ser Glu Thr Leu Asp Lys Cys Arg Lys Leu Thr Glu Lys Val
65                  70                  75                  80

Leu Lys Ser Ser Arg Trp Asn Met Val Arg Gln Leu Leu His Val Arg
                85                  90                  95

Lys Met Glu Asn Leu Gln Ser Lys Val Ser Ser Phe Leu Asn Gly Gln
            100                 105                 110

Leu Leu Val His Val Leu Ala Asp Val His His Val Arg Ala Asp Ser
        115                 120                 125

Glu Phe Arg Phe Asp Arg Ile Asp Arg Lys Val Asp Ser Leu Asn Glu
    130                 135                 140

Lys Leu Gly Ser Met Arg Leu Arg Gly Ser Glu Ser Leu Arg Glu Ala
145                 150                 155                 160

Leu Lys Thr Ala Glu Ala Thr Val Glu Met Val Thr Thr Asp Gly Ala
                165                 170                 175

Asp Leu Gly Val Gly Leu Asp Leu Gly Lys Arg Lys Val Lys Glu Met
            180                 185                 190

Leu Phe Lys Ser Ile Asp Gly Glu Arg Leu Ile Gly Ile Ser Gly Met
        195                 200                 205

Ser Gly Ser Gly Lys Thr Thr Leu Ala Lys Glu Leu Ala Arg Asp Glu
    210                 215                 220

Glu Val Arg Gly His Phe Gly Asn Lys Val Leu Phe Leu Thr Val Ser
225                 230                 235                 240

Gln Ser Pro Asn Leu Glu Glu Leu Arg Ala His Ile Trp Gly Phe Leu
                245                 250                 255

Thr Ser Tyr Glu Ala Gly Val Gly Ala Thr Leu Pro Glu Ser Arg Lys
            260                 265                 270

Leu Val Ile Leu Asp Asp Val Trp Thr Arg Glu Ser Leu Asp Gln Leu
        275                 280                 285

Met Phe Glu Asn Ile Pro Gly Thr Thr Leu Val Val Ser Arg Ser
    290                 295                 300
```

-continued

```
Lys Leu Ala Asp Ser Arg Val Cys Tyr Asp Val Glu Val Leu Asn Glu
305                 310                 315                 320

His Glu Ala Thr Val Leu Phe Ser Leu Ser Val Phe Asn Asn Lys Leu
            325                 330                 335

Val Pro Ser Gly Phe Ser Gln Ser Leu Val Lys Gln Val Gly Glu
        340                 345                 350

Cys Lys Gly Ile Pro Leu Ser Leu Lys Val Ile Gly Met Ser Leu Lys
            355                 360                 365

Glu Arg Pro Glu Lys Tyr Phe Glu Leu Ala Val Glu Arg Leu Ser Arg
            370                 375                 380

Gly Glu Pro Ala Asp Glu Ser His Glu Ser Arg Val Phe Ala Gln Ile
385                 390                 395                 400

Glu Ala Thr Leu Glu Asn Leu Asp Pro Lys Thr Arg Asp Cys Phe Leu
                405                 410                 415

Val Leu Gly Ala Phe Pro Glu Asp Lys Lys Ile Pro Leu Asp Val Leu
            420                 425                 430

Ile Asn Val Leu Val Glu Leu His Asp Leu Glu Asp Ala Thr Ala Phe
            435                 440                 445

Ala Val Ile Val Asp Leu Ala Asn Arg Asn Leu Leu Thr Leu Val Lys
        450                 455                 460

Asp Pro Arg Phe Gly His Met Tyr Thr Ser Tyr Tyr Asp Ile Phe Val
465                 470                 475                 480

Thr Gln His Asp Val Gly Lys Asp Val Leu Leu Arg Leu Ser Asn His
                485                 490                 495

Ile Lys Val Asn Gln Lys Asp Arg Leu Leu Met Pro Lys Arg Glu Ser
            500                 505                 510

Met Leu Pro Arg Glu Trp Asp Arg Asn Asn Asp Glu Pro Tyr Lys Ala
            515                 520                 525

Arg Val Val Ser Ile His Thr Gly Glu Met Thr Gln Met Asp Trp Phe
    530                 535                 540

Asp Leu Glu Leu Pro Lys Ala Glu Val Leu Ile Leu His Phe Cys Ser
545                 550                 555                 560

Asp Lys Tyr Val Leu Pro Pro Phe Ile Ala Lys Met Gly Lys Leu Thr
                565                 570                 575

Ala Leu Val Ile Ile Asn Asn Gly Met Ser Pro Ala Arg Leu His Asp
            580                 585                 590

Phe Ser Gly Trp Thr Asn Leu Ala Lys Leu Lys Thr Leu Trp Leu Gln
        595                 600                 605

Arg Val His Val Pro Glu Leu Ser Ser Ser Thr Val Pro Val Gln Asn
    610                 615                 620

Leu Lys Lys Leu Ser Leu Ile Phe Cys Lys Ile Asn Thr Ser Leu Asp
625                 630                 635                 640

Gln Thr Glu Leu Asp Ile Ile Gln Ile Phe Pro Lys Leu Ser Asp Leu
                645                 650                 655

Thr Ile Asp His Cys Asp Asp Leu Leu Glu Leu Pro Ser Thr Ile Cys
            660                 665                 670

Gly Ala Thr Ser Leu Gln Ser Ile Ser Ile Thr Asn Cys Pro Arg Ile
            675                 680                 685

Lys Asp Leu Pro Lys Asn Leu Ser Lys Leu Lys Ala Leu Gln Ala Leu
            690                 695                 700

Arg Leu Tyr Ala Cys His Glu Leu Asn Ser Leu Pro Val Glu Val Cys
705                 710                 715                 720
```

```
Asp Leu Pro Arg Leu Lys Tyr Met Asp Ile Ser Gln Cys Leu Ser Leu
                725                 730                 735

Ser Ser Leu Pro Glu Lys Val Gly His Val Lys Thr Leu Glu Lys Ile
            740                 745                 750

Asp Thr Arg Glu Cys Ser Ala Ser Ser Ile Pro Gln Ser Val Val Leu
        755                 760                 765

Leu Thr Ser Ala Arg His Val Ile Cys Asp Arg Glu Ala Ile Trp Met
    770                 775                 780

Trp Glu Lys Val Gln Lys Ala Val Ala Gly Leu Arg Val Glu Ala Ala
785                 790                 795                 800

Glu Lys Ser Phe Ser Arg Asp Trp Leu Asp Asp
                805                 810

<210> SEQ ID NO 21
<211> LENGTH: 2433
<212> TYPE: DNA
<213> ORGANISM: Artificial Sequence
<220> FEATURE:
<221> NAME/KEY: source
<222> LOCATION: 1..2433
<223> OTHER INFORMATION: /organism="Artificial Sequence"
      /note="Nucleotide sequence HCP7, variant 8"
      /mol_type="unassigned DNA"

<400> SEQUENCE: 21
atggccgaca tcatcggcgg cgaggtggtg accgagctgg tgagacagct gtacgccgtg      60
agccagaaga ccctgagatg cagaggcatc gccaagaacc tggccaccat gatcgacggc     120
ctgcagccca ccatcaagga gatccagtac agcggcgtgg agctgacccc ccacagacag     180
gcccagctga gaatgttcag cgagaccctg acaagtgca gaaagctgac cgagaaggtg      240
ctgaagagca gcagatggaa catggtgaga cagctgctgc acgtgagaaa gatggagaac     300
ctgcagagca aggtgagcag cttcctgaac ggccagctgc tggtgcacgt gctggccgac     360
gtgcaccacg tgagagccga cagcgagttc agattcgaca gaatcgacag aaaggtggac     420
agcctgaacg agaagctggg cagcatgaag ctgagaggca gcgagagcct gagagaggcc     480
ctgaagaccg ccgaggccac cgtggagatg gtgaccaccg acggcgccga cctgggcgtg     540
ggcctggacc tgggcaagag aaaggtgaag gagatgctgt caagagcat cgacggcgag      600 agactgatcg gcatcagcgg catgagcggc agcggcaaga ccaccctggc caaggagctg     660
gccagagacg aggaggtgag aggccacttc ggcaacaagg tgctgttcct gaccgtgagc     720
cagagcccca acctggagga gctgagagcc cacatctggg gcttcctgac cagctacgag     780
gccggcgtgg gcgccaccct gcccgagagc agaaagctgg tgatcctgga cgacgtgtgg     840
accagagaga gcctggacca gctgatgttc gagaacatcc ccggcaccac caccctggtg     900
gtgagcagaa gcaagctggt ggacagcaga gtgacctacg acgtggagat gctgaacgag     960
cacgagggca ccgccctgtt ctgcctgagc gtgttcaacc agaagctggt gcccagcggc    1020
ttcagccaga gcctggtgaa gcaggtggtg ggcgagtgca agggcctgcc cctgagcctg    1080
aaggtgatcg gcgccagcct gaaggagaga cccgagaagt actgggaggg cgccgtggag    1140
agactgagca gaggcgagcc cgccgacgag acccacgaga gcagaggctt cgcccagatc    1200
gaggccaccc tggagaacct ggaccccaag accagagact gcttcctggt gctgggcgcc    1260
ttccccgagg acaagaagat ccccctggac gtgctgatca acgtgctggt ggagctgcac    1320
gacctggagg acgccaccgc cttcgccgtg atcgtggacc tggccaacag aaacctgctg    1380
accctggtga aggaccccag attcggccac atgtacacca gctactggga catcttcgtg    1440
```

```
acccagcacg acgtgctgag agacgtgggc ctgagactga gcaaccacgg caaggtgaac   1500
aacagagaga gactgctgat gcccaagaga gagagcatgc tgcccagaga gtgggacaga   1560
aaccaggacg agccctggaa ggccagagtg gtgagcatcc acaccggcga gatgacccag   1620
atggactggt tcgacatcga gctgcccaag gccgaggtgc tggtgctgca cttcagcagc   1680
gacaagtacg tgctgccccc cttcatcgcc aagatgggca agctgaccgc cctggtgatc   1740
atgaacaacg gcatgagccc cgccagactg cacgacttca gcatcttcac caacctggcc   1800
aagctgaaga gcctgtggct gcagagagtg cacgtgcccg agctgagcag cagcaccgtg   1860
cccctgcaga acctgcacaa gctgagcctg atcttctgcc acatcaacac ctgcctggac   1920
cagaccgagc tggacatcgc ccagatcttc cccaagctga gcgacctgac catcgaccac   1980
tgcgacgacc tgctggagct gccctgcacc atctgcggca tcaccagcct gaacagcatc   2040
agcatcacca acagccccag aatcaaggag ctgcccaaga acctgtgcaa gctgaaggcc   2100
ctgcagctgc tgagactgta cgcctgccac gagctgaaca gcctgcccgt ggagatctgc   2160
gagctgccca gactgaagta cgtggagatc agccagtgcg tgagcctgag cagcctgccc   2220
gagaagatcg gcaaggtgaa gaccatcgag aagatcgaca ccagagagtg cagcctgagc   2280
agcatcccca cagcgtggt gctgctgacc agcctgagac acgtgatcac cgagagagag   2340
gccctgtgga tgtgggagaa ggtgcagaag gccgtggccg gcctgagagt ggaggccgcc   2400
gagaagagct tcagcagaga ctgggtggac gac                                2433
```

<210> SEQ ID NO 22
<211> LENGTH: 811
<212> TYPE: PRT
<213> ORGANISM: Artificial Sequence
<220> FEATURE:
<223> OTHER INFORMATION: Amino acid sequence HCP7, variant 8

<400> SEQUENCE: 22

```
Met Ala Asp Ile Ile Gly Gly Glu Val Val Thr Glu Leu Val Arg Gln
  1               5                  10                  15

Leu Tyr Ala Val Ser Gln Lys Thr Leu Arg Cys Arg Gly Ile Ala Lys
             20                  25                  30

Asn Leu Ala Thr Met Ile Asp Gly Leu Gln Pro Thr Ile Lys Glu Ile
         35                  40                  45

Gln Tyr Ser Gly Val Glu Leu Thr Pro His Arg Gln Ala Gln Leu Arg
     50                  55                  60

Met Phe Ser Glu Thr Leu Asp Lys Cys Arg Lys Leu Thr Glu Lys Val
 65                  70                  75                  80

Leu Lys Ser Ser Arg Trp Asn Met Val Arg Gln Leu Leu His Val Arg
                 85                  90                  95

Lys Met Glu Asn Leu Gln Ser Lys Val Ser Ser Phe Leu Asn Gly Gln
            100                 105                 110

Leu Leu Val His Val Leu Ala Asp Val His His Val Arg Ala Asp Ser
        115                 120                 125

Glu Phe Arg Phe Asp Arg Ile Asp Arg Lys Val Asp Ser Leu Asn Glu
    130                 135                 140

Lys Leu Gly Ser Met Lys Leu Arg Gly Ser Glu Ser Leu Arg Glu Ala
145                 150                 155                 160

Leu Lys Thr Ala Glu Ala Thr Val Glu Met Val Thr Thr Asp Gly Ala
                165                 170                 175

Asp Leu Gly Val Gly Leu Asp Leu Gly Lys Arg Lys Val Lys Glu Met
```

```
                180                 185                 190
Leu Phe Lys Ser Ile Asp Gly Glu Arg Leu Ile Gly Ile Ser Gly Met
            195                 200                 205
Ser Gly Ser Gly Lys Thr Thr Leu Ala Lys Glu Leu Ala Arg Asp Glu
            210                 215                 220
Glu Val Arg Gly His Phe Gly Asn Lys Val Leu Phe Leu Thr Val Ser
225                 230                 235                 240
Gln Ser Pro Asn Leu Glu Glu Leu Arg Ala His Ile Trp Gly Phe Leu
            245                 250                 255
Thr Ser Tyr Glu Ala Gly Val Gly Ala Thr Leu Pro Glu Ser Arg Lys
            260                 265                 270
Leu Val Ile Leu Asp Asp Val Trp Thr Arg Glu Ser Leu Asp Gln Leu
            275                 280                 285
Met Phe Glu Asn Ile Pro Gly Thr Thr Thr Leu Val Val Ser Arg Ser
            290                 295                 300
Lys Leu Val Asp Ser Arg Val Thr Tyr Asp Val Glu Met Leu Asn Glu
305                 310                 315                 320
His Glu Gly Thr Ala Leu Phe Cys Leu Ser Val Phe Asn Gln Lys Leu
            325                 330                 335
Val Pro Ser Gly Phe Ser Gln Ser Leu Val Lys Gln Val Val Gly Glu
            340                 345                 350
Cys Lys Gly Leu Pro Leu Ser Leu Lys Val Ile Gly Ala Ser Leu Lys
            355                 360                 365
Glu Arg Pro Glu Lys Tyr Trp Glu Gly Ala Val Glu Arg Leu Ser Arg
            370                 375                 380
Gly Glu Pro Ala Asp Glu Thr His Glu Ser Arg Gly Phe Ala Gln Ile
385                 390                 395                 400
Glu Ala Thr Leu Glu Asn Leu Asp Pro Lys Thr Arg Asp Cys Phe Leu
            405                 410                 415
Val Leu Gly Ala Phe Pro Glu Asp Lys Lys Ile Pro Leu Asp Val Leu
            420                 425                 430
Ile Asn Val Leu Val Glu Leu His Asp Leu Glu Asp Ala Thr Ala Phe
            435                 440                 445
Ala Val Ile Val Asp Leu Ala Asn Arg Asn Leu Leu Thr Leu Val Lys
            450                 455                 460
Asp Pro Arg Phe Gly His Met Tyr Thr Ser Tyr Trp Asp Ile Phe Val
465                 470                 475                 480
Thr Gln His Asp Val Leu Arg Asp Val Gly Leu Arg Leu Ser Asn His
            485                 490                 495
Gly Lys Val Asn Asn Arg Glu Arg Leu Leu Met Pro Lys Arg Glu Ser
            500                 505                 510
Met Leu Pro Arg Glu Trp Asp Arg Asn Gln Asp Glu Pro Trp Lys Ala
            515                 520                 525
Arg Val Val Ser Ile His Thr Gly Glu Met Thr Gln Met Asp Trp Phe
            530                 535                 540
Asp Ile Glu Leu Pro Lys Ala Glu Val Leu Val Leu His Phe Ser Ser
545                 550                 555                 560
Asp Lys Tyr Val Leu Pro Pro Phe Ile Ala Lys Met Gly Lys Leu Thr
            565                 570                 575
Ala Leu Val Ile Met Asn Asn Gly Met Ser Pro Ala Arg Leu His Asp
            580                 585                 590
Phe Ser Ile Phe Thr Asn Leu Ala Lys Leu Lys Ser Leu Trp Leu Gln
            595                 600                 605
```

```
Arg Val His Val Pro Glu Leu Ser Ser Ser Thr Val Pro Leu Gln Asn
    610                 615                 620
Leu His Lys Leu Ser Leu Ile Phe Cys His Ile Asn Thr Cys Leu Asp
625                 630                 635                 640
Gln Thr Glu Leu Asp Ile Ala Gln Ile Phe Pro Lys Leu Ser Asp Leu
                645                 650                 655
Thr Ile Asp His Cys Asp Asp Leu Leu Glu Leu Pro Cys Thr Ile Cys
                660                 665                 670
Gly Ile Thr Ser Leu Asn Ser Ile Ser Ile Thr Asn Ser Pro Arg Ile
                675                 680                 685
Lys Glu Leu Pro Lys Asn Leu Cys Lys Leu Lys Ala Leu Gln Leu Leu
    690                 695                 700
Arg Leu Tyr Ala Cys His Glu Leu Asn Ser Leu Pro Val Glu Ile Cys
705                 710                 715                 720
Glu Leu Pro Arg Leu Lys Tyr Val Gly Ile Ser Gln Cys Val Ser Leu
                725                 730                 735
Ser Ser Leu Pro Glu Lys Ile Gly Lys Val Lys Thr Ile Glu Lys Ile
                740                 745                 750
Asp Thr Arg Glu Cys Ser Leu Ser Ser Ile Pro Asn Ser Val Val Leu
                755                 760                 765
Leu Thr Ser Leu Arg His Val Ile Thr Glu Arg Glu Ala Leu Trp Met
770                 775                 780
Trp Glu Lys Val Gln Lys Ala Val Ala Gly Leu Arg Val Glu Ala Ala
785                 790                 795                 800
Glu Lys Ser Phe Ser Arg Asp Trp Val Asp Asp
                805                 810

<210> SEQ ID NO 23
<211> LENGTH: 2436
<212> TYPE: DNA
<213> ORGANISM: Artificial Sequence
<220> FEATURE:
<221> NAME/KEY: source
<222> LOCATION: 1..2436
<223> OTHER INFORMATION: /organism="Artificial Sequence"
      /note="Nucleotide sequence HCP7, variant 9"
      /mol_type="unassigned DNA"

<400> SEQUENCE: 23
atggcggaca ttataggggg agaagtggtc accgaactcg tccgtcaact ttatgctgta      60
tcccagaaaa cactacgttg caggggtatt gcgaaaaatt tggccactat gatagatggg     120
ctccaaccga caataaagga gatacagtat tccggtgttg agttaactcc tcatcgtcag     180
gctcagctac gaatgttctc agaaacactg gacaaatgtc gcaaactaac agaaaaggtc     240
ttgaaatcct cgcgctggaa catggtcaga caaatgctgc atgtgcgaaa atggagaat      300
ctccaatcga aggtctcttc atttctaaat ggtcaactgt tggtgcatgt cctggccgat     360
gtccatcatg tgcgggcgga ttctgaattc agatttgacc gtatagatcg gaaagtcgac     420
agcctaaacg aaaaattagg gtcgatgaag ctacgtggct ccgaatcgct gcgagaagcc     480
ctcaaaacag cggaagcaac cgtggaaatg gtaaccaccg atggagccga cttaggcgta     540
ggcctcgact ggggaaaaag gaaagtcaag gagatgttgt tcaaaagcat tgatggagaa     600
agactgattg gcatctcagg tatgagtgga agcggaaaaa cgacccttgc caaagagcta     660
gcacgcgatg aggaagtccg aggtcatttt gggaataaag ttatgttttct aacagtgagt     720
caatctccaa atcttgaaga gctgcgtgcc cacatatggg ggtttctgac gtcgtacgaa     780
```

```
gccggcgtcg gagccaccct ccccgaatcc cggaaactcg tgatcctgga tgatgtatgg    840
acccgggaat cccttgacca aatgatgttt gagaacatac caggaaccac aactttagtc    900
gtgtctagat ccaaattggc agacagccgt gttacgtatg atgtcgagct actcaatgag    960
catgaagcaa ctgcgatgtt ttgtttatcc gttttcaacc aaaagttagt accctctgga   1020
ttctcacaga gcatggtgaa acaagtagtc ggagaatgca aggggttgcc cttgtctctg   1080
aaagttattg gggcctccct gaaggaacgt ccggaaaaat actgggaagg ggccgtcgaa   1140
cggctgtcta ggggagagcc tgcggatgaa acccatgaat cgcgtgtctt tgcacagata   1200
gaagcgacgt tagaaaatct ggacccgaaa acacgcgact gttttttagt cttaggtgcg   1260
tttcccgaag acaaaaagat tcctctcgat gtcatgataa atgtcctagt agaactccat   1320
gacctggaag atgcgacagc ttttgccgtc atcgttgatc tggcgaatcg gaatctgttg   1380
actctggtta aagatccccg gtttggacat atgtatacct cgtattatga catttttgtc   1440
acccaacatg atgtcatgag agatgtggcg ttacgcttat ccaatcatgg aaaagtcaat   1500
aatcgagaga ggctcatgat gccgaaacgc gagtccatgc tcccgcgaga tgggaaagg    1560 aataatgacg agccatacaa agcgcgagta gtgtccatcc atacgggtga atgactcaa    1620 atggattggt ttgacatgga gctaccgaaa gcggaagtta tgattctaca tttctcaagt   1680
gacaaatatg tcttgccccc attcatcgcg aaaatgggga aactcacagc gttggttatt   1740
ataaataatg gtatgtcgcc tgcgcgatta catgatttct ccattttac gaatttggcc   1800 aaactcaaat ctttatggct ccaacgagtg catgttcctg aactgtcaag ctctacggtc   1860
cctttacaaa atctccataa actcagtatg atttttttgca aaataaatac ctcgctggac   1920
caaacggaaa tggacattgc ccaaatcttc ccgaaattat cagatctcac catagaccat   1980
tgtgatgatt taatggaaat gccatctact atatgtggca ttaccagtct aaatagcatc   2040
agtataacca attgtccgag aattaaggaa ctacccaaaa atctctcgaa actaaaagct   2100
ctccaattac tgagattata tgcgtgccat gaattaaatt cattaccagt cgaaatatgt   2160
gaaatgccgc ggttgaaata tgttgatatc tcccaatgtg tatctctttc atcactacct   2220
gaaaaaatcg ggaaagtcaa aactctcgaa aaaatcgata ctagagaatg tagcctctcg   2280
tccataccga atagcgtcgt tctgttaacg agcctacgcc acgtgatatg tgaccgtgag   2340
gccttgtgga tgtgggaaaa agtacaaaaa gcagtcgctg ggttacgagt agaagcagcg   2400
gaaaaatcct tttcgcggga ctggctggat gattga                            2436
```

<210> SEQ ID NO 24
<211> LENGTH: 2436
<212> TYPE: DNA
<213> ORGANISM: Artificial Sequence
<220> FEATURE:
<221> NAME/KEY: source
<222> LOCATION: 1..2436
<223> OTHER INFORMATION: /organism="Artificial Sequence"
      /note="Nucleotide sequence HCP7, variant 10"
      /mol_type="unassigned DNA"

<400> SEQUENCE: 24

```
atggcagata ttattggagg agaagtcgtg accgagctcg ttaggcagct ctacgctgtg     60
tcacagaaga cactacgatg ccggggcatt gcaaagaatc ttgcgaccat gatcgatgga    120
cttcaaccca ctatcaagga gatccagtat tccggcgtgg aactgactcc acatagacag    180
gcccagcttc gtatgttttc tgaaacgttg gataaatgta gaaaactaac tgaaaaggtt    240
```

```
ttgaaatcca gtagatggaa catggttaga caaatgctgc atgtccgcaa aatggagaat    300
ctgcaaagca aggtgagctc tttttttaaat ggacaactat tagtacatgt gctcgccgat    360
```



```
ttgaaatcca gtagatggaa catggttaga caaatgctgc atgtccgcaa aatggagaat    300
ctgcaaagca aggtgagctc ttttttaaat ggacaactat tagtacatgt gctcgccgat    360
gtgcaccatg taagggccga ctccgagttt cgatttgaca gaattgatcg caaagtcgat    420
agccttaacg aaaaactcgg atcaatgaag ctgcggggt ctgaatcgct tagggaagca    480
cttaaaacag cggaagcaac tgtggaaatg gtcaccactg atggagcgga cctcggggtt    540
gggctagacc ttggaaagag gaaggtaaag gaaatgttat tcaaaagtat tgatggggag    600
cgtatgattg gaatatctgg tatgtcgggt agtggtaaga caacgctggc taaagagctg    660
gcgcgggatg aagaagtgcg gggtcacttt ggaaacaaag ttatgttttt aactgtttcc    720
caatctccaa atctagaaga gcttcgcgct cacatttggg gattttttgac gtcgtatgag    780
gcggggtcg gggccaccct acctgagtca cggaaattgg tcatcttaga tgatgtttgg    840
acacgtgaat cgctggacca aatgatgttc gaaaacatcc ctggcactac cacgctggtc    900
gtaagtcgga gtaaaatggc agactccaga gttacgtacg atgtggaatt actaaatgag    960
catgaagcta cagccatgtt ttgtctgtcg gtcttcaatc aaaagctcgt gccgtcgggt   1020
ttctcgcaat ccatggtcaa gcaagtcgtc ggtgaatgca agggtcttcc gctaagtttg   1080
aaagtaatcg gggcaagcct gaaggagagg ccggaaaaat actgggaagg agctgtagag   1140
aggctcagtc gtggagagcc cgcggatgaa acgcatgaaa gtcgtgtttt cgcacagata   1200
gaagcgacgt tggaaaatct ggaccctaaa ccagggact gtttcctcgt tttgggagca   1260
tttcctgaag acaaaaagat accattagat gtgctgataa atgtcctagt agaacttcac   1320
gatctcgaag atgctacagc gtttgcggta atagttgatt tggctaacag gaatctattg   1380
acattagtga aagatccaag atttggtcac atgtatacgt catattacga tatttttgtc   1440
acacagcacg atgtcatgcg cgacgtggcc ctccgactta gcaaccatgg aaaggtaaat   1500
aaccgggaga gattaatgat gcctaaacga gaatccatgt tacctcgcga gtgggaaaga   1560
aacaatgatg agccatacaa ggctcgcgtc gtaagcatcc atactggaga aatgacacaa   1620
atggattggt ttgacatgga actgccgaaa gcagaggtga tgattttaca ttttttcgagc   1680
gacaaatatg tgttaccacc tttcatagca aaaatgggga agttgaccgc gctcgtaatc   1740
ataaataatg gcatgtcacc tgcacgactg catgatttct caatctttac gaatttggca   1800
aagctgaaat ctcttttggct tcagcgagtg catgtgccag agcttagctc aagcacagtt   1860
ccgctacaaa acctgcacaa actaagtatg atctttttgta agatcaatac aagcctggat   1920
caaacggaaa tggacattgc acaaattttc cctaagctat ccgatttaac tatagaccat   1980
tgcgatgatt taatggaaat gccatctacg atctgcggta ttacgagcct gaatagcatt   2040
tctatcacca actgtccaag aattaaggaa ttaccaaaaa atctttctaa acttaaagcc   2100
cttcagcttc tcaggttata tgcctgccat gaacttaatt ccctcccgt agagatctgt   2160
gaaatgccta ggctgaagta tgtagacata tcacaatgcg tgagcctaag ctctttacct   2220
gaaaaaatag ggaaagttaa aacgctcgaa aaaatagaca cgcgcgaatg tagcctatcc   2280
tctataccaa actcagtagt cctcctaact tcactaaggc acgtaatatg tgaccgtgag   2340
gccttgtgga tgtgggaaaa agtccaaaaa gccgtggctg gccttcgggt agaagcagca   2400
gaaaaaagtt tcagcaggga ctggttggat gattaa                            2436

<210> SEQ ID NO 25
<211> LENGTH: 2436
<212> TYPE: DNA
<213> ORGANISM: Artificial Sequence
```

<220> FEATURE:
<221> NAME/KEY: source
<222> LOCATION: 1..2436
<223> OTHER INFORMATION: /organism="Artificial Sequence"
    /note="Nucleotide sequence HCP7, variant 11"
    /mol_type="unassigned DNA"

<400> SEQUENCE: 25

| | | | | | |
|---|---|---|---|---|---|
| atggccgata | taattggagg | cgaagttgta | actgaattag | ttcgccaact | atatgccgtc | 60 |
| tctcagaaaa | cgcttcgatg | ccgtgggatc | gcaaaaaacc | tggctacaat | gattgacggc | 120 |
| ttacaaccaa | caataaaaga | gatccagtat | tcggggtcg | aactcacgcc | gcatcgtcaa | 180 |
| gctcaattga | gaatgttcag | tgagaccctc | gacaaatgtc | gtaaactcac | tgaaaaggtg | 240 |
| ttgaaatctt | ctcgttggaa | tatggttcga | caaatgcttc | acgtgcgtaa | gatggagaat | 300 |
| tgcaaagta | aagtgtcctc | ctttctaaac | ggtcaattgt | tggtccatgt | gctggcagat | 360 |
| gtgcaccacg | tcagagctga | ttcagaattt | cgatttgatc | gtatagatag | gaaagtggat | 420 |
| tcccttaacg | agaagctcgg | atctatgaaa | cttaggggtt | cagaaagtct | gagggaagca | 480 |
| ttaaaaactg | cggaagctac | ggtcgaaatg | gtaactaccg | acggagctga | tctgggagta | 540 |
| ggccttgatt | taggaaaaag | aaaggtcaag | gaaatgttat | tcaaatccat | agatggagag | 600 |
| cgtatgatcg | ggatcagcgg | gatgtcaggc | tcggggaaaa | caacgttggc | taaggaactg | 660 |
| gctcgtgacg | aggaggttcg | aggccatttt | ggcaataaag | tgatgttctt | aaccgttagc | 720 |
| caatcaccta | acctcgaaga | attaagggct | cacatatggg | gatttctcac | tagttatgaa | 780 |
| gctggtgtcg | gtgcaacatt | gccagaatct | cgcaagcttg | ttattctcga | cgacgtctgg | 840 |
| actagagaat | cactggacca | aatgatgttt | gaaaacatac | caggaactac | tactcttgtg | 900 |
| gtgtcgagga | gcaaattggc | agatagtcgt | gttacttatg | atgtcgagct | tcttaatgaa | 960 |
| cacgaagcga | ccgccctgtt | ctgcttaagt | gttttcaacc | aaaagctggt | gccgtccggg | 1020 |
| ttctctcaaa | gtttggtcaa | acaggtagtc | ggagaatgta | agggccttcc | gttgagcttg | 1080 |
| aaagtcatcg | gcgcttctct | taaagaacgc | ccggaaaagt | attgggaagg | ggccgtggaa | 1140 |
| cgtctttccc | gaggcgaacc | agctgacgag | actcacgagt | ctcgcgtctt | cgcgcagatc | 1200 |
| gaagctacac | tcgagaacct | cgatccgaaa | acgcgggatt | gttttttagt | gctcggagct | 1260 |
| ttcccagagg | acaaaaagat | accactagag | gtgatgatca | atgtgcttgt | ggaacttcac | 1320 |
| gacctcgaag | atgccactgc | ttttgcagtt | atagttgatt | tagccaaccg | caacttgctt | 1380 |
| acgctcgtca | agatccgcg | attcggccac | atgtacacca | gctactatga | catatttgtc | 1440 |
| actcagcatg | acgtaatgcg | ggacgtggcc | ttaagattaa | gtaaccacgg | aaaggttaat | 1500 |
| aaccgtgaga | ggctaatgat | gcccaaacgg | gagagtatgt | taccgcgcga | atgggagcgt | 1560 |
| aataacgacg | aaccctataa | ggctcgtgtt | gtttcgatac | atacggggga | gatgacgcaa | 1620 |
| atggattggt | tcgacatgga | gctgccaaaa | gcggaagtca | tgattcttca | cttcagcagt | 1680 |
| gacaaatatg | ttctccctcc | cttcatcgct | aaaatgggaa | aactcaccgc | cctggtcata | 1740 |
| attaataatg | gaatgtcacc | tgctagatta | catgattttt | cgatcttcac | caacctcgcg | 1800 |
| aaacttaaaa | gtctatggtt | gcagagggtc | catgtgccag | aattgagctc | ctcgacagta | 1860 |
| cctcttcaaa | atctgcataa | attgagtctg | atcttttgca | aaataaatac | cagcctagat | 1920 |
| caaaccgagc | tggatatcgc | ccaaatctt | cctaagcttt | cggatcttac | tatcgatcac | 1980 |
| tgtgatgatt | tattggaact | gcccagtact | atatgcggga | tcaccagcct | taactctata | 2040 |
| tcaatcacga | attgtccgcg | aatcaaggaa | ttaccgaaga | atctttcaaa | gttaaaagcc | 2100 |

-continued

```
ttgcaactcc ttcgactcta tgcatgccat gaactaaata gtctgccggt tgaaatatgc    2160
gagatgccta ggttgaaata tgtagacatt tctcaatgtg tgtctttgag ttctctccct    2220
gaaaagattg gtaaagtcaa gaccttggaa aagatcgata ctcgtgaatg ttctctttcg    2280
tctatcccta attccgtggt gttgcttacc agtctgaggc acgtaatatg cgatcgcgaa    2340
gccatgtgga tgtgggaaaa agtccaaaaa gcagtcgctg ggctcagagt cgaagctgcc    2400
gaaaaatcct tttcccgtga ctggctggac gattaa                              2436
```

<210> SEQ ID NO 26  
<211> LENGTH: 2436  
<212> TYPE: DNA  
<213> ORGANISM: Artificial Sequence  
<220> FEATURE:  
<221> NAME/KEY: source  
<222> LOCATION: 1..2436  
<223> OTHER INFORMATION: /organism="Artificial Sequence"  
/note="Nucleotide sequence HCP7, variant 12"  
/mol_type="unassigned DNA"

<400> SEQUENCE: 26

```
atggccgaca taattggagg tgaagttgta actgaattgg tgaggcaact ctatgcggtt      60
tcccaaaaga cacttcgctg ccgtggtatc gctaagaacc tcgctactat gatagatggc     120
cttcagccta ctatcaaaga gattcaatat agtggggtgg agctcactcc gcatagacag     180
gctcaacttc ggatgttttc cgagacactc gacaagtgca gaaagttgac cgaaaaagta     240
cttaagagtt ctaggtggaa catggttagg cagatgcttc acgtgaggaa gatggaaaac     300
cttcagtcta aagtctcgtc cttccttaac ggtcagcttc tggttcacgt cctggctgac     360
gttcatcatg tacgcgcaga ttcagagttt aggtttgacc ggatagacag aaaagtcgac     420
tcacttaacg aaaaactcgg aagtatgaaa cttaggggct cggaatcgct tcgtgaagca     480
cttaaaactg ctgaggccac cgttgaaatg gtgactactg acggtgccga ccttggagtc     540
ggattggatc ttggtaagcg taaagttaag gagatgctat ttaaatctat agacggcgag     600
agactgatcg ggatatctgg aatgtccggc tcgggaaaaa ctaccttggc taaggagttg     660
gctagggacg aagaagtgag ggggcatttt gggaacaagg tgttgttcct taccgtgagt     720
caatcaccaa atctcgaaga actccgagct catatctggg ggttcctcac tagttatgaa     780
gccggtgtcg gagctacgct tccagagtct agaaaactag taattctaga tgacgtgtgg     840
acacgcgagt cattagacca gctgatgttt gagaacatcc aggtactac tacgctggtt      900 gtttccaggt ctaaattggc cgactctcgc gtaacctatg acgtagaatt actaaatgag     960
cacgaagcca ccgccatgtt ctgtctttct gtgtttaacc aaaagttagt gccaagcggg    1020
ttctcacaaa gtatggttaa gcaggtggtg ggggaatgca aaggacttcc actttctcta    1080
aaggtgatcg gggcgagttt aaaggaaagg ccagaaaagt actgggaagg cgcagttgaa    1140
cgacttagcc gcggtgagcc agcagatgag actcatgaat cgagagtatt cgctcaaatt    1200
gaagcaaccc tcgagaacct agatcctaag actcgtgact gctttctagt gctcggggct    1260
tttcctgaag acaaaaagat acctctcgac gtcatgataa atgtgctcgt ggagcttcat    1320
gacctcgagg acgctactgc gttcgcagta attgtggatc tagctaatag gaaccttctt    1380
actttagtta aggacccaag gtttgggcac atgtacacta gctactacga tattttcgtg    1440
acccaacacg acgtattgag ggacgtggca ctccggttaa gtaatcatgg caaggtaaac    1500
aatcgtgagc gccttctgat gccaaagcgt gaatctatgc ttccgaggga gtgggagcga    1560
aataacgatg aaccctacaa ggctagagtg gtctcgattc acaccggcga gatgacgcag    1620
```

```
atggattggt tgatatgga gttacctaag gcagaagtcc tgatccttca tttttcaagt    1680
gataagtatg tgctgcctcc cttcattgcg aagatgggaa agcttaccgc actcgtgata    1740
atcaataacg gcatgtcacc tgctcggctt cacgatttct cgatcttcac taacctcgcg    1800
aaactcaaga gtctctggtt gcagcgcgtg cacgttccag agttgagctc ctccaccgtt    1860 cccccttcaaa acctgcataa gttgtccatg attttctgta aaatcaacac tagcctggat    1920
cagacggaaa tggacatcgc tcagattttc cctaagcttt ccgacctcac aattgatcat    1980
tgcgacgatt tattggagat gcctagtaca atatgcggaa tcactagctt aaattctatc    2040
tcgatcacaa actgtcctcg gatcaaggag ctgccgaaaa atctaagtaa acttaaggcg    2100
cttcagctcc tgaggctcta cgcgtgccac gaacttaact ccctccctgt agaaatctgt    2160
gagctgccta ggctaaaata tgtagacatt agtcagtgtg tcagcctcag tagtctcccc    2220
gaaaagatag gcaaggtgaa aaccctcgag aaaatcgaca cccgggaatg ctcccttttca    2280 tctataccta attcagtggt cttattgacg agcttaaggc acgttatctg cgaccgggaa    2340
gctttgtgga tgtgggaaaa ggtgcagaaa gctgtagctg gacttcgcgt tgaagctgcg    2400
gaaaagagtt tctcaaggga ctggttggat gactaa                              2436
```

<210> SEQ ID NO 27
<211> LENGTH: 2436
<212> TYPE: DNA
<213> ORGANISM: Artificial Sequence
<220> FEATURE:
<221> NAME/KEY: source
<222> LOCATION: 1..2436
<223> OTHER INFORMATION: /organism="Artificial Sequence"
      /note="Nucleotide sequence HCP7, variant 13"
      /mol_type="unassigned DNA"

<400> SEQUENCE: 27

```
atggccgaca taatcggagg tgaagttgtg acggagctcg tcaggcagct ctacgctgtt      60
tcgcaaaaga ctcttcggtg tagggggtata gcgaagaacc tcgctactat gatcgatggc     120
ctgcagccta ccatcaaaga gattcagtat tcaggcgtgg agctcactcc ccacagacaa     180
gctcaacttc gaatgtttag cgaaactctc gataagtgcc gtaaactcac cgaaaaagtc     240
cttaaaagtt ctaggtggaa tatggtcagg caaatgttac acgtccgcaa gatggaaaat     300
cttcagagta aagtgagctc gttccttaac ggtcagctcc tcgttcatgt gttggcagac     360
gttcaccatg ttagggcaga ctcagagttt aggtttgatc gtattgatcg taaggtggac     420
tcacttaacg agaagctcgg gtcgatgaag ctaaggggct cagagtcact tagagaagct     480
ttgaagaccg ctgaagctac cgtggaaatg gttactaccg atggtgcaga ccttggagtg     540
gggttagatc tcggtaagcg gaaggtgaag gagatgcttt tcaagtctat cgatggtgag     600
aggctgatcg gcattagtgg tatgtcaggc agtggtaaaa ccaccctcgc caaggaactc     660
gccagggacg aggaggttag gggccacttc ggtaacaagg tgttgtttct taccgtttcc     720
cagtcaccta atctcgagga acttagggct catatctggg gatttctcac tagttacgag     780
gcaggtgttg gagctacttt accagagtct cgaaaactcg tgattctcga tgacgtgtgg     840
acccgggagt cactcgatca gatgatgttc gagaatattc caggtactac cacccctcgtg     900 gtttctaggt cgaagttggc cgattcaagg gtgacctacg atgtggaact tttgaacgag     960
cacgaagcta ccgctatgtt ttgcctgtcg gtgttcaacc agaagctcgt gcctagcgga    1020
tttagccaaa gtttggtgaa gcaagttgtg ggcgagtgta aaggcctccc acttagctta    1080
```

```
aaggtgatcg gcgccagttt aaaagaaagg cctgagaaat actgggaagg tgctgttgag      1140
agactcagta gaggtgaacc agctgacgag actcatgaga gtagagtgtt cgctcagata      1200
gaggcaaccc tcgagaacct cgacccgaag acaagggatt gcttccttgt gctcggcgct      1260
tttccagagg ataagaaaat cccccttagac gtgctgatta acgttctagt tgagcttcac     1320
gatctcgaag acgctactgc gttcgctgtg atagtggacc tcgctaatag gaatctttta     1380
actttggtaa aagaccctag gttcggtcac atgtatacta gctattacga tatcttcgtg     1440
actcagcacg acgttttgag ggacgtagca cttaggctta gtaatcacgg taaagtaaat     1500
aaccgtgaaa ggctactgat gcccaagcgt gagagtatgc ttccccgtga gtgggagcgg     1560
aataatgatg aaccatataa ggctagagtg gtctccattc acaccggcga aatgactcag     1620
atggactggt tcgatatgga gctgcctaag gctgaggtaa tgatactgca ttttagctcc     1680
gacaagtatg tgctccccccc cttcatcgct aagatgggaa aacttactgc cctcgtgata    1740
attaacaacg ggatgtcacc tgctaggctt cacgactttt cgatcttcac aaatctcgct    1800
aagcttaagt ccctgtggct ccaaagggtt catgtgccag agcttagcag ttctacggtg    1860
ccattacaaa acctcacaa acttagcatg atttttctgta agattaacac tagcctagat    1920
cagaccgaga tggatatcgc tcaaatattc cctaagctta gtgacctcac tatagaccac    1980
tgtgacgact tattggagat gcctagtact atttgcggga tcacgagcct taattctatc    2040
tcgataacta actgccctag gataaaggag ctccctaaga acctttctaa gcttaaggcc    2100
cttcaactgc ttcgactcta tgcttgtcac gagcttaatt cactcccagt tgagatctgc    2160
gagatgccta ggcttaagta cgtagacatt agtcagtgcg ttagcctttc atcactcccc    2220
gagaaaatag gtaaggttaa aactcttgaa aagattgata cccgtgaatg ctcactcagc    2280
tctattccca attcagtagt gctcctcact tcgcttaggc acgttatctg tgatagggaa    2340
gctatgtgga tgtgggagaa agtgcagaaa gctgttgctg ggctgcgagt tgaggccgca    2400
gaaaagagtt tctccaggga ctggctcgat gactaa                              2436
```

<210> SEQ ID NO 28
<211> LENGTH: 2436
<212> TYPE: DNA
<213> ORGANISM: Artificial Sequence
<220> FEATURE:
<221> NAME/KEY: source
<222> LOCATION: 1..2436
<223> OTHER INFORMATION: /organism="Artificial Sequence"
    /note="Nucleotide sequence HCP7, variant 14"
    /mol_type="unassigned DNA"

<400> SEQUENCE: 28

```
atggccgaca taatcggtgg tgaggttgtg actgaacttg ttaggcaact atacgccgtt       60
agtcaaaaga cccttaggtg tagggggtatc gctaagaacc tcgctactat gattgacggt     120
cttcagccta ctattaaaga gattcagtac tctggggtgg aactcacccc tcatagacaa      180
gctcaactta ggatgtttag tgagactctc gataaatgcc gtaagctaac tgaaaaagtg     240
cttaagagtt ctaggtggaa tatggtcagg cagctgctac acgttcgtaa aatggaaaac     300
cttcagtcta aagtgagctc gttccttaat ggtcaactcc tcgttcacgt gctagctgac     360
gttcaccacg ttcgtgccga ctctgagttt cgcttcgatc gcatcgaccg taaagtggac     420
tcattgaacg agaagctcgg cagcatgaag cttagggga gtgagtcact tagagaggct     480
cttaagacac tgaggctac cgtggagatg gttactaccg atggtgctga tcttggagta     540
ggacttgatt taggtaaacg taaggttaaa gagatgctct ttaagtctat cgacggagag    600
```

```
cgcatgatcg ggatttccgg aatgagcggc tcaggtaaga ctaccctcgc taaagaactt      660
gcacgggacg aagaggttag gggccacttc ggtaacaagg tcatgttcct tactgttagt      720
cagtcaccta acttggagga gttgagggct catatttggg gctttctcac tagttacgaa      780
gctggagttg gagctactct tccagagtct agaaagctcg tgattctcga cgacgtttgg      840
actagagaat cgcttgatca gctgatgttc gagaatatcc caggtacaac tactctcgtg      900
gttagtaggt ctaaattggc ggattctcga gtgacctacg acgtggagtt acttaatgag      960
catgaggcta ccgcactgtt ttgccttagt gtgtttaatc aaaagctcgt ccctagcggc     1020
tttagtcaga gtttggttaa acaggttgtg ggcgagtgta aaggacttcc actctctctt     1080
aaggtgattg gcgcaagtct taaagagagg ccagagaagt attgggaggg tgctgttgag     1140
agactatcca gaggtgagcc tgctgacgag actcacgaga gtagagtgtt cgctcagatt     1200
gaggctaccc tcgagaacct cgatcctaag actagggatt gcttccttgt gctcggcgct     1260
tttcccgagg ataaaaagat cccactcgac gtgctgatta acgtgctcgt tgagcttcac     1320
gatctcgaag atgcaacggc tttcgctgtg attgtggacc tcgctaatag gaaccttctc     1380
actttagtta aagatcctag gttcggtcac atgtacacga gctattacga tattttcgtg     1440
acgcaacacg atgtattgag ggacgtcgca ctaaggttaa gtaaccacgg taaagttaat     1500
aatagggaac gtctcatgat gcctaagcgt gagtctatgc ttccaagaga atgggagcgt     1560
aacaatgacg aaccctacaa ggctagagta gtctcgattc acaccggcga gatgactcag     1620
atggactggt tcgatatgga actccctaaa gcggaggtac tgatccttca cttttccagc     1680
gataagtacg tgctcccacc ctttattgcc aagatgggaa aacttaccgc cctcgtgatc     1740
attaataacg gaatgagccc agctaggctt cacgattttt cgatattcac caatctcgct     1800
aagctgaaaa gcctctggct tcaacgagtt cacgtccctg agttaagctc ctccacagta     1860
ccacttcaga atcttcacaa acttagcatg atttttctgta agattaatac tagcctcgat     1920
cagaccgaga tggatatcgc tcagattttc cctaagctta gtgacctcac tatcgatcat     1980
tgcgacgacc ttttggagct gcctagtact atctgcggta tcactagcct aaactctatc     2040
tcgatcacta actgccctag gatcaaggag cttccgaaga atcttagtaa gcttaaagcg     2100
ctgcagcttc taaggttata cgcttgtcat gagcttaact cactcccagt cgagatatgc     2160
gagctgcccc gccttaagta tgtagatatc agtcagtgcg taagccttag ctctctcccc     2220
gagaaaattg gtaaggttaa gaccctcgag aagatcgaca cccgtgagtg ttcattgagc     2280
tctattccta attcagtggt gctcctcacg agtcttaggc acgttatctg cgacagggaa     2340
gctttgtgga tgtgggagaa ggttcagaag gcggttgctg gacttcgagt ggaagctgca     2400
gagaagagtt tctctaggga ctggctcgac gattaa                               2436
```

<210> SEQ ID NO 29
<211> LENGTH: 2436
<212> TYPE: DNA
<213> ORGANISM: Artificial Sequence
<220> FEATURE:
<221> NAME/KEY: source
<222> LOCATION: 1..2436
<223> OTHER INFORMATION: /organism="Artificial Sequence"
     /note="Nucleotide sequence HCP7, variant 15"
     /mol_type="unassigned DNA"

<400> SEQUENCE: 29

```
atggccgata taatcggagg tgaggttgtg actgagcttg taaggcagct ctacgctgtt       60
```

```
agccaaaaga cccttaggtg tagggggatc gctaaaaacc tagctaccat gattgacgga    120
ctgcagccta ctatcaaaga gatacagtat tcaggcgtgg aactcacccc tcacagacaa    180
gctcaactta ggatgtttag tgagactctc gataagtgca ggaaacttac cgaaaaagtg    240
ttgaagagtt ctaggtggaa tatggttcgg cagctgcttc acgttcgtaa aatggaaaac    300
ctgcagtcta aggttagcag tttccttaat ggtcagctcc tcgtacacgt gctcgctgac    360
gttcaccatg ttagggctga ctctgagttt cgtttcgata ggatcgaccg taaggtggac    420
tcacttaacg agaagttggg aagtatgaag cttaggggct cagaatcact tcgagaggct    480
ttgaagactg ctgaggctac ggttgagatg gttacaaccg acggtgctga tctaggagtg    540
ggccttgatt taggtaaacg taaggtgaaa gagatgctct ttaagtctat cgacggcgag    600
aggctgatcg ggattagtgg aatgtcagga tcaggtaaga ctaccctcgc taaagaactt    660
gctagggacg aggaggttag gggccacttt ggtaacaagg tcttgttcct taccgttagt    720
cagtcaccta acctcgagga gcttaggggct catatctggg gattcctcac tagttacgag    780
gctggtgttg gagctactct tccagagtct cgcaaactcg tgattctcga cgacgtgtgg    840
actagagagt cactcgacca aatgatgttc gagaatatcc caggtactac taccctcgtc    900
gtttcgagga gtaagatggc cgattctagg gtgacctacg acgtggaact gcttaacgaa    960
cacgaggcta ctgctctgtt ctgccttagt gtttttaatc agaaactcgt gcctagcggg   1020
tttagtcaga gtttggttaa gcaggttgtg ggagagtgta agggactccc acttagcctt   1080
aaggtaatcg gcgctagtct taaagagagg cccgagaagt attgggaggg tgctgttgag   1140
agacttagta gaggtgagcc agctgacgag actcacgagt ctagagtgtt tgctcaaatt   1200
gaggctaccc tcgagaacct cgatcctaaa acgagggatt gcttccttgt gctcggagct   1260
ttccctgagg ataagaaaat cccactcgac gtgctgatta acgtgctcgt ggagcttcac   1320
gacctcgagg acgctactgc tttcgctgtg attgtggacc tcgctaatag gaaccttttta   1380
actttagtta aagatcctag gttcggtcac atgtacacta gctactatga tatcttcgtc   1440
actcagcacg acgtattgag ggacgtagca cttaggctaa gtaatcacgg taaagttaac   1500
aatagggaaa ggctcctgat gcctaagcgt gagtctatgc ttcctagaga gtgggaacgt   1560
aataacgacg aaccctataa ggctagagtg gtttcgattc acaccggcga gatgactcag   1620
atggactggt tcgatatgga actccctaag gctgaagtgc tgatccttca ctttagctcc   1680
gataagtatg tgttgccacc cttttattgct aagatgggaa aacttaccgc actcgtgata   1740
attaacaacg ggatgtcacc agctaggctt catgactttt cgatctttac taaccctcgca   1800
aaacttaagt cactctggct tcagagggtt cacgtaccag aacttagcag ttctactgta   1860
ccacttcaaa accttcacaa gctttcactg atcttctgta aaattaacac tagcctcgat   1920
cagactgagc tggatatcgc tcagattttc cctaagctta gtgacctgac aatcgatcat   1980
tgcgacgacc ttttggagct gcccagtacg atatgcggta taactagcct taactctatt   2040
tcgatcacaa actgccctag gatcaaagaa cttcctaaga accttagtaa gcttaaggcc   2100
cttcagctcc ttcgtctcta cgcttgccac gagcttaact cactcccagt cgaaatatgc   2160
gagctgccac gactgaagta cgtagacatt agtcagtgcg taagccttag cagtctcccc   2220
gagaagattg ggaaagttaa gaccctcgag aagatcgata cccgtgagtg ctcacttagc   2280
tctattccta actcagtggt gcttctcact agtcttaggc acgtcatatg cgatagggag   2340
gctttgtgga tgtgggagaa ggttcagaag gctgttgctg gacttagagt tgaggctgcc   2400
gagaagagtt tttctaggga ttggctcgac gactaa                             2436
```

<210> SEQ ID NO 30
<211> LENGTH: 2436
<212> TYPE: DNA
<213> ORGANISM: Artificial Sequence
<220> FEATURE:
<221> NAME/KEY: source
<222> LOCATION: 1..2436
<223> OTHER INFORMATION: /organism="Artificial Sequence"
/note="Nucleotide sequence HCP7, variant 16"
/mol_type="unassigned DNA"

<400> SEQUENCE: 30

| | | | | | |
|---|---|---|---|---|---|
| atggccgata | taatcggagg | cgaggtggta | actgagcttg | ttaggcagct | ctacgccgtt | 60 |
| agtcaaaaga | cccttaggtg | taggggatc | gctaagaacc | tcgctactat | gattgacggc | 120 |
| cttcagccta | ctatcaagga | aattcagtac | tcaggcgtgg | aactcacccc | tcatagacaa | 180 |
| gctcaactta | ggatgtttag | cgagactctc | gataagtgcc | gtaagctcac | cgagaaagtg | 240 |
| cttaagagtt | ctaggtggaa | tatggttagg | cagatgcttc | acgttaggaa | gatggaaaac | 300 |
| cttcaaagta | aagttagcag | ttttcttaac | ggtcaactcc | tcgttcatgt | gctcgctgac | 360 |
| gttcaccacg | ttagggctga | ctcagagttt | aggttcgata | ggatcgaccg | taaggtggac | 420 |
| tcacttaacg | agaagctcgg | ctctatgaag | cttaggggct | cggagtcact | tagagaggct | 480 |
| cttaagactg | ctgaagctac | cgttgagatg | gttactaccg | acggggctga | ccttggagtg | 540 |
| ggacttgatc | tcggtaagcg | taaggtgaaa | gagatgttgt | ttaagtctat | cgacggcgag | 600 |
| aggctgatcg | ggataagtgg | aatgagcggt | tcaggtaaga | ctaccctcgc | taaagaactt | 660 |
| gctagggacg | aagaggttag | gggccacttc | ggtaacaagg | tgttgttcct | taccgttagt | 720 |
| cagtcaccta | acctcgagga | acttagggct | catatctggg | gtttcctcac | tagttacgag | 780 |
| gctggtgttg | gagctactct | tcctgagtct | agaaaactag | tgattctcga | tgacgtgtgg | 840 |
| actagagagt | cactcgatca | gctgatgttt | gagaatatcc | caggtactac | tacgctcgtg | 900 |
| gttagtaggt | ccaagttggc | cgattctagg | gtgacctacg | acgtggaact | tcttaacgaa | 960 |
| cacgaggcta | ccgctatgtt | ctgccttagt | gtgtttaatc | agaaactcgt | gcctagcggc | 1020 |
| ttcagtcaga | gtatggttaa | gcaggttgtg | ggagagtgta | agggactccc | attaagcctt | 1080 |
| aaggtgatcg | gcgctagtct | taaagagagg | ccagagaagt | attgggaggg | tgctgttgag | 1140 |
| agactttcta | gaggtgaacc | agctgacgag | actcacgagt | ctagagtgtt | cgctcaaatc | 1200 |
| gaggctaccc | tagagaacct | cgatccgaaa | actagggatt | gcttccttgt | gctcggagct | 1260 |
| ttcccagagg | ataagaaaat | cccactcgac | gtgctgatta | cgtgctcgt | tgagcttcac | 1320 |
| gatttggagg | atgctactgc | tttcgctgtg | attgtggacc | tcgctaacag | gaacctactc | 1380 |
| actttagtta | aggaccctag | gtttggtcac | atgtacacta | gctactacga | tatcttcgtg | 1440 |
| actcagcacg | acgtattgag | ggacgtagca | cttaggctta | gtaatcacgg | gaaagtgaac | 1500 |
| aatagggaaa | ggctcctgat | gcctaagcgt | gaatctatgc | ttcctagaga | gtgggagcgt | 1560 |
| aacaacgatg | agccctataa | ggctagagtg | gtctcgatac | acaccggtga | gatgactcag | 1620 |
| atggactggt | tcgatatgga | actccctaag | gctgaggtga | tgatccttca | ttttagctca | 1680 |
| gataagtacg | tgctcccacc | ctttattgct | aagatgggaa | agctaaccgc | cctcgtgata | 1740 |
| attaacaacg | ggatgtcacc | agctaggctt | cacgactttt | cgatcttcac | aaacctcgct | 1800 |
| aagcttaagt | cactctggct | tcagcgtgtt | cacgtgccag | agttaagcag | ttctactgta | 1860 |
| ccacttcaga | accttcacaa | gcttagcctg | atcttctgta | aaattaacac | tagcctcgat | 1920 |

```
cagaccgagc tggatatcgc tcagattttc cctaagctta gtgacctcac tatcgatcac   1980
tgcgacgacc ttttggagct gcctagtact atatgcggga tcactagcct taactctatt   2040
tcgatcacta actgccctag gatcaaagag cttcctaaga acctttccaa gcttaaagcc   2100
cttcagctcc ttaggctcta cgcttgtcac gagcttaact cattgccagt tgagatctgc   2160
gagctgcctc gattaaagta tgtagacatt agtcagtgcg tgagccttag ctcactcccc   2220
gaaaagattg gtaaggttaa gaccctcgag aagatcgata cccgtgaatg ttcacttagc   2280
tctatcccga actcagtggt gctcctaact agtcttaggc acgttatctg cgatagggaa   2340
gctttgtgga tgtgggagaa ggttcagaag gctgttgctg gattaagagt cgaagctgcc   2400
gagaagagtt tctctaggga ttggctcgac gactaa                             2436
```